United States Patent [19]

Vandlen et al.

[11] Patent Number: 5,840,525
[45] Date of Patent: Nov. 24, 1998

[54] NUCLEIC ACIDS, VECTORS AND HOST CELLS ENCODING HEREGULIN

[75] Inventors: Richard L. Vandlen, Hillsborough; William E. Holmes, Pacifica, both of Calif.

[73] Assignee: Genentech, Inc., South San Francisco, Calif.

[21] Appl. No.: 456,241

[22] Filed: May 31, 1995

Related U.S. Application Data

[62] Division of Ser. No. 126,145, Sep. 23, 1993, abandoned, which is a continuation of Ser. No. 880,917, May 11, 1992, abandoned, which is a continuation-in-part of Ser. No. 847,743, Mar. 6, 1992, Pat. No. 5,367,060, which is a continuation-in-part of Ser. No. 790,801, Nov. 8, 1991, abandoned, which is a continuation-in-part of Ser. No. 765,212, Sep. 25, 1991, abandoned, which is a continuation-in-part of Ser. No. 705,256, May 24, 1991, abandoned.

[51] Int. Cl.$^6$ ............ C12N 15/00; C12N 15/63; C12N 15/85; C12N 1/21; C07H 21/04
[52] U.S. Cl. ............ 435/69.1; 435/320.1; 435/325; 435/252.3; 536/23.5; 935/77; 935/78
[58] Field of Search ............ 435/69.1, 320.1, 435/242.7, 325, 252.3; 536/23.5; 530/350, 399

[56] References Cited

U.S. PATENT DOCUMENTS

| | | | |
|---|---|---|---|
| 4,683,195 | 7/1987 | Mullis et al. | 435/91.2 |
| 4,882,275 | 11/1989 | Klagsburn | 435/68 |
| 4,968,603 | 11/1990 | Slamon et al. | 435/6 |
| 5,169,837 | 12/1992 | Lagarde et al. | 514/21 |
| 5,237,056 | 8/1993 | Fischbach | 435/6 |
| 5,367,060 | 11/1994 | Vandlen et al. | 530/399 |
| 5,464,751 | 11/1995 | Greene et al. | 435/7.23 |
| 5,578,482 | 11/1996 | Lippman et al. | 435/384 |
| 5,594,114 | 1/1997 | Goodearl et al. | 530/399 |
| 5,641,869 | 6/1997 | Vandlen et al. | 530/413 |

FOREIGN PATENT DOCUMENTS

| | | |
|---|---|---|
| 505148 | 9/1993 | European Pat. Off. . |
| WO 91/15230 | 10/1991 | WIPO . |
| WO 91/18921 | 12/1991 | WIPO . |
| 92/00595 | 4/1992 | WIPO . |
| WO 92/12174 | 7/1992 | WIPO . |
| WO 92/18627 | 10/1992 | WIPO . |
| WO 93/22339 | 11/1993 | WIPO . |
| WO 93/22424 | 11/1993 | WIPO . |

OTHER PUBLICATIONS

"Using the PolyCAT A Column" *PolyLC: HPLC Supplies for the Life Sciences* (and Application Note: HPLC of Hemoglobins on PolyCAT A), Columbia, MD: PolyLC Inc.

Alpert, "Cation–exchange high–performance liquid chromatography of proteins on poly(aspartic acid)–silica" *J. Chromatogr.* 266:23–37 (1983).

Benveniste et al., "Purification and characterization of a human T–lymphocyte–derived glial growth–promoting factor" *Proc. Natl. Acad. Sci.* 82:3930–3934 (1985).

Brockes, "Assay and isolation of glial growth factor from the bovine pituitary" *Methods in Enzymology* 147:217–225 (1987).

Brockes et al., "Glial growth factor–like activity in Schwann Cell tumors" *Annals of Neurology* 20:317–322 (1986).

(List continued on next page.)

*Primary Examiner*—Lisa B. Arthur
*Attorney, Agent, or Firm*—Wendy M. Lee

[57] ABSTRACT

A novel polypeptide with binding affinity for the p185$^{HER2}$ receptor, designated heregulin-α, has been identified and purified from cultured human cells. DNA sequences encoding additional heregulin polypeptides, designated heregulin-α, heregulin-β1, heregulin-β2, heregulin-β2-like, and heregulin-β3, have been isolated, sequenced and expressed. Provided herein are nucleic acid sequences encoding the amino acid sequences of heregulins useful in the production of heregulins by recombinant means. Further provided are the amino acid sequences of heregulins and purification methods therefor. Heregulins and their antibodies are useful as therapeutic agents and in diagnostic methods.

29 Claims, 33 Drawing Sheets

OTHER PUBLICATIONS

Brockes et al., "Purification and preliminary characterization of a glial growth factor from the bovine pituitary" *Journal of Biological Chemistry* 255(18):8374–8377 (1980).

Davis et al., "Isolation and characterization of a neu protein–specific activating factor from human ATL–2 cell conditioned medium" *Biochem. & Biophys. Res. Comm.* 179(3):1536–1542 (1991).

Davis et al., "Platelet–derived growth factors and fibroblast growth factors are mitogens for rat Schwann Cells" *Journal of Cell Biology* 110:1353–1360 (1990).

De Corte et al., "A 50 kDa protein present in conditioned medium of COLO–16 cells stimulates cell spreading and motility, and activates tyrosine phosphorylation of Neu/HER–2, in human SK–BR–3 mammary cancer cells" *J. Cell Science* 107:405–416 (1994).

Dobashi et al., "Characterization of a neu/c–erbB–2 protein–specific activating factor" *Proc. Natl. Acad. Sci.* 88:8582–8596 (1991).

Falls et al., "ARIA, a protein that stimulates acetylcholine receptor synthesis, is a member of the Neu ligand family" *Cell* 72: 801–815 (1993).

Fitzgerald et al., "Characterization and Sequence Analysis of the Human Ornithine Decarboxylase Gene" *DNA* 8(9):623–634 (1989).

Gray et al., "Nucleotide sequence of epidermal growth factor cDNA predicts a 128,000–molecular weight protein precursor" *Nature* 303:722–725 (1983).

Hoffman, Michelle, "New Clue Found to Oncogene's Role in Breast Cancer" *Science* 256:1129 (1992).

Holmes et al., "Identification of heregulin, a specific activator of p185$^{erbB2}$" *Science* 256:1205–1210 (1992).

Hudziak et al., "p185$^{HER2}$ Monoclonal Antibody Has Antiproliferative Effects In Vitro and Sensitizes Human Breast Tumor Cells to Tumor Necrosis Factor" *Molecular & Cellular Biology* 9(3):1165–1172 (1989).

Kimura et al., "Structure, expression and function of a schwannoma–derived growth factor" *Nature* 348:257–260 (1990).

Kokai et al., "Phosphorylation process induced by epidermal growth factor alters the oncogenic and cellular neu (NGL) gene products" *Proc. Natl. Acad. Sci USA* 85:5389–5393 (1988).

Kunisada et al., "Sequence Organization of Repetitive Sequences Enriched in Small Polydisperse Circular DNAs from HeLa Cells" *J. Mol. Biol.* 198:557–565 (1987).

Lemke & Brockes, "Identification and purification of glial growth factor" *J. Neurosci.* 4(1):75–83 (1984).

Lupu et al., "Direct interaction of a ligand for the erbB2 oncogene product with the EGF receptor and p185$^{erbB2}$" *Science* 249:1552–1555.

Lupu et al., "Purification and Characterization of Novel Growth Factor from Human Breast Cancer Cells" *Biochemistry* 31:7330–7340 (1992).

Lupu et al., "Purification of a novel growth factor that binds exclusively to the erbB–2 receptor protein and induces cellular responses" *Proc. Am. Assoc. Cancer Res.* 32:abst. No. 297, p. 50 (1991).

Maniatis et al. *Molecular Cloning: A Laboratory Manual*, Cold Spring Harber Lab. pp. 412–433 (1982).

Marchionni et al., "Glial growth factors are alternatively spliced erbB2 ligands expressed in the nervous system" *Nature* 362:312–318 (1993).

Nagata et al., "Solution structure of the epidermal growth factor–like domain of heregulin–α, a ligand for p180$^{erbB-4}$" *EMBO J*, 13(15):3517–3523 (1994).

Peles et al., "Isolation of the Neu/HER–2 Stimulatory Ligand: A 44 Kd Glycoprotein That Induces Differentiation of Mammary Tumor Cells" *Cell* 69(1):205–216 (1992).

Pohlenz et al., "The Human VK Locus, Characterization of Extended Immunoglobulin Gene Regions by Cosmid Cloning" *J. Mol. Biol.* 193:241–253 (1987).

Sliwkowski et al., "Coexpression of erbB2 and erbB3 proteins reconstitutes a high affinity receptor for heregulin" *Journal of Biological Chemistry* 269(20):14661–14665 (1994).

Smith et al., "The Major Constituents of Cells" *Principles of Biochemistry: General Aspects*, McGraw–Hill Book Co., New York p. 164 (7th Edition 1983).

Tarakhovsky et al., "A 25 kDa polypeptide is the ligand for p185Neu and is secreted by activated macrophages" *Oncogene* 6(12):2187–2196 (1991).

Wen et al., "Neu differentiation factor: a transmembrane glycoprotein containing an EGF Domain and an Immunoglobulin Homology Unit" *Cell* 69(3):559–572 (1992).

Xu et al. *Eighty–Second Annual Meeting of the American Association for Cancer Research Proceedings* 32:260 (Abstract No. 1544 1991).

Yarden, "Biochemical Analysis of the Ligand for the neu Oncogenic Receptor" *Biochemistry* 30:3543–3550 (1991).

Yarden et al., "Experimental approaches to hypothetical hormones: detection of a candidate ligand of the neu protooncogene" *Proc. Natl. Acad. Sci. USA* 86:3179–3183 (1989).

"Paper No. 7" (Amendment A) from file history of USSN 08/096,277 (now US Patent 5,578,482).

"Paper No. 8" (Office Action) from file history of USSN 08/096,277 (now US Patent No. 5,578,482).

Groenen et al., "Structure–function relationships for the EGF/TGF/–alpha family of mitogens" *Growth Factors* 11:235–237 (1994).

```
GG  GCG CGA GCG CCT CAG CGC GGC CGC TCG CTC TCC CCC  38
    Ala Arg Ala Pro Gln Arg Gly Arg Ser Leu Ser Pro
    1            5                   10

TCG AGG GAC AAA CTT TTC CCA AAC CCG ATC CGA GCC CTT  77
Ser Arg Asp Lys Leu Phe Pro Asn Pro Ile Arg Ala Leu
        15              20                      25

GGA CCA AAC TCG CCT GCG CCG AGA GCC GTC CGC GTA GAG  116
Gly Pro Asn Ser Pro Ala Pro Arg Ala Val Arg Val Glu
                30                  35

CGC TCC GTC TCC GGC GAG ATG TCC GAG CGC AAA GAA GGC  155
Arg Ser Val Ser Gly Glu Met Ser Glu Arg Lys Glu Gly
        40              45                  50

AGA GGC AAA GGG AAG GGC AAG AAG AAG GAG CGA GGC TCC  194
Arg Gly Lys Gly Lys Gly Lys Lys Lys Glu Arg Gly Ser
            55                  60

GGC AAG AAG CCG GAG TCC GCG GCG GGC AGC CAG AGC CCA  233
Gly Lys Lys Pro Glu Ser Ala Ala Gly Ser Gln Ser Pro
65              70                  75

GCC TTG CCT CCC CGA TTG AAA GAG ATG AAA AGC CAG GAA  272
Ala Leu Pro Pro Arg Leu Lys Glu Met Lys Ser Gln Glu
        80              85                      90

TCG GCT GCA GGT TCC AAA CTA GTC CTT CGG TGT GAA ACC  311
Ser Ala Ala Gly Ser Lys Leu Val Leu Arg Cys Glu Thr
                95                  100

AGT TCT GAA TAC TCC TCT CTC AGA TTC AAG TGG TTC AAG  350
Ser Ser Glu Tyr Ser Ser Leu Arg Phe Lys Trp Phe Lys
105                 110                 115

AAT GGG AAT GAA TTG AAT CGA AAA AAC AAA CCA CAA AAT  389
Asn Gly Asn Glu Leu Asn Arg Lys Asn Lys Pro Gln Asn
            120                 125

ATC AAG ATA CAA AAA AAG CCA GGG AAG TCA GAA CTT CGC  428
Ile Lys Ile Gln Lys Lys Pro Gly Lys Ser Glu Leu Arg
130                 135                 140

ATT AAC AAA GCA TCA CTG GCT GAT TCT GGA GAG TAT ATG  467
Ile Asn Lys Ala Ser Leu Ala Asp Ser Gly Glu Tyr Met
        145                 150                 155

TGC AAA GTG ATC AGC AAA TTA GGA AAT GAC AGT GCC TCT  506
Cys Lys Val Ile Ser Lys Leu Gly Asn Asp Ser Ala Ser
            160                 165
```

FIG. 4A

```
GCC AAT ATC ACC ATC GTG GAA TCA AAC GAG ATC ATC ACT  545
Ala Asn Ile Thr Ile Val Glu Ser Asn Glu Ile Ile Thr
    170             175             180

GGT ATG CCA GCC TCA ACT GAA GGA GCA TAT GTG TCT TCA  584
Gly Met Pro Ala Ser Thr Glu Gly Ala Tyr Val Ser Ser
        185             190

GAG TCT CCC ATT AGA ATA TCA GTA TCC ACA GAA GGA GCA  623
Glu Ser Pro Ile Arg Ile Ser Val Ser Thr Glu Gly Ala
195             200             205

AAT ACT TCT TCA TCT ACA TCT ACA TCC ACC ACT GGG ACA  662
Asn Thr Ser Ser Ser Thr Ser Thr Ser Thr Thr Gly Thr
            210             215             220

AGC CAT CTT GTA AAA TGT GCG GAG AAG GAG AAA ACT TTC  701
Ser His Leu Val Lys Cys Ala Glu Lys Glu Lys Thr Phe
                225             230

TGT GTG AAT GGA GGG GAG TGC TTC ATG GTG AAA GAC CTT  740
Cys Val Asn Gly Gly Glu Cys Phe Met Val Lys Asp Leu
        235             240             245

TCA AAC CCC TCG AGA TAC TTG TGC AAG TGC CAA CCT GGA  779
Ser Asn Pro Ser Arg Tyr Leu Cys Lys Cys Gln Pro Gly
            250             255

TTC ACT GGA GCA AGA TGT ACT GAG AAT GTG CCC ATG AAA  818
Phe Thr Gly Ala Arg Cys Thr Glu Asn Val Pro Met Lys
260             265             270

GTC CAA AAC CAA GAA AAG GCG GAG GAG CTG TAC CAG AAG  857
Val Gln Asn Gln Glu Lys Ala Glu Glu Leu Tyr Gln Lys
        275             280             285

AGA GTG CTG ACC ATA ACC GGC ATC TGC ATC GCC CTC CTT  896
Arg Val Leu Thr Ile Thr Gly Ile Cys Ile Ala Leu Leu
            290             295

GTG GTC GGC ATC ATG TGT GTG GTG GCC TAC TGC AAA ACC  935
Val Val Gly Ile Met Cys Val Val Ala Tyr Cys Lys Thr
        300             305             310

AAG AAA CAG CGG AAA AAG CTG CAT GAC CGT CTT CGG CAG  974
Lys Lys Gln Arg Lys Lys Leu His Asp Arg Leu Arg Gln
            315             320

AGC CTT CGG TCT GAA CGA AAT AAT ATG ATG AAC ATT GCC 1013
Ser Leu Arg Ser Glu Arg Asn Asn Met Met Asn Ile Ala
325             330             335
```

FIG. 4B

```
AAT GGG CCT CAC CAT CCT AAC CCA CCC CCC GAG AAT GTC  1052
Asn Gly Pro His His Pro Asn Pro Pro Pro Glu Asn Val
        340             345             350

CAG CTG GTG AAT CAA TAC GTA TCT AAA AAC GTC ATC TCC  1091
Gln Leu Val Asn Gln Tyr Val Ser Lys Asn Val Ile Ser
            355             360

AGT GAG CAT ATT GTT GAG AGA GAA GCA GAG ACA TCC TTT  1130
Ser Glu His Ile Val Glu Arg Glu Ala Glu Thr Ser Phe
    365             370             375

TCC ACC AGT CAC TAT ACT TCC ACA GCC CAT CAC TCC ACT  1169
Ser Thr Ser His Tyr Thr Ser Thr Ala His His Ser Thr
            380             385

ACT GTC ACC CAG ACT CCT AGC CAC AGC TGG AGC AAC GGA  1208
Thr Val Thr Gln Thr Pro Ser His Ser Trp Ser Asn Gly
390             395             400

CAC ACT GAA AGC ATC CTT TCC GAA AGC CAC TCT GTA ATC  1247
His Thr Glu Ser Ile Leu Ser Glu Ser His Ser Val Ile
        405             410             415

GTG ATG TCA TCC GTA GAA AAC AGT AGG CAC AGC AGC CCA  1286
Val Met Ser Ser Val Glu Asn Ser Arg His Ser Ser Pro
                420             425

ACT GGG GGC CCA AGA GGA CGT CTT AAT GGC ACA GGA GGC  1325
Thr Gly Gly Pro Arg Gly Arg Leu Asn Gly Thr Gly Gly
    430             435             440

CCT CGT GAA TGT AAC AGC TTC CTC AGG CAT GCC AGA GAA  1364
Pro Arg Glu Cys Asn Ser Phe Leu Arg His Ala Arg Glu
            445             450

ACC CCT GAT TCC TAC CGA GAC TCT CCT CAT AGT GAA AGG  1403
Thr Pro Asp Ser Tyr Arg Asp Ser Pro His Ser Glu Arg
455             460             465

TAT GTG TCA GCC ATG ACC ACC CCG GCT CGT ATG TCA CCT  1442
Tyr Val Ser Ala Met Thr Thr Pro Ala Arg Met Ser Pro
        470             475             480

GTA GAT TTC CAC ACG CCA AGC TCC CCC AAA TCG CCC CCT  1481
Val Asp Phe His Thr Pro Ser Ser Pro Lys Ser Pro Pro
            485             490

TCG GAA ATG TCT CCA CCC GTG TCC AGC ATG ACG GTG TCC  1520
Ser Glu Met Ser Pro Pro Val Ser Ser Met Thr Val Ser
    495             500             505
```

FIG. 4C

```
ATG CCT TCC ATG GCG GTC AGC CCC TTC ATG GAA GAA GAG   1559
Met Pro Ser Met Ala Val Ser Pro Phe Met Glu Glu Glu
            510                 515

AGA CCT CTA CTT CTC GTG ACA CCA CCA AGG CTG CGG GAG   1598
Arg Pro Leu Leu Leu Val Thr Pro Pro Arg Leu Arg Glu
520                 525                 530

AAG AAG TTT GAC CAT CAC CCT CAG CAG TTC AGC TCC TTC   1637
Lys Lys Phe Asp His His Pro Gln Gln Phe Ser Ser Phe
            535                 540                 545

CAC CAC AAC CCC GCG CAT GAC AGT AAC AGC CTC CCT GCT   1676
His His Asn Pro Ala His Asp Ser Asn Ser Leu Pro Ala
                550                 555

AGC CCC TTG AGG ATA GTG GAG GAT GAG GAG TAT GAA ACG   1715
Ser Pro Leu Arg Ile Val Glu Asp Glu Glu Tyr Glu Thr
    560                 565                 570

ACC CAA GAG TAC GAG CCA GCC CAA GAG CCT GTT AAG AAA   1754
Thr Gln Glu Tyr Glu Pro Ala Gln Glu Pro Val Lys Lys
                575                 580

CTC GCC AAT AGC CGG CGG GCC AAA AGA ACC AAG CCC AAT   1793
Leu Ala Asn Ser Arg Arg Ala Lys Arg Thr Lys Pro Asn
585                 590                 595

GGC CAC ATT GCT AAC AGA TTG GAA GTG GAC AGC AAC ACA   1832
Gly His Ile Ala Asn Arg Leu Glu Val Asp Ser Asn Thr
            600                 605                 610

AGC TCC CAG AGC AGT AAC TCA GAG AGT GAA ACA GAA GAT   1871
Ser Ser Gln Ser Ser Asn Ser Glu Ser Glu Thr Glu Asp
                615                 620

GAA AGA GTA GGT GAA GAT ACG CCT TTC CTG GGC ATA CAG   1910
Glu Arg Val Gly Glu Asp Thr Pro Phe Leu Gly Ile Gln
    625                 630                 635

AAC CCC CTG GCA GCC AGT CTT GAG GCA ACA CCT GCC TTC   1949
Asn Pro Leu Ala Ala Ser Leu Glu Ala Thr Pro Ala Phe
            640                 645

CGC CTG GCT GAC AGC AGG ACT AAC CCA GCA GGC CGC TTC   1988
Arg Leu Ala Asp Ser Arg Thr Asn Pro Ala Gly Arg Phe
650                 655                 660

TCG ACA CAG GAA GAA ATC CAG G                         2010
Ser Thr Gln Glu Glu Ile Gln
            665         669
```

```
              221                      230             240             250          260
HRG2-alpha    S H L V K C A E K T F C V N G G E C F M V K D L S N P S R Y L C K C Q P G F T G A R C T E N
EGF           N S D S E C P L S H D G Y C L H D G V C M Y I E A L - - D K Y A C N C V V G Y I G E R C Q Y R
TGF-alpha         N D C P D S H T Q F C F H - G T C R F L V Q E - - D K P A C V C H S G Y V G A R C E H A
Amphiregulin  K K K N P C N A E F Q N F C I H - G E C K Y I E H L - - E A V T C K C Q Q E Y F G E R C G E K
Schwannoma    K K K N P C A A K F Q N F C I H - G E C R Y I E N L - - E V V T C H C H Q D Y F G E R C G E K
HB-EGF        K K R D P C L R K Y K D F C I H - G E C K Y V K E L - - R A P S C I C H P G Y H G E R C H G L 270              280                      290             300             310
HRG2-alpha    V P M K V Q N Q E K A E E L Y Q K R V L T I T G I C I A L L V V G I M C V V A Y C K T K K Q R .
EGF           D L K W W E L R                    K V I V V A V C V V V L V M L L L L S L W G A H Y Y R T Q K
TGF-alpha     D L L A                            K Q A I T A L V V V S I V A L A V L I I T C V L I H C C Q V
Amphiregulin  S M K T H S M I D S S L S          K I A L A A I A A F M S A V I L T A V A V I T V Q L R R Q Y
Schwannoma    T M K T Q K K D D S D L S          K I A L A A I I V F V S A V S V A A I G I I T A V L L R K R
HB-EGF        S L P V E N R L Y T Y D            H T T I L A V V A V V L L S V C L L V I V G L L M F R Y H R
                                                          TRANSMEMBRANE REGION
```

```
GG  GAC AAA CTT TTC CCA AAC CCG ATC CGA GCC CTT GGA  38
    Asp Lys Leu Phe Pro Asn Pro Ile Arg Ala Leu Gly
    1           5                   10

CCA AAC TCG CCT GCG CCG AGA GCC GTC CGC GTA GAG CGC  77
Pro Asn Ser Pro Ala Pro Arg Ala Val Arg Val Glu Arg
        15              20                      25

TCC GTC TCC GGC GAG ATG TCC GAG CGC AAA GAA GGC AGA  116
Ser Val Ser Gly Glu Met Ser Glu Arg Lys Glu Gly Arg
                30                  35

GGC AAA GGG AAG GGC AAG AAG AAG GAG CGA GGC TCC GGC  155
Gly Lys Gly Lys Gly Lys Lys Lys Glu Arg Gly Ser Gly
        40              45                  50

AAG AAG CCG GAG TCC GCG GCG GGC AGC CAG AGC CCA GCC  194
Lys Lys Pro Glu Ser Ala Ala Gly Ser Gln Ser Pro Ala
            55                  60

TTG CCT CCC CAA TTG AAA GAG ATG AAA AGC CAG GAA TCG  233
Leu Pro Pro Gln Leu Lys Glu Met Lys Ser Gln Glu Ser
65              70                  75

GCT GCA GGT TCC AAA CTA GTC CTT CGG TGT GAA ACC AGT  272
Ala Ala Gly Ser Lys Leu Val Leu Arg Cys Glu Thr Ser
        80                  85                  90

TCT GAA TAC TCC TCT CTC AGA TTC AAG TGG TTC AAG AAT  311
Ser Glu Tyr Ser Ser Leu Arg Phe Lys Trp Phe Lys Asn
                95                  100

GGG AAT GAA TTG AAT CGA AAA AAC AAA CCA CAA AAT ATC  350
Gly Asn Glu Leu Asn Arg Lys Asn Lys Pro Gln Asn Ile
105                 110                 115

AAG ATA CAA AAA AAG CCA GGG AAG TCA GAA CTT CGC ATT  389
Lys Ile Gln Lys Lys Pro Gly Lys Ser Glu Leu Arg Ile
            120                 125

AAC AAA GCA TCA CTG GCT GAT TCT GGA GAG TAT ATG TGC  428
Asn Lys Ala Ser Leu Ala Asp Ser Gly Glu Tyr Met Cys
130                 135                 140

AAA GTG ATC AGC AAA TTA GGA AAT GAC AGT GCC TCT GCC  467
Lys Val Ile Ser Lys Leu Gly Asn Asp Ser Ala Ser Ala
            145                 150                 155

AAT ATC ACC ATC GTG GAA TCA AAC GAG ATC ATC ACT GGT  506
Asn Ile Thr Ile Val Glu Ser Asn Glu Ile Ile Thr Gly
                160                 165
```

FIG. 8A

```
ATG CCA GCC TCA ACT GAA GGA GCA TAT GTG TCT TCA GAG  545
Met Pro Ala Ser Thr Glu Gly Ala Tyr Val Ser Ser Glu
    170                 175                 180

TCT CCC ATT AGA ATA TCA GTA TCC ACA GAA GGA GCA AAT  584
Ser Pro Ile Arg Ile Ser Val Ser Thr Glu Gly Ala Asn
            185                 190

ACT TCT TCA TCT ACA TCT ACA TCC ACC ACT GGG ACA AGC  623
Thr Ser Ser Ser Thr Ser Thr Ser Thr Thr Gly Thr Ser
195                 200                 205

CAT CTT GTA AAA TGT GCG GAG AAG GAG AAA ACT TTC TGT  662
His Leu Val Lys Cys Ala Glu Lys Glu Lys Thr Phe Cys
        210                 215                 220

GTG AAT GGA GGG GAG TGC TTC ATG GTG AAA GAC CTT TCA  701
Val Asn Gly Gly Glu Cys Phe Met Val Lys Asp Leu Ser
                225                 230

AAC CCC TCG AGA TAC TTG TGC AAG TGC CCA AAT GAG TTT  740
Asn Pro Ser Arg Tyr Leu Cys Lys Cys Pro Asn Glu Phe
    235                 240                 245

ACT GGT GAT CGC TGC CAA AAC TAC GTA ATG GCC AGC TTC  779
Thr Gly Asp Arg Cys Gln Asn Tyr Val Met Ala Ser Phe
            250                 255

TAC AAG CAT CTT GGG ATT GAA TTT ATG GAG GCG GAG GAG  818
Tyr Lys His Leu Gly Ile Glu Phe Met Glu Ala Glu Glu
260                 265                 270

CTG TAC CAG AAG AGA GTG CTG ACC ATA ACC GGC ATC TGC  857
Leu Tyr Gln Lys Arg Val Leu Thr Ile Thr Gly Ile Cys
        275                 280                 285

ATC GCC CTC CTT GTG GTC GGC ATC ATG TGT GTG GTG GCC  896
Ile Ala Leu Leu Val Val Gly Ile Met Cys Val Val Ala
                290                 295

TAC TGC AAA ACC AAG AAA CAG CGG AAA AAG CTG CAT GAC  935
Tyr Cys Lys Thr Lys Lys Gln Arg Lys Lys Leu His Asp
    300                 305                 310

CGT CTT CGG CAG AGC CTT CGG TCT GAA CGA AAC AAT ATG  974
Arg Leu Arg Gln Ser Leu Arg Ser Glu Arg Asn Asn Met
            315                 320

ATG AAC ATT GCC AAT GGG CCT CAC CAT CCT AAC CCA CCC 1013
Met Asn Ile Ala Asn Gly Pro His His Pro Asn Pro Pro
325                 330                 335
```

FIG. 8B

```
CCC GAG AAT GTC CAG CTG GTG AAT CAA TAC GTA TCT AAA  1052
Pro Glu Asn Val Gln Leu Val Asn Gln Tyr Val Ser Lys
        340             345             350

AAC GTC ATC TCC AGT GAG CAT ATT GTT GAG AGA GAA GCA  1091
Asn Val Ile Ser Ser Glu His Ile Val Glu Arg Glu Ala
                355             360

GAG ACA TCC TTT TCC ACC AGT CAC TAT ACT TCC ACA GCC  1130
Glu Thr Ser Phe Ser Thr Ser His Tyr Thr Ser Thr Ala
    365             370             375

CAT CAC TCC ACT ACT GTC ACC CAG ACT CCT AGC CAC AGC  1169
His His Ser Thr Thr Val Thr Gln Thr Pro Ser His Ser
            380             385

TGG AGC AAC GGA CAC ACT GAA AGC ATC CTT TCC GAA AGC  1208
Trp Ser Asn Gly His Thr Glu Ser Ile Leu Ser Glu Ser
390             395             400

CAC TCT GTA ATC GTG ATG TCA TCC GTA GAA AAC AGT AGG  1247
His Ser Val Ile Val Met Ser Ser Val Glu Asn Ser Arg
        405             410             415

CAC AGC AGC CCA ACT GGG GGC CCA AGA GGA CGT CTT AAT  1286
His Ser Ser Pro Thr Gly Gly Pro Arg Gly Arg Leu Asn
                420             425

GGC ACA GGA GGC CCT CGT GAA TGT AAC AGC TTC CTC AGG  1325
Gly Thr Gly Gly Pro Arg Glu Cys Asn Ser Phe Leu Arg
    430             435             440

CAT GCC AGA GAA ACC CCT GAT TCC TAC CGA GAC TCT CCT  1364
His Ala Arg Glu Thr Pro Asp Ser Tyr Arg Asp Ser Pro
            445             450

CAT AGT GAA AGG TAT GTG TCA GCC ATG ACC ACC CCG GCT  1403
His Ser Glu Arg Tyr Val Ser Ala Met Thr Thr Pro Ala
455             460             465

CGT ATG TCA CCT GTA GAT TTC CAC ACG CCA AGC TCC CCC  1442
Arg Met Ser Pro Val Asp Phe His Thr Pro Ser Ser Pro
        470             475             480

AAA TCG CCC CCT TCG GAA ATG TCT CCA CCC GTG TCC AGC  1481
Lys Ser Pro Pro Ser Glu Met Ser Pro Pro Val Ser Ser
                485             490

ATG ACG GTG TCC ATG CCT TCC ATG GCG GTC AGC CCC TTC  1520
Met Thr Val Ser Met Pro Ser Met Ala Val Ser Pro Phe
    495             500             505
```

FIG. 8C

```
ATG GAG GAA AGA CCT CTA CTT CTC GTG ACA CCA CCA 1559
Met Glu Glu Arg Pro Leu Leu Leu Val Thr Pro Pro
    510                 515

AGG CTG CGG GAG AAG AAG TTT GAC CAT CAC CCT CAG CAG 1598
Arg Leu Arg Glu Lys Lys Phe Asp His His Pro Gln Gln
520                 525                 530

TTC AGC TCC TTC CAC CAC AAC CCC GCG CAT GAC AGT AAC 1637
Phe Ser Ser Phe His His Asn Pro Ala His Asp Ser Asn
    535                 540                 545

AGC CTC CCT GCT AGC CCC TTG AGG ATA GTG GAG GAT GAG 1676
Ser Leu Pro Ala Ser Pro Leu Arg Ile Val Glu Asp Glu
                550                 555

GAG TAT GAA ACG ACC CAA GAG TAC GAG CCA GCC CAA GAG 1715
Glu Tyr Glu Thr Thr Gln Glu Tyr Glu Pro Ala Gln Glu
560                 565                 570

CCT GTT AAG AAA CTC GCC AAT AGC CGG CGG GCC AAA AGA 1754
Pro Val Lys Lys Leu Ala Asn Ser Arg Arg Ala Lys Arg
        575                 580

ACC AAG CCC AAT GGC CAC ATT GCT AAC AGA TTG GAA GTG 1793
Thr Lys Pro Asn Gly His Ile Ala Asn Arg Leu Glu Val
585                 590                 595

GAC AGC AAC ACA AGC TCC CAG AGC AGT AAC TCA GAG AGT 1832
Asp Ser Asn Thr Ser Ser Gln Ser Ser Asn Ser Glu Ser
        600                 605                 610
```

FIG. 8D

```
GAA ACA GAA GAT GAA AGA GTA GGT GAA GAT ACG CCT TTC 1871
Glu Thr Glu Asp Glu Arg Val Gly Glu Asp Thr Pro Phe
615                 620

CTG GGC ATA CAG AAC CCC CTG GCA GCC AGT CTT GAG GCA 1910
Leu Gly Ile Gln Asn Pro Leu Ala Ala Ser Leu Glu Ala
625                 630                 635

ACA CCT GCC TTC CGC CTG GCT GAC AGC AGG ACT AAC CCA 1949
Thr Pro Ala Phe Arg Leu Ala Asp Ser Arg Thr Asn Pro
640                 645

GCA GGC CGC TTC TCG ACA CAG GAA ATC CAG GCC AGG 1988
Ala Gly Arg Phe Ser Thr Gln Glu Ile Gln Ala Arg
650                 655                 660

CTG TCT AGT GTA ATT GCT AAC CAA GAC CCT ATT GCT GTA TA 2029
Leu Ser Ser Val Ile Ala Asn Gln Asp Pro Ile Ala Val
665                 670                 675

A AACCTAAATA AACACATAGA TTCACCTGTA AAACTTTATT                2070

TTTATAATA AAGTATTCCA CCTTAAATTA AACAATTTAT TTTATTTTAG        2120

CAGTTCTGCA AATAGAAAAC AGGAAAAAAA CTTTTATAAA TTAAATATAT      2170

GTATGTAAAA ATGAAAAAAA AAAAAAAAA                             2199
```

```
AA  AGA GCC GGC GAG GAG TTC CCC GAA ACT TGT TGG AAC  38
    Arg Ala Gly Glu Glu Phe Pro Glu Thr Cys Trp Asn
    1               5                   10

TCC GGG CTC GCG CGG AGG CCA GGA GCT GAG CGG CGG CGG  77
Ser Gly Leu Ala Arg Arg Pro Gly Ala Glu Arg Arg Arg
    15              20                  25

CTG CCG GAC GAT GGG AGC GTG AGC AGG ACG GTG ATA ACC  116
Leu Pro Asp Asp Gly Ser Val Ser Arg Thr Val Ile Thr
            30                  35

TCT CCC CGA TCG GGT TGC GAG GGC GCC GGG CAG AGG CCA  155
Ser Pro Arg Ser Gly Cys Glu Gly Ala Gly Gln Arg Pro
    40                  45                  50

GGA CGC GAG CCG CCA GCG GTG GGA CCC ATC GAC GAC TTC  194
Gly Arg Glu Pro Pro Ala Val Gly Pro Ile Asp Asp Phe
            55                  60

CCG GGG CGA CAG GAG CAG CCC CGA GAG CCA GGG CGA GCG  233
Pro Gly Arg Gln Glu Gln Pro Arg Glu Pro Gly Arg Ala
65              70                  75

CCC GTT CCA GGT GGC CGG ACC GCC CGC CGC GTC CGC GCC  272
Pro Val Pro Gly Gly Arg Thr Ala Arg Arg Val Arg Ala
        80                  85                  90

GCG CTC CCT GCA GGC AAC GGG AGA CGC CCC CGC GCA GCG  311
Ala Leu Pro Ala Gly Asn Gly Arg Arg Pro Arg Ala Ala
                95                  100

CGA GCG CCT CAG CGC GGC CGC TCG CTC TCC CCC TCG AGG  350
Arg Ala Pro Gln Arg Gly Arg Ser Leu Ser Pro Ser Arg
    105                 110                 115

GAC AAA CTT TTC CCA AAC CCG ATC CGA GCC CTT GGA CCA  389
Asp Lys Leu Phe Pro Asn Pro Ile Arg Ala Leu Gly Pro
            120                 125

AAC TCG CCT GCG CCG AGA GCC GTC CGC GTA GAG CGC TCC  428
Asn Ser Pro Ala Pro Arg Ala Val Arg Val Glu Arg Ser
130             135                 140

GTC TCC GGC GAG ATG TCC GAG CGC AAA GAA GGC AGA GGC  467
Val Ser Gly Glu Met Ser Glu Arg Lys Glu Gly Arg Gly
        145                 150                 155

AAA GGG AAG GGC AAG AAG AAG GAG CGA GG  496
Lys Gly Lys Gly Lys Lys Lys Glu Arg
            160                 164
```

FIG. 11

```
GTGGCTGCGG GGCAATTGAA AAAGAGCCGG CGAGGAGTTC CCCGAAACTT   50

GTTGGAACTC CGGGCTCGCG CGGAGGCCAG GAGCTGAGCG GCGGCGGCTG  100

CCGGACGATG GGAGCGTGAG CAGGACGGTG ATAACCTCTC CCCGATCGGG  150

TTGCGAGGGC GCCGGGCAGA GGCCAGGACG CGAGCCGCCA GCGGCGGGAC  200

CCATCGACGA CTTCCCGGGG CGACAGGAGC AGCCCCGAGA GCCAGGGCGA  250

GCGCCCGTTC CAGGTGGCCG GACCGCCCGC CGCGTCCGCG CCGCGCTCCC  300

TGCAGGCAAC GGGAGACGCC CCCGCGCAGC GCGAGCGCCT CAGCGCGGCC  350

GCTCGCTCTC CCCATCGAGG GACAAACTTT TCCCAAACCC GATCCGAGCC  400

CTTGGACCAA ACTCGCCTGC GCCGAGAGCC GTCCGCGTAG AGCGCTCCGT  450
```

```
CTCCGGCGAG  ATG TCC GAG CGC AAA GAA GGC AGA GGC AAA     490
            Met Ser Glu Arg Lys Glu Gly Arg Gly Lys
             1               5                  10

GGG AAG GGC AAG AAG AAG GAG CGA GGC TCC GGC AAG AAG     529
Gly Lys Gly Lys Lys Lys Glu Arg Gly Ser Gly Lys Lys
                    15                  20

CCG GAG TCC GCG GCG GGC AGC CAG AGC CCA GCC TTG CCT     568
Pro Glu Ser Ala Ala Gly Ser Gln Ser Pro Ala Leu Pro
    25                  30                  35

CCC CAA TTG AAA GAG ATG AAA AGC CAG GAA TCG GCT GCA     607
Pro Gln Leu Lys Glu Met Lys Ser Gln Glu Ser Ala Ala
            40                  45

GGT TCC AAA CTA GTC CTT CGG TGT GAA ACC AGT TCT GAA     646
Gly Ser Lys Leu Val Leu Arg Cys Glu Thr Ser Ser Glu
50                  55                  60

TAC TCC TCT CTC AGA TTC AAG TGG TTC AAG AAT GGG AAT     685
Tyr Ser Ser Leu Arg Phe Lys Trp Phe Lys Asn Gly Asn
        65                  70                  75

GAA TTG AAT CGA AAA AAC AAA CCA CAA AAT ATC AAG ATA     724
Glu Leu Asn Arg Lys Asn Lys Pro Gln Asn Ile Lys Ile
            80                  85
```

FIG. 12A

| | | | | | | | | | | |
|---|---|---|---|---|---|---|---|---|---|---|
| CAA | AAA | AAG | CCA | GGG | AAG | TCA | GAA | CTT | CGC | ATT | AAC | AAA | 763 |
| Gln | Lys | Lys | Pro | Gly | Lys | Ser | Glu | Leu | Arg | Ile | Asn | Lys |
| | 90 | | | | 95 | | | | 100 | | |

```
CAA AAA AAG CCA GGG AAG TCA GAA CTT CGC ATT AAC AAA  763
Gln Lys Lys Pro Gly Lys Ser Glu Leu Arg Ile Asn Lys
    90              95              100

GCA TCA CTG GCT GAT TCT GGA GAG TAT ATG TGC AAA GTG  802
Ala Ser Leu Ala Asp Ser Gly Glu Tyr Met Cys Lys Val
            105             110

ATC AGC AAA TTA GGA AAT GAC AGT GCC TCT GCC AAT ATC  841
Ile Ser Lys Leu Gly Asn Asp Ser Ala Ser Ala Asn Ile
115             120             125

ACC ATC GTG GAA TCA AAC GAG ATC ATC ACT GGT ATG CCA  880
Thr Ile Val Glu Ser Asn Glu Ile Ile Thr Gly Met Pro
        130             135             140

GCC TCA ACT GAA GGA GCA TAT GTG TCT TCA GAG TCT CCC  919
Ala Ser Thr Glu Gly Ala Tyr Val Ser Ser Glu Ser Pro
                145             150

ATT AGA ATA TCA GTA TCC ACA GAA GGA GCA AAT ACT TCT  958
Ile Arg Ile Ser Val Ser Thr Glu Gly Ala Asn Thr Ser
    155             160             165

TCA TCT ACA TCT ACA TCC ACC ACT GGG ACA AGC CAT CTT  997
Ser Ser Thr Ser Thr Ser Thr Thr Gly Thr Ser His Leu
            170             175

GTA AAA TGT GCG GAG AAG GAG AAA ACT TTC TGT GTG AAT  1036
Val Lys Cys Ala Glu Lys Glu Lys Thr Phe Cys Val Asn
180             185             190

GGA GGG GAG TGC TTC ATG GTG AAA GAC CTT TCA AAC CCC  1075
Gly Gly Glu Cys Phe Met Val Lys Asp Leu Ser Asn Pro
        195             200             205

TCG AGA TAC TTG TGC AAG TGC CCA AAT GAG TTT ACT GGT  1114
Ser Arg Tyr Leu Cys Lys Cys Pro Asn Glu Phe Thr Gly
            210             215

GAT CGC TGC CAA AAC TAC GTA ATG GCC AGC TTC TAC AAG  1153
Asp Arg Cys Gln Asn Tyr Val Met Ala Ser Phe Tyr Lys
    220             225             230

GCG GAG GAG CTG TAC CAG AAG AGA GTG CTG ACC ATA ACC  1192
Ala Glu Glu Leu Tyr Gln Lys Arg Val Leu Thr Ile Thr
            235             240

GGC ATC TGC ATC GCC CTC CTT GTG GTC GGC ATC ATG TGT  1231
Gly Ile Cys Ile Ala Leu Leu Val Val Gly Ile Met Cys
245             250             255

GTG GTG GCC TAC TGC AAA ACC AAG AAA CAG CGG AAA AAG  1270
Val Val Ala Tyr Cys Lys Thr Lys Lys Gln Arg Lys Lys
260             265             270
```

FIG. 12B

```
CTG CAT GAC CGT CTT CGG CAG AGC CTT CGG TCT GAA CGA  1309
Leu His Asp Arg Leu Arg Gln Ser Leu Arg Ser Glu Arg
            275                 280

AAC AAT ATG ATG AAC ATT GCC AAT GGG CCT CAC CAT CCT  1348
Asn Asn Met Met Asn Ile Ala Asn Gly Pro His His Pro
        285                 290                 295

AAC CCA CCC CCC GAG AAT GTC CAG CTG GTG AAT CAA TAC  1387
Asn Pro Pro Pro Glu Asn Val Gln Leu Val Asn Gln Tyr
            300                 305

GTA TCT AAA AAC GTC ATC TCC AGT GAG CAT ATT GTT GAG  1426
Val Ser Lys Asn Val Ile Ser Ser Glu His Ile Val Glu
310             315                 320

AGA GAA GCA GAG ACA TCC TTT TCC ACC AGT CAC TAT ACT  1465
Arg Glu Ala Glu Thr Ser Phe Ser Thr Ser His Tyr Thr
        325                 330                 335

TCC ACA GCC CAT CAC TCC ACT ACT GTC ACC CAG ACT CCT  1504
Ser Thr Ala His His Ser Thr Thr Val Thr Gln Thr Pro
            340                 345

AGC CAC AGC TGG AGC AAC GGA CAC ACT GAA AGC ATC CTT  1543
Ser His Ser Trp Ser Asn Gly His Thr Glu Ser Ile Leu
        350                 355                 360

TCC GAA AGC CAC TCT GTA ATC GTG ATG TCA TCC GTA GAA  1582
Ser Glu Ser His Ser Val Ile Val Met Ser Ser Val Glu
            365                 370

AAC AGT AGG CAC AGC AGC CCA ACT GGG GGC CCA AGA GGA  1621
Asn Ser Arg His Ser Ser Pro Thr Gly Gly Pro Arg Gly
375             380                 385

CGT CTT AAT GGC ACA GGA GGC CCT CGT GAA TGT AAC AGC  1660
Arg Leu Asn Gly Thr Gly Gly Pro Arg Glu Cys Asn Ser
        390                 395                 400

TTC CTC AGG CAT GCC AGA GAA ACC CCT GAT TCC TAC CGA  1699
Phe Leu Arg His Ala Arg Glu Thr Pro Asp Ser Tyr Arg
            405                 410

GAC TCT CCT CAT AGT GAA AGG TAT GTG TCA GCC ATG ACC  1738
Asp Ser Pro His Ser Glu Arg Tyr Val Ser Ala Met Thr
        415                 420                 425

ACC CCG GCT CGT ATG TCA CCT GTA GAT TTC CAC ACG CCA  1777
Thr Pro Ala Arg Met Ser Pro Val Asp Phe His Thr Pro
            430                 435

AGC TCC CCC AAA TCG CCC CCT TCG GAA ATG TCT CCA CCC  1816
Ser Ser Pro Lys Ser Pro Pro Ser Glu Met Ser Pro Pro
440             445                 450
```

FIG. 12C

```
GTG TCC AGC ATG ACG GTG TCC AAG CCT TCC ATG GCG GTC   1855
Val Ser Ser Met Thr Val Ser Lys Pro Ser Met Ala Val
        455                 460                 465

AGC CCC TTC ATG GAA GAA GAG AGA CCT CTA CTT CTC GTG   1894
Ser Pro Phe Met Glu Glu Glu Arg Pro Leu Leu Leu Val
                470                 475

ACA CCA CCA AGG CTG CGG GAG AAG AAG TTT GAC CAT CAC   1933
Thr Pro Pro Arg Leu Arg Glu Lys Lys Phe Asp His His
        480                 485                 490

CCT CAG CAG TTC AGC TCC TTC CAC CAC AAC CCC GCG CAT   1972
Pro Gln Gln Phe Ser Ser Phe His His Asn Pro Ala His
                495                 500

GAC AGT AAC AGC CTC CCT GCT AGC CCC TTG AGG ATA GTG   2011
Asp Ser Asn Ser Leu Pro Ala Ser Pro Leu Arg Ile Val
505                 510                 515

GAG GAT GAG GAG TAT GAA ACG ACC CAA GAG TAC GAG CCA   2050
Glu Asp Glu Glu Tyr Glu Thr Thr Gln Glu Tyr Glu Pro
            520                 525                 530

GCC CAA GAG CCT GTT AAG AAA CTC GCC AAT AGC CGG CGG   2089
Ala Gln Glu Pro Val Lys Lys Leu Ala Asn Ser Arg Arg
                535                 540

GCC AAA AGA ACC AAG CCC AAT GGC CAC ATT GCT AAC AGA   2128
Ala Lys Arg Thr Lys Pro Asn Gly His Ile Ala Asn Arg
        545                 550                 555

TTG GAA GTG GAC AGC AAC ACA AGC TCC CAG AGC AGT AAC   2167
Leu Glu Val Asp Ser Asn Thr Ser Ser Gln Ser Ser Asn
                560                 565

TCA GAG AGT GAA ACA GAA GAT GAA AGA GTA GGT GAA GAT   2206
Ser Glu Ser Glu Thr Glu Asp Glu Arg Val Gly Glu Asp
570                 575                 580

ACG CCT TTC CTG GGC ATA CAG AAC CCC CTG GCA GCC AGT   2245
Thr Pro Phe Leu Gly Ile Gln Asn Pro Leu Ala Ala Ser
            585                 590                 595

CTT GAG GCA ACA CCT GCC TTC CGC CTG GCT GAC AGC AGG   2284
Leu Glu Ala Thr Pro Ala Phe Arg Leu Ala Asp Ser Arg
                600                 605

ACT AAC CCA GCA GGC CGC TTC TCG ACA CAG GAA GAA ATC   2323
Thr Asn Pro Ala Gly Arg Phe Ser Thr Gln Glu Glu Ile
        610                 615                 620

CAG GCC AGG CTG TCT AGT GTA ATT GCT AAC CAA GAC CCT   2362
Gln Ala Arg Leu Ser Ser Val Ile Ala Asn Gln Asp Pro
            625                 630
```

FIG. 12D

```
ATT GCT GTA TAAAACCTA AATAAACACA TAGATTCACC TGTAAAACTT 2410
Ile Ala Val
635     637

TATTTTATAT AATAAAGTAT TCCACCTTAA ATTAAACAAT TTATTTTATT 2460

TTAGCAGTTC TGCAAATAAA AAAAAAAAAA 2490
```

FIG. 12E

GCGCCTGCCT CCAACCTGCG GGCGGGAGGT GGGTGGCTGC GGGGCAATTG 50

AAAAAGAGCC GGCGAGGAGT TCCCCGAAAC TTGTTGGAAC TCCGGGCTCG 100

CGCGGAGGCC AGGAGCTGAG CGGCGGCGGC TGCCGGACGA TGGGAGCGTG 150

AGCAGGACGG TGATAACCTC TCCCCGATCG GGTTGCGAGG GCGCCGGGCA 200

GAGGCCAGGA CGCGAGCCGC CAGCGGCGGG ACCCATCGAC GACTTCCCGG 250

GGCGACAGGA GCAGCCCCGA GAGCCAGGGC GAGCGCCCGT TCCAGGTGGC 300

CGGACCGCCC GCCGCGTCCG CGCCGCGCTC CCTGCAGGCA ACGGGAGACG 350

CCCCCGCGCA GCGCGAGCGC CTCAGCGCGG CCGCTCGCTC TCCCCATCGA 400

GGGACAAACT TTTCCCAAAC CCGATCCGAG CCCTTGGACC AAACTCGCCT 450

GCGCCGAGAG CCGTCCGCGT AGAGCGCTCC GTCTCCGGCG AG  ATG 495
                                                Met
                                                 1

TCC GAG CGC AAA GAA GGC AGA GGC AAA GGG AAG GGC AAG 534
Ser Glu Arg Lys Glu Gly Arg Gly Lys Gly Lys Gly Lys
            5                       10

AAG AAG GAG CGA GGC TCC GGC AAG AAG CCG GAG TCC GCG 573
Lys Lys Glu Arg Gly Ser Gly Lys Lys Pro Glu Ser Ala
 15              20                       25

GCG GGC AGC CAG AGC CCA GCC TTG CCT CCC CAA TTG AAA 612
Ala Gly Ser Gln Ser Pro Ala Leu Pro Pro Gln Leu Lys
             30                  35                40

GAG ATG AAA AGC CAG GAA TCG GCT GCA GGT TCC AAA CTA 651
Glu Met Lys Ser Gln Glu Ser Ala Ala Gly Ser Lys Leu
                 45                  50

GTC CTT CGG TGT GAA ACC AGT TCT GAA TAC TCC TCT CTC 690
Val Leu Arg Cys Glu Thr Ser Ser Glu Tyr Ser Ser Leu
 55                      60                      65

AGA TTC AAG TGG TTC AAG AAT GGG AAT GAA TTG AAT CGA 729
Arg Phe Lys Trp Phe Lys Asn Gly Asn Glu Leu Asn Arg
         70                      75

FIG. 13A

```
AAA AAC AAA CCA CAA AAT ATC AAG ATA CAA AAA AAG CCA 768
Lys Asn Lys Pro Gln Asn Ile Lys Ile Gln Lys Lys Pro
 80              85                  90

GGG AAG TCA GAA CTT CGC ATT AAC AAA GCA TCA CTG GCT 807
Gly Lys Ser Glu Leu Arg Ile Asn Lys Ala Ser Leu Ala
         95              100                 105

GAT TCT GGA GAG TAT ATG TGC AAA GTG ATC AGC AAA TTA 846
Asp Ser Gly Glu Tyr Met Cys Lys Val Ile Ser Lys Leu
                 110             115

GGA AAT GAC AGT GCC TCT GCC AAT ATC ACC ATC GTG GAA 885
Gly Asn Asp Ser Ala Ser Ala Asn Ile Thr Ile Val Glu
    120             125                 130

TCA AAC GAG ATC ATC ACT GGT ATG CCA GCC TCA ACT GAA 924
Ser Asn Glu Ile Ile Thr Gly Met Pro Ala Ser Thr Glu
             135                 140

GGA GCA TAT GTG TCT TCA GAG TCT CCC ATT AGA ATA TCA 963
Gly Ala Tyr Val Ser Ser Glu Ser Pro Ile Arg Ile Ser
145             150                 155

GTA TCC ACA GAA GGA GCA AAT ACT TCT TCA TCT ACA TCT 1002
Val Ser Thr Glu Gly Ala Asn Thr Ser Ser Ser Thr Ser
        160             165                 170

ACA TCC ACC ACT GGG ACA AGC CAT CTT GTA AAA TGT GCG 1041
Thr Ser Thr Thr Gly Thr Ser His Leu Val Lys Cys Ala
                175             180

GAG AAG GAG AAA ACT TTC TGT GTG AAT GGA GGG GAG TGC 1080
Glu Lys Glu Lys Thr Phe Cys Val Asn Gly Gly Glu Cys
    185             190                 195

TTC ATG GTG AAA GAC CTT TCA AAC CCC TCG AGA TAC TTG 1119
Phe Met Val Lys Asp Leu Ser Asn Pro Ser Arg Tyr Leu
            200             205

TGC AAG TGC CCA AAT GAG TTT ACT GGT GAT CGC TGC CAA 1158
Cys Lys Cys Pro Asn Glu Phe Thr Gly Asp Arg Cys Gln
210             215                 220

AAC TAC GTA ATG GCC AGC TTC TAC AGT ACG TCC ACT CCC 1197
Asn Tyr Val Met Ala Ser Phe Tyr Ser Thr Ser Thr Pro
        225             230                 235

TTT CTG TCT CTG CCT GAA TAGGA GCATGCTCAG TTGGTGCTGC 1240
Phe Leu Ser Leu Pro Glu
                240 241

TTTCTTGTTG CTGCATCTCC CCTCAGATTC CACCTAGAGC TAGATGTGTC 1290
```

FIG. 13B

```
TTACCAGATC TAATATTGAC TGCCTCTGCC TGTCGCATGA GAACATTAAC 1340

AAAAGCAATT GTATTACTTC CTCTGTTCGC GACTAGTTGG CTCTGAGATA 1390

CTAATAGGTG TGTGAGGCTC CGGATGTTTC TGGAATTGAT ATTGAATGAT 1440

GTGATACAAA TTGATAGTCA ATATCAAGCA GTGAAATATG ATAATAAAGG 1490

CATTTCAAAG TCTCACTTTT ATTGATAAAA TAAAAATCAT TCTACTGAAC 1540

AGTCCATCTT CTTTATACAA TGACCACATC CTGAAAAGGG TGTTGCTAAG 1590

CTGTAACCGA TATGCACTTG AAATGATGGT AAGTTAATTT TGATTCAGAA 1640

TGTGTTATTT GTCACAAATA AACATAATAA AAGGAGTTCA GATGTTTTTC 1690

TTCATTAACC AAAAAAAAAA AAAAA 1715
```

FIG. 13C

```
GAGGCGCCTG CCTCCAACCT GCGGGCGGGA GGTGGGTGGC TGCGGGGCAA  50

TTGAAAAAGA GCCGGCGAGG AGTTCCCCGA AACTTGTTGG AACTCCGGGC 100

TCGCGCGGAG GCCAGGAGCT GAGCGGCGGC GGCTGCCGGA CGATGGGAGC 150

GTGAGCAGGA CGGTGATAAC CTCTCCCCGA TCGGGTTGCG AGGGCGCCGG 200

GCAGAGGCCA GGACGCGAGC CGCCAGCGGC GGGACCCATC GACGACTTCC 250

CGGGGCGACA GGAGCAGCCC CGAGAGCCAG GGCGAGCGCC CGTTCCAGGT 300

GGCCGGACCG CCCGCCGCGT CCGCGCCGCG CTCCCTGCAG GCAACGGGAG 350

ACGCCCCCGC GCAGCGCGAG CGCCTCAGCG CGGCCGCTCG CTCTCCCCAT 400

CGAGGGACAA ACTTTTCCCA AACCCGATCC GAGCCCTTGG ACCAAACTCG 450

CCTGCGCCGA GAGCCGTCCG CGTAGAGCGC TCCGTCTCCG GCGAG    AT 497
                                                     Met
                                                      1
```

```
G TCC GAG CGC AAA GAA GGC AGA GGC AAA GGG AAG GGC AAG 537
  Ser Glu Arg Lys Glu Gly Arg Gly Lys Gly Lys Gly Lys
            5                  10

AAG AAG GAG CGA GGC TCC GGC AAG AAG CCG GAG TCC GCG 576
Lys Lys Glu Arg Gly Ser Gly Lys Lys Pro Glu Ser Ala
 15              20                  25

GCG GGC AGC CAG AGC CCA GCC TTG CCT CCC CAA TTG AAA 615
Ala Gly Ser Gln Ser Pro Ala Leu Pro Pro Gln Leu Lys
         30                  35                  40

GAG ATG AAA AGC CAG GAA TCG GCT GCA GGT TCC AAA CTA 654
Glu Met Lys Ser Gln Glu Ser Ala Ala Gly Ser Lys Leu
             45                  50

GTC CTT CGG TGT GAA ACC AGT TCT GAA TAC TCC TCT CTC 693
Val Leu Arg Cys Glu Thr Ser Ser Glu Tyr Ser Ser Leu
 55                  60                  65

AGA TTC AAG TGG TTC AAG AAT GGG AAT GAA TTG AAT CGA 732
Arg Phe Lys Trp Phe Lys Asn Gly Asn Glu Leu Asn Arg
             70                  75
```

FIG. 14A

```
AAA AAC AAA CCA CAA AAT ATC AAG ATA CAA AAA AAG CCA  771
Lys Asn Lys Pro Gln Asn Ile Lys Ile Gln Lys Lys Pro
 80              85                  90

GGG AAG TCA GAA CTT CGC ATT AAC AAA GCA TCA CTG GCT  810
Gly Lys Ser Glu Leu Arg Ile Asn Lys Ala Ser Leu Ala
         95                 100                 105

GAT TCT GGA GAG TAT ATG TGC AAA GTG ATC AGC AAA TTA  849
Asp Ser Gly Glu Tyr Met Cys Lys Val Ile Ser Lys Leu
                     110             115

GGA AAT GAC AGT GCC TCT GCC AAT ATC ACC ATC GTG GAA  888
Gly Asn Asp Ser Ala Ser Ala Asn Ile Thr Ile Val Glu
 120             125                 130

TCA AAC GAG ATC ATC ACT GGT ATG CCA GCC TCA ACT GAA  927
Ser Asn Glu Ile Ile Thr Gly Met Pro Ala Ser Thr Glu
         135                 140

GGA GCA TAT GTG TCT TCA GAG TCT CCC ATT AGA ATA TCA  966
Gly Ala Tyr Val Ser Ser Glu Ser Pro Ile Arg Ile Ser
145                  150                 155

GTA TCC ACA GAA GGA GCA AAT ACT TCT TCA TCT ACA TCT 1005
Val Ser Thr Glu Gly Ala Asn Thr Ser Ser Ser Thr Ser
         160                 165                 170

ACA TCC ACC ACT GGG ACA AGC CAT CTT GTA AAA TGT GCG 1044
Thr Ser Thr Thr Gly Thr Ser His Leu Val Lys Cys Ala
                     175             180

GAG AAG GAG AAA ACT TTC TGT GTG AAT GGA GGG GAG TGC 1083
Glu Lys Glu Lys Thr Phe Cys Val Asn Gly Gly Glu Cys
 185                 190                 195

TTC ATG GTG AAA GAC CTT TCA AAC CCC TCG AGA TAC TTG 1122
Phe Met Val Lys Asp Leu Ser Asn Pro Ser Arg Tyr Leu
         200                 205

TGC AAG TGC CCA AAT GAG TTT ACT GGT GAT CGC TGC CAA 1161
Cys Lys Cys Pro Asn Glu Phe Thr Gly Asp Arg Cys Gln
210                  215                 220

AAC TAC GTA ATG GCC AGC TTC TAC AAG GCG GAG GAG CTG 1200
Asn Tyr Val Met Ala Ser Phe Tyr Lys Ala Glu Glu Leu
         225                 230                 235

TAC CAG AAG AGA GTG CTG ACC ATA ACC GGC ATC TGC ATC 1239
Tyr Gln Lys Arg Val Leu Thr Ile Thr Gly Ile Cys Ile
                     240             245

GCC CTC CTT GTG GTC GGC ATC ATG TGT GTG GTG GCC TAC 1278
Ala Leu Leu Val Val Gly Ile Met Cys Val Val Ala Tyr
 250   FIG. 14B      255                 260
```

```
TGC AAA ACC AAG AAA CAG CGG AAA AAG CTG CAT GAC CGT  1317
Cys Lys Thr Lys Lys Gln Arg Lys Lys Leu His Asp Arg
            265             270

CTT CGG CAG AGC CTT CGG TCT GAA CGA AAC AAT ATG ATG  1356
Leu Arg Gln Ser Leu Arg Ser Glu Arg Asn Asn Met Met
275             280             285

AAC ATT GCC AAT GGG CCT CAC CAT CCT AAC CCA CCC CCC  1395
Asn Ile Ala Asn Gly Pro His His Pro Asn Pro Pro Pro
        290             295             300

GAG AAT GTC CAG CTG GTG AAT CAA TAC GTA TCT AAA AAC  1434
Glu Asn Val Gln Leu Val Asn Gln Tyr Val Ser Lys Asn
                305             310

GTC ATC TCC AGT GAG CAT ATT GTT GAG AGA GAA GCA GAG  1473
Val Ile Ser Ser Glu His Ile Val Glu Arg Glu Ala Glu
        315             320             325

ACA TCC TTT TCC ACC AGT CAC TAT ACT TCC ACA GCC CAT  1512
Thr Ser Phe Ser Thr Ser His Tyr Thr Ser Thr Ala His
            330             335

CAC TCC ACT ACT GTC ACC CAG ACT CCT AGC CAC AGC TGG  1551
His Ser Thr Thr Val Thr Gln Thr Pro Ser His Ser Trp
340             345             350

AGC AAC GGA CAC ACT GAA AGC ATC CTT TCC GAA AGC CAC  1590
Ser Asn Gly His Thr Glu Ser Ile Leu Ser Glu Ser His
        355             360             365

TCT GTA ATC GTG ATG TCA TCC GTA GAA AAC AGT AGG CAC  1629
Ser Val Ile Val Met Ser Ser Val Glu Asn Ser Arg His
                370             375

AGC AGC CCA ACT GGG GGC CCA AGA GGA CGT CTT AAT GGC  1668
Ser Ser Pro Thr Gly Gly Pro Arg Gly Arg Leu Asn Gly
        380             385             390

ACA GGA GGC CCT CGT GAA TGT AAC AGC TTC CTC AGG CAT  1707
Thr Gly Gly Pro Arg Glu Cys Asn Ser Phe Leu Arg His
            395             400

GCC AGA GAA ACC CCT GAT TCC TAC CGA GAC TCT CCT CAT  1746
Ala Arg Glu Thr Pro Asp Ser Tyr Arg Asp Ser Pro His
405             410             415

AGT GAA AGG TAAAA CCGAAGGCAA AGCTACTGCA GAGGAGAAAC  1790
Ser Glu Arg
        420
```

FIG. 14C

```
TCAGTCAGAG AATCCCTGTG AGCACCTGCG GTCTCACCTC AGGAAATCTA 1840

CTCTAATCAG AATAAGGGGC GGCAGTTACC TGTTCTAGGA GTGCTCCTAG 1890

TTGATGAAGT CATCTCTTTG TTTGACGGAA CTTATTTCTT CTGAGCTTCT 1940

CTCGTCGTCC CAGTGACTGA CAGGCAACAG ACTCTTAAAG AGCTGGGATG 1990

CTTTGATGCG GAAGGTGCAG CACATGGAGT TTCCAGCTCT GGCCATGGGC 2040

TCAGACCCAC TCGGGGTCTC AGTGTCCTCA GTTGTAACAT TAGAGAGATG 2090

GCATCAATGC TTGATAAGGA CCCTTCTATA ATTCCAATTG CCAGTTATCC 2140

AAACTCTGAT TCGGTGGTCG AGCTGGCCTC GTGTTCTTAT CTGCTAACCC 2190

TGTCTTACCT TCCAGCCTCA GTTAAGTCAA ATCAAGGGCT ATGTCATTGC 2240

TGAATGTCAT GGGGGGCAAC TGCTTGCCCT CCACCCTATA GTATCTATTT 2290

TATGAAATTC CAAGAAGGGA TGAATAAATA AATCTCTTGG ATGCTGCGTC 2340

TGGCAGTCTT CACGGGTGGT TTTCAAAGCA GAAAAAAAAA AAAAAAAAA 2390

AAAAAAAAAA AAAAAAAAAA AAAAAAAAAA AAAAAAAAA A 2431
```

FIG. 14D

```
  1  MSERKEGRGKGKKKERGSGKKPESAAGSQSPALPPRLKEMKSQESAAG
  1  MSERKEGRGKGKKKERGSGKKPESAAGSQSPALPPQLKEMKSQESAAG
  1  MSERKEGRGKGKKKERGSGKKPESAAGSQSPALPPQLKEMKSQESAAG
  1  MSERKEGRGKGKKKERGSGKKPESAAGSQSPALPPQLKEMKSQESAAG
  1  MSERKEGRGKGKKKERGSGKKPESAAGSQSPALPPQLKEMKSQESAAG

51  SKLVLRCETSSEYSSLRFKWFKNGNELNRKNKPQNIKIQKKPGKSELRIN
 51  SKLVLRCETSSEYSSLRFKWFKNGNELNRKNKPQNIKIQKKPGKSELRIN
 51  SKLVLRCETSSEYSSLRFKWFKNGNELNRKNKPQNIKIQKKPGKSELRIN
 51  SKLVLRCETSSEYSSLRFKWFKNGNELNRKNKPQNIKIQKKPGKSELRIN
 51  SKLVLRCETSSEYSSLRFKWFKNGNELNRKNKPQNIKIQKKPGKSELRIN

101  KASLADSGEYMCKVISKLGNDSASANITIVESNEIITGMPASTEGAYVSS
101  KASLADSGEYMCKVISKLGNDSASANITIVESNEIITGMPASTEGAYVSS
101  KASLADSGEYMCKVISKLGNDSASANITIVESNEIITGMPASTEGAYVSS
101  KASLADSGEYMCKVISKLGNDSASANITIVESNEIITGMPASTEGAYVSS
101  KASLADSGEYMCKVISKLGNDSASANITIVESNEIITGMPASTEGAYVSS

151  ESPIRISVSTEGANTSSSTSTTGTSHLVKCAEKEKTFCVNGGECFMVK
151  ESPIRISVSTEGANTSSSTSTTGTSHLVKCAEKEKTFCVNGGECFMVK
151  ESPIRISVSTEGANTSSSTSTTGTSHLVKCAEKEKTFCVNGGECFMVK
151  ESPIRISVSTEGANTSSSTSTTGTSHLVKCAEKEKTFCVNGGECFMVK
151  ESPIRISVSTEGANTSSSTSTTGTSHLVKCAEKEKTFCVNGGECFMVK
```

```
 16 201 DLSNPSRYLCKCQPGFTGARCTENVPMKVQNQ------EKAEEELYQKRVLT
 11 201 DLSNPSRYLCKCQPNEFTGDRCQNYVMASFYK-------AEEELYQKRVLT
 76 201 DLSNPSRYLCKCQPNEFTGDRCQNYVMASFYK-------AEEELYQKRVLT
 84 201 DLSNPSRYLCKCQPNEFTGDRCQNYVMASFYKHLGIEFMEAEEELYQKRVLT
 78 201 DLSNPSRYLCKCQPNEFTGDRCQNYVMASFYK-------STSTPFLSLPE 16 246 ITGICIALLVVGIMCVVAYCKTKKQRKKLHDRLRQSLRSERNNMMNIANG
 11 251 ITGICIALLVVGIMCVVAYCKTKKQRKKLHDRLRQSLRSERNNMMNIANG
 76 243 ITGICIALLVVGIMCVVAYCKTKKQRKKLHDRLRQSLRSERNNMMNIANG
 84 243 ITGICIALLVVGIMCVVAYCKTKKQRKKLHDRLRQSLRSERNNMMNIANG 16 296 PHHPNPPPENVQLVNQYVSKNVISSEHIVEREAETSFSTSHYTSTAHHST
 11 301 PHHPNPPPENVQLVNQYVSKNVISSEHIVEREAETSFSTSHYTSTAHHST
 76 293 PHHPNPPPENVQLVNQYVSKNVISSEHIVEREAETSFSTSHYTSTAHHST
 84 293 PHHPNPPPENVQLVNQYVSKNVISSEHIVEREAETSFSTSHYTSTAHHST 16 346 TVTQTPSHSWSNGHTESILSESHSVIVMSSVENSRHSSPTGGPRGRLNGT
 11 351 TVTQTPSHSWSNGHTESILSESHSVIVMSSVENSRHSSPTGGPRGRLNGT
 76 343 TVTQTPSHSWSNGHTESILSESHSVIVMSSVENSRHSSPTGGPRGRLNGT
 84 343 TVTQTPSHSWSNGHTESILSESHSVIVMSSVENSRHSSPTGGPRGRLNGT
```

| 16 | 396 | GGPRECNSFLRHARETPDSYRDSPHSERYVSAMTTPARMSPVDFHTPSSP |
| 11 | 401 | GGPRECNSFLRHARETPDSYRDSPHSERYVSAMTTPARMSPVDFHTPSSP |
| 76 | 393 | GGPRECNSFLRHARETPDSYRDSPHSERYVSAMTTPARMSPVDFHTPSSP |
| 84 | 393 | GGPRECNSFLRHARETPDSYRDSPHSER--------------------- |

| 16 | 446 | KSPPSEMSPPVSSMTVSMPSMAVSPFMEEERPLLLVTPPRLREKKFDHHP |
| 11 | 451 | KSPPSEMSPPVSSMTVSMPSMAVSPFMEEERPLLLVTPPRLREKKFDHHP |
| 76 | 443 | KSPPSEMSPPVSSMTVSKPSMAVSPFMEEERPLLLVTPPRLREKKFDHHP |

| 16 | 496 | QQFSSFHHNPAHDSNSLPASPLRIVEDEEYETTQEYEPAQEPVKKLANSR |
| 11 | 501 | QQFSSFHHNPAHDSNSLPASPLRIVEDEEYETTQEYEPAQEPVKKLANSR |
| 76 | 493 | QQFSSFHHNPAHDSNSLPASPLRIVEDEEYETTQEYEPAQEPVKKLANSR |

| 16 | 546 | RAKRTKPNGHIANRLEVDSNTSSQSSNSESETEDERVGEDTPFLGIQNPL |
| 11 | 551 | RAKRTKPNGHIANRLEVDSNTSSQSSNSESETEDERVGEDTPFLGIQNPL |
| 76 | 543 | RAKRTKPNGHIANRLEVDSNTSSQSSNSESETEDERVGEDTPFLGIQNPL |

| 16 | 596 | AASLEATPAFRLADSRTNPAGRFSTQEEIQ-------------------- |
| 11 | 601 | AASLEATPAFRLADSRTNPAGRFSTQEEIQARLSSVIANQDPIAV |
| 76 | 593 | AASLEATPAFRLADSRTNPAGRFSTQEEIQARLSSVIANQDPIAV |

FIG. 15C

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 6 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

CNCAAT      6

( 2 ) INFORMATION FOR SEQ ID NO:2:

( i ) SEQUENCE CHARACTERISTICS:
        ( A ) LENGTH: 6 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

AATAAA      6

( 2 ) INFORMATION FOR SEQ ID NO:3:

( i ) SEQUENCE CHARACTERISTICS:
        ( A ) LENGTH: 24 amino acids
        ( B ) TYPE: amino acid
        ( D ) TOPOLOGY: linear ( x i ) SEQUENCE DESCRIPTION: SEQ ID NO:3:

```
Ala  Ala  Glu  Lys  Glu  Lys  Thr  Phe  Cys  Val  Asn  Gly  Gly  Glu  Xaa
 1              5                        10                           15
Phe  Met  Val  Lys  Asp  Leu  Xaa  Asn  Pro
                20                  24
```

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( D ) TOPOLOGY: linear ( x i ) SEQUENCE DESCRIPTION: SEQ ID NO:4:

```
Xaa  Glu  Xaa  Lys  Glu  Gly  Arg  Gly  Lys  Gly  Lys  Gly  Lys  Lys  Lys
 1              5                        10                           15
Glu  Xaa  Gly  Xaa  Gly  Lys
                20   21
```

( 2 ) INFORMATION FOR SEQ ID NO:5:

( i ) SEQUENCE CHARACTERISTICS:
 ( A ) LENGTH: 13 amino acids
 ( B ) TYPE: amino acid
 ( D ) TOPOLOGY: linear ( x i ) SEQUENCE DESCRIPTION: SEQ ID NO:5:

| Ala | Glu | Lys | Glu | Lys | Thr | Phe | Xaa | Val | Asn | Gly | Gly | Glu |
|---|---|---|---|---|---|---|---|---|---|---|---|---|
| 1 | | | | 5 | | | | | 10 | | | 13 |

( 2 ) INFORMATION FOR SEQ ID NO:6:

( i ) SEQUENCE CHARACTERISTICS:
  ( A ) LENGTH: 42 bases
  ( B ) TYPE: nucleic acid
  ( C ) STRANDEDNESS: single
  ( D ) TOPOLOGY: linear ( x i ) SEQUENCE DESCRIPTION: SEQ ID NO:6:

GCTGAGAAGG AGAAGACCTT CTGTCGTGAA TCGGACGGCG AG                               42

( 2 ) INFORMATION FOR SEQ ID NO:7:

( i ) SEQUENCE CHARACTERISTICS:
  ( A ) LENGTH: 2199 bases
  ( B ) TYPE: nucleic acid
  ( C ) STRANDEDNESS: single
  ( D ) TOPOLOGY: linear ( x i ) SEQUENCE DESCRIPTION: SEQ ID NO:7:

```
GG  GAC  AAA  CTT  TTC  CCA  AAC  CCG  ATC  CGA  GCC  CTT  GGA            38
    Asp  Lys  Leu  Phe  Pro  Asn  Pro  Ile  Arg  Ala  Leu  Gly
    1              5                        10

CCA  AAC  TCG  CCT  GCG  CCG  AGA  GCC  GTC  CGC  GTA  GAG  CGC            77
Pro  Asn  Ser  Pro  Ala  Pro  Arg  Ala  Val  Arg  Val  Glu  Arg
          15                  20                            25

TCC  GTC  TCC  GGC  GAG  ATG  TCC  GAG  CGC  AAA  GAA  GGC  AGA           116
Ser  Val  Ser  Gly  Glu  Met  Ser  Glu  Arg  Lys  Glu  Gly  Arg
                    30                       35

GGC  AAA  GGG  AAG  GGC  AAG  AAG  AAG  GAG  CGA  GGC  TCC  GGC           155
Gly  Lys  Gly  Lys  Gly  Lys  Lys  Lys  Glu  Arg  Gly  Ser  Gly
     40                       45                       50

AAG  AAG  CCG  GAG  TCC  GCG  GCG  GGC  AGC  CAG  AGC  CCA  GCC           194
Lys  Lys  Pro  Glu  Ser  Ala  Ala  Gly  Ser  Gln  Ser  Pro  Ala
               55                       60

TTG  CCT  CCC  CAA  TTG  AAA  GAG  ATG  AAA  AGC  CAG  GAA  TCG           233
Leu  Pro  Pro  Gln  Leu  Lys  Glu  Met  Lys  Ser  Gln  Glu  Ser
65                       70                       75

GCT  GCA  GGT  TCC  AAA  CTA  GTC  CTT  CGG  TGT  GAA  ACC  AGT           272
Ala  Ala  Gly  Ser  Lys  Leu  Val  Leu  Arg  Cys  Glu  Thr  Ser
               80                       85                       90

TCT  GAA  TAC  TCC  TCT  CTC  AGA  TTC  AAG  TGG  TTC  AAG  AAT           311
Ser  Glu  Tyr  Ser  Ser  Leu  Arg  Phe  Lys  Trp  Phe  Lys  Asn
                    95                       100

GGG  AAT  GAA  TTG  AAT  CGA  AAA  AAC  AAA  CCA  CAA  AAT  ATC           350
Gly  Asn  Glu  Leu  Asn  Arg  Lys  Asn  Lys  Pro  Gln  Asn  Ile
     105                      110                      115

AAG  ATA  CAA  AAA  AAG  CCA  GGG  AAG  TCA  GAA  CTT  CGC  ATT           389
Lys  Ile  Gln  Lys  Lys  Pro  Gly  Lys  Ser  Glu  Leu  Arg  Ile
               120                      125

AAC  AAA  GCA  TCA  CTG  GCT  GAT  TCT  GGA  GAG  TAT  ATG  TGC           428
Asn  Lys  Ala  Ser  Leu  Ala  Asp  Ser  Gly  Glu  Tyr  Met  Cys
130                      135                      140

AAA  GTG  ATC  AGC  AAA  TTA  GGA  AAT  GAC  AGT  GCC  TCT  GCC           467
```

|   |   |   |   |   |   |   |   |   |   |   |   |   |
|---|---|---|---|---|---|---|---|---|---|---|---|---|
| Lys | Val | Ile | Ser | Lys | Leu | Gly | Asn | Asp | Ser | Ala | Ser | Ala |
|  | 145 |  |  |  | 150 |  |  |  |  |  |  | 155 |

| AAT | ATC | ACC | ATC | GTG | GAA | TCA | AAC | GAG | ATC | ATC | ACT | GGT | 506 |
|---|---|---|---|---|---|---|---|---|---|---|---|---|---|
| Asn | Ile | Thr | Ile | Val | Glu | Ser | Asn | Glu | Ile | Ile | Thr | Gly |  |
|  |  |  |  | 160 |  |  |  |  | 165 |  |  |  |  |

| ATG | CCA | GCC | TCA | ACT | GAA | GGA | GCA | TAT | GTG | TCT | TCA | GAG | 545 |
|---|---|---|---|---|---|---|---|---|---|---|---|---|---|
| Met | Pro | Ala | Ser | Thr | Glu | Gly | Ala | Tyr | Val | Ser | Ser | Glu |  |
|  | 170 |  |  |  |  | 175 |  |  |  |  | 180 |  |  |

| TCT | CCC | ATT | AGA | ATA | TCA | GTA | TCC | ACA | GAA | GGA | GCA | AAT | 584 |
|---|---|---|---|---|---|---|---|---|---|---|---|---|---|
| Ser | Pro | Ile | Arg | Ile | Ser | Val | Ser | Thr | Glu | Gly | Ala | Asn |  |
|  |  |  | 185 |  |  |  |  | 190 |  |  |  |  |  |

| ACT | TCT | TCA | TCT | ACA | TCT | ACA | TCC | ACC | ACT | GGG | ACA | AGC | 623 |
|---|---|---|---|---|---|---|---|---|---|---|---|---|---|
| Thr | Ser | Ser | Ser | Thr | Ser | Thr | Ser | Thr | Thr | Gly | Thr | Ser |  |
| 195 |  |  |  |  | 200 |  |  |  |  | 205 |  |  |  |

| CAT | CTT | GTA | AAA | TGT | GCG | GAG | AAG | GAG | AAA | ACT | TTC | TGT | 662 |
|---|---|---|---|---|---|---|---|---|---|---|---|---|---|
| His | Leu | Val | Lys | Cys | Ala | Glu | Lys | Glu | Lys | Thr | Phe | Cys |  |
|  |  | 210 |  |  |  |  | 215 |  |  |  |  | 220 |  |

| GTG | AAT | GGA | GGG | GAG | TGC | TTC | ATG | GTG | AAA | GAC | CTT | TCA | 701 |
|---|---|---|---|---|---|---|---|---|---|---|---|---|---|
| Val | Asn | Gly | Gly | Glu | Cys | Phe | Met | Val | Lys | Asp | Leu | Ser |  |
|  |  |  |  | 225 |  |  |  |  | 230 |  |  |  |  |

| AAC | CCC | TCG | AGA | TAC | TTG | TGC | AAG | TGC | CCA | AAT | GAG | TTT | 740 |
|---|---|---|---|---|---|---|---|---|---|---|---|---|---|
| Asn | Pro | Ser | Arg | Tyr | Leu | Cys | Lys | Cys | Pro | Asn | Glu | Phe |  |
|  | 235 |  |  |  |  | 240 |  |  |  |  | 245 |  |  |

| ACT | GGT | GAT | CGC | TGC | CAA | AAC | TAC | GTA | ATG | GCC | AGC | TTC | 779 |
|---|---|---|---|---|---|---|---|---|---|---|---|---|---|
| Thr | Gly | Asp | Arg | Cys | Gln | Asn | Tyr | Val | Met | Ala | Ser | Phe |  |
|  |  |  | 250 |  |  |  |  | 255 |  |  |  |  |  |

| TAC | AAG | CAT | CTT | GGG | ATT | GAA | TTT | ATG | GAG | GCG | GAG | GAG | 818 |
|---|---|---|---|---|---|---|---|---|---|---|---|---|---|
| Tyr | Lys | His | Leu | Gly | Ile | Glu | Phe | Met | Glu | Ala | Glu | Glu |  |
| 260 |  |  |  |  | 265 |  |  |  |  | 270 |  |  |  |

| CTG | TAC | CAG | AAG | AGA | GTG | CTG | ACC | ATA | ACC | GGC | ATC | TGC | 857 |
|---|---|---|---|---|---|---|---|---|---|---|---|---|---|
| Leu | Tyr | Gln | Lys | Arg | Val | Leu | Thr | Ile | Thr | Gly | Ile | Cys |  |
|  |  | 275 |  |  |  |  | 280 |  |  |  |  | 285 |  |

| ATC | GCC | CTC | CTT | GTG | GTC | GGC | ATC | ATG | TGT | GTG | GTG | GCC | 896 |
|---|---|---|---|---|---|---|---|---|---|---|---|---|---|
| Ile | Ala | Leu | Leu | Val | Val | Gly | Ile | Met | Cys | Val | Val | Ala |  |
|  |  |  |  | 290 |  |  |  |  | 295 |  |  |  |  |

| TAC | TGC | AAA | ACC | AAG | AAA | CAG | CGG | AAA | AAG | CTG | CAT | GAC | 935 |
|---|---|---|---|---|---|---|---|---|---|---|---|---|---|
| Tyr | Cys | Lys | Thr | Lys | Lys | Gln | Arg | Lys | Lys | Leu | His | Asp |  |
|  | 300 |  |  |  |  | 305 |  |  |  |  | 310 |  |  |

| CGT | CTT | CGG | CAG | AGC | CTT | CGG | TCT | GAA | CGA | AAC | AAT | ATG | 974 |
|---|---|---|---|---|---|---|---|---|---|---|---|---|---|
| Arg | Leu | Arg | Gln | Ser | Leu | Arg | Ser | Glu | Arg | Asn | Asn | Met |  |
|  |  |  | 315 |  |  |  |  | 320 |  |  |  |  |  |

| ATG | AAC | ATT | GCC | AAT | GGG | CCT | CAC | CAT | CCT | AAC | CCA | CCC | 1013 |
|---|---|---|---|---|---|---|---|---|---|---|---|---|---|
| Met | Asn | Ile | Ala | Asn | Gly | Pro | His | His | Pro | Asn | Pro | Pro |  |
| 325 |  |  |  |  | 330 |  |  |  |  | 335 |  |  |  |

| CCC | GAG | AAT | GTC | CAG | CTG | GTG | AAT | CAA | TAC | GTA | TCT | AAA | 1052 |
|---|---|---|---|---|---|---|---|---|---|---|---|---|---|
| Pro | Glu | Asn | Val | Gln | Leu | Val | Asn | Gln | Tyr | Val | Ser | Lys |  |
|  |  | 340 |  |  |  |  | 345 |  |  |  |  | 350 |  |

| AAC | GTC | ATC | TCC | AGT | GAG | CAT | ATT | GTT | GAG | AGA | GAA | GCA | 1091 |
|---|---|---|---|---|---|---|---|---|---|---|---|---|---|
| Asn | Val | Ile | Ser | Ser | Glu | His | Ile | Val | Glu | Arg | Glu | Ala |  |
|  |  |  | 355 |  |  |  |  | 360 |  |  |  |  |  |

| GAG | ACA | TCC | TTT | TCC | ACC | AGT | CAC | TAT | ACT | TCC | ACA | GCC | 1130 |
|---|---|---|---|---|---|---|---|---|---|---|---|---|---|
| Glu | Thr | Ser | Phe | Ser | Thr | Ser | His | Tyr | Thr | Ser | Thr | Ala |  |
|  | 365 |  |  |  |  | 370 |  |  |  |  | 375 |  |  |

| CAT | CAC | TCC | ACT | ACT | GTC | ACC | CAG | ACT | CCT | AGC | CAC | AGC | 1169 |
|---|---|---|---|---|---|---|---|---|---|---|---|---|---|
| His | His | Ser | Thr | Thr | Val | Thr | Gln | Thr | Pro | Ser | His | Ser |  |
|  |  |  | 380 |  |  |  |  | 385 |  |  |  |  |  |

| TGG | AGC | AAC | GGA | CAC | ACT | GAA | AGC | ATC | CTT | TCC | GAA | AGC | 1208 |
|---|---|---|---|---|---|---|---|---|---|---|---|---|---|
| Trp | Ser | Asn | Gly | His | Thr | Glu | Ser | Ile | Leu | Ser | Glu | Ser |  |
| 390 |  |  |  |  | 395 |  |  |  |  | 400 |  |  |  |

| CAC | TCT | GTA | ATC | GTG | ATG | TCA | TCC | GTA | GAA | AAC | AGT | AGG | 1247 |
|---|---|---|---|---|---|---|---|---|---|---|---|---|---|

```
His  Ser  Val  Ile  Val  Met  Ser  Ser  Val  Glu  Asn  Ser  Arg
     405                 410                      415

CAC  AGC  AGC  CCA  ACT  GGG  GGC  CCA  AGA  GGA  CGT  CTT  AAT                    1286
His  Ser  Ser  Pro  Thr  Gly  Gly  Pro  Arg  Gly  Arg  Leu  Asn
               420                      425

GGC  ACA  GGA  GGC  CCT  CGT  GAA  TGT  AAC  AGC  TTC  CTC  AGG                    1325
Gly  Thr  Gly  Gly  Pro  Arg  Glu  Cys  Asn  Ser  Phe  Leu  Arg
     430                      435                      440

CAT  GCC  AGA  GAA  ACC  CCT  GAT  TCC  TAC  CGA  GAC  TCT  CCT                    1364
His  Ala  Arg  Glu  Thr  Pro  Asp  Ser  Tyr  Arg  Asp  Ser  Pro
               445                      450

CAT  AGT  GAA  AGG  TAT  GTG  TCA  GCC  ATG  ACC  ACC  CCG  GCT                    1403
His  Ser  Glu  Arg  Tyr  Val  Ser  Ala  Met  Thr  Thr  Pro  Ala
455                      460                      465

CGT  ATG  TCA  CCT  GTA  GAT  TTC  CAC  ACG  CCA  AGC  TCC  CCC                    1442
Arg  Met  Ser  Pro  Val  Asp  Phe  His  Thr  Pro  Ser  Ser  Pro
               470                      475                      480

AAA  TCG  CCC  CCT  TCG  GAA  ATG  TCT  CCA  CCC  GTG  TCC  AGC                    1481
Lys  Ser  Pro  Pro  Ser  Glu  Met  Ser  Pro  Pro  Val  Ser  Ser
                    485                      490

ATG  ACG  GTG  TCC  ATG  CCT  TCC  ATG  GCG  GTC  AGC  CCC  TTC                    1520
Met  Thr  Val  Ser  Met  Pro  Ser  Met  Ala  Val  Ser  Pro  Phe
     495                      500                      505

ATG  GAA  GAA  GAG  AGA  CCT  CTA  CTT  CTC  GTG  ACA  CCA  CCA                    1559
Met  Glu  Glu  Glu  Arg  Pro  Leu  Leu  Leu  Val  Thr  Pro  Pro
               510                      515

AGG  CTG  CGG  GAG  AAG  AAG  TTT  GAC  CAT  CAC  CCT  CAG  CAG                    1598
Arg  Leu  Arg  Glu  Lys  Lys  Phe  Asp  His  His  Pro  Gln  Gln
520                      525                      530

TTC  AGC  TCC  TTC  CAC  CAC  AAC  CCC  GCG  CAT  GAC  AGT  AAC                    1637
Phe  Ser  Ser  Phe  His  His  Asn  Pro  Ala  His  Asp  Ser  Asn
          535                      540                      545

AGC  CTC  CCT  GCT  AGC  CCC  TTG  AGG  ATA  GTG  GAG  GAT  GAG                    1676
Ser  Leu  Pro  Ala  Ser  Pro  Leu  Arg  Ile  Val  Glu  Asp  Glu
               550                      555

GAG  TAT  GAA  ACG  ACC  CAA  GAG  TAC  GAG  CCA  GCC  CAA  GAG                    1715
Glu  Tyr  Glu  Thr  Thr  Gln  Glu  Tyr  Glu  Pro  Ala  Gln  Glu
     560                      565                      570

CCT  GTT  AAG  AAA  CTC  GCC  AAT  AGC  CGG  CGG  GCC  AAA  AGA                    1754
Pro  Val  Lys  Lys  Leu  Ala  Asn  Ser  Arg  Arg  Ala  Lys  Arg
               575                      580

ACC  AAG  CCC  AAT  GGC  CAC  ATT  GCT  AAC  AGA  TTG  GAA  GTG                    1793
Thr  Lys  Pro  Asn  Gly  His  Ile  Ala  Asn  Arg  Leu  Glu  Val
585                      590                      595

GAC  AGC  AAC  ACA  AGC  TCC  CAG  AGC  AGT  AAC  TCA  GAG  AGT                    1832
Asp  Ser  Asn  Thr  Ser  Ser  Gln  Ser  Ser  Asn  Ser  Glu  Ser
               600                      605                      610

GAA  ACA  GAA  GAT  GAA  AGA  GTA  GGT  GAA  GAT  ACG  CCT  TTC                    1871
Glu  Thr  Glu  Asp  Glu  Arg  Val  Gly  Glu  Asp  Thr  Pro  Phe
                    615                      620

CTG  GGC  ATA  CAG  AAC  CCC  CTG  GCA  GCC  AGT  CTT  GAG  GCA                    1910
Leu  Gly  Ile  Gln  Asn  Pro  Leu  Ala  Ala  Ser  Leu  Glu  Ala
               625                      630                      635

ACA  CCT  GCC  TTC  CGC  CTG  GCT  GAC  AGC  AGG  ACT  AAC  CCA                    1949
Thr  Pro  Ala  Phe  Arg  Leu  Ala  Asp  Ser  Arg  Thr  Asn  Pro
               640                      645

GCA  GGC  CGC  TTC  TCG  ACA  CAG  GAA  GAA  ATC  CAG  GCC  AGG                    1988
Ala  Gly  Arg  Phe  Ser  Thr  Gln  Glu  Glu  Ile  Gln  Ala  Arg
650                      655                      660

CTG  TCT  AGT  GTA  ATT  GCT  AAC  CAA  GAC  CCT  ATT  GCT  GTA  TA              2029
```

```
Leu  Ser  Ser  Val  Ile  Ala  Asn  Gln  Asp  Pro  Ile  Ala  Val
     665                      670                     675

A    AACCTAAATA  AACACATAGA  TTCACCTGTA  AAACTTTATT                              2070

TTATATAATA  AAGTATTCCA  CCTTAAATTA  AACAATTTAT  TTTATTTTAG                      2120

CAGTTCTGCA  AATAGAAAAC  AGGAAAAAAA  CTTTTATAAA  TTAAATATAT                      2170

GTATGTAAAA  ATGAAAAAAA  AAAAAAAA                                                2199
```

( 2 ) INFORMATION FOR SEQ ID NO:8:

( i ) SEQUENCE CHARACTERISTICS:
        ( A ) LENGTH: 669 amino acids
        ( B ) TYPE: amino acid
        ( D ) TOPOLOGY: linear ( x i ) SEQUENCE DESCRIPTION: SEQ ID NO:8:

```
Ala  Arg  Ala  Pro  Gln  Arg  Gly  Arg  Ser  Leu  Ser  Pro  Ser  Arg  Asp
  1                 5                      10                      15

Lys  Leu  Phe  Pro  Asn  Pro  Ile  Arg  Ala  Leu  Gly  Pro  Asn  Ser  Pro
                    20                      25                      30

Ala  Pro  Arg  Ala  Val  Arg  Val  Glu  Arg  Ser  Val  Ser  Gly  Glu  Met
                    35                      40                      45

Ser  Glu  Arg  Lys  Glu  Arg  Gly  Lys  Gly  Lys  Gly  Lys  Lys  Lys
                    50                      55                      60

Glu  Arg  Gly  Ser  Gly  Lys  Lys  Pro  Glu  Ser  Ala  Ala  Gly  Ser  Gln
                    65                      70                      75

Ser  Pro  Ala  Leu  Pro  Pro  Arg  Leu  Lys  Glu  Met  Lys  Ser  Gln  Glu
                    80                      85                      90

Ser  Ala  Ala  Gly  Ser  Lys  Leu  Val  Leu  Arg  Cys  Glu  Thr  Ser  Ser
                    95                      100                     105

Glu  Tyr  Ser  Ser  Leu  Arg  Phe  Lys  Trp  Phe  Lys  Asn  Gly  Asn  Glu
                    110                     115                     120

Leu  Asn  Arg  Lys  Asn  Lys  Pro  Gln  Asn  Ile  Lys  Ile  Gln  Lys  Lys
                    125                     130                     135

Pro  Gly  Lys  Ser  Glu  Leu  Arg  Ile  Asn  Lys  Ala  Ser  Leu  Ala  Asp
                    140                     145                     150

Ser  Gly  Glu  Tyr  Met  Cys  Lys  Val  Ile  Ser  Lys  Leu  Gly  Asn  Asp
                    155                     160                     165

Ser  Ala  Ser  Ala  Asn  Ile  Thr  Ile  Val  Glu  Ser  Asn  Glu  Ile  Ile
                    170                     175                     180

Thr  Gly  Met  Pro  Ala  Ser  Thr  Glu  Gly  Ala  Tyr  Val  Ser  Ser  Glu
                    185                     190                     195

Ser  Pro  Ile  Arg  Ile  Ser  Val  Ser  Thr  Glu  Gly  Ala  Asn  Thr  Ser
                    200                     205                     210

Ser  Ser  Thr  Ser  Thr  Ser  Thr  Thr  Gly  Thr  Ser  His  Leu  Val  Lys
                    215                     220                     225

Cys  Ala  Glu  Lys  Glu  Lys  Thr  Phe  Cys  Val  Asn  Gly  Gly  Glu  Cys
                    230                     235                     240

Phe  Met  Val  Lys  Asp  Leu  Ser  Asn  Pro  Ser  Arg  Tyr  Leu  Cys  Lys
                    245                     250                     255

Cys  Gln  Pro  Gly  Phe  Thr  Gly  Ala  Arg  Cys  Thr  Glu  Asn  Val  Pro
                    260                     265                     270

Met  Lys  Val  Gln  Asn  Gln  Glu  Lys  Ala  Glu  Glu  Leu  Tyr  Gln  Lys
                    275                     280                     285

Arg  Val  Leu  Thr  Ile  Thr  Gly  Ile  Cys  Ile  Ala  Leu  Leu  Val  Val
                    290                     295                     300
```

Gly Ile Met Cys Val Val Ala Tyr Cys Lys Thr Lys Lys Gln Arg
            305             310                 315

Lys Lys Leu His Asp Arg Leu Arg Gln Ser Leu Arg Ser Glu Arg
            320             325                 330

Asn Asn Met Met Asn Ile Ala Asn Gly Pro His His Pro Asn Pro
            335             340                 345

Pro Pro Glu Asn Val Gln Leu Val Asn Gln Tyr Val Ser Lys Asn
            350             355                 360

Val Ile Ser Ser Glu His Ile Val Glu Arg Glu Ala Glu Thr Ser
            365             370                 375

Phe Ser Thr Ser His Tyr Thr Ser Thr Ala His His Ser Thr Thr
            380             385                 390

Val Thr Gln Thr Pro Ser His Ser Trp Ser Asn Gly His Thr Glu
            395             400                 405

Ser Ile Leu Ser Glu Ser His Ser Val Ile Val Met Ser Ser Val
            410             415                 420

Glu Asn Ser Arg His Ser Ser Pro Thr Gly Gly Pro Arg Gly Arg
            425             430                 435

Leu Asn Gly Thr Gly Gly Pro Arg Glu Cys Asn Ser Phe Leu Arg
            440             445                 450

His Ala Arg Glu Thr Pro Asp Ser Tyr Arg Asp Ser Pro His Ser
            455             460                 465

Glu Arg Tyr Val Ser Ala Met Thr Thr Pro Ala Arg Met Ser Pro
            470             475                 480

Val Asp Phe His Thr Pro Ser Ser Pro Lys Ser Pro Pro Ser Glu
            485             490                 495

Met Ser Pro Pro Val Ser Ser Met Thr Val Ser Met Pro Ser Met
            500             505                 510

Ala Val Ser Pro Phe Met Glu Glu Glu Arg Pro Leu Leu Leu Val
            515             520                 525

Thr Pro Pro Arg Leu Arg Glu Lys Lys Phe Asp His His Pro Gln
            530             535                 540

Gln Phe Ser Ser Phe His His Asn Pro Ala His Asp Ser Asn Ser
            545             550                 555

Leu Pro Ala Ser Pro Leu Arg Ile Val Glu Asp Glu Glu Tyr Glu
            560             565                 570

Thr Thr Gln Glu Tyr Glu Pro Ala Gln Glu Pro Val Lys Lys Leu
            575             580                 585

Ala Asn Ser Arg Arg Ala Lys Arg Thr Lys Pro Asn Gly His Ile
            590             595                 600

Ala Asn Arg Leu Glu Val Asp Ser Asn Thr Ser Ser Gln Ser Ser
            605             610                 615

Asn Ser Glu Ser Glu Thr Glu Asp Glu Arg Val Gly Glu Asp Thr
            620             625                 630

Pro Phe Leu Gly Ile Gln Asn Pro Leu Ala Ala Ser Leu Glu Ala
            635             640                 645

Thr Pro Ala Phe Arg Leu Ala Asp Ser Arg Thr Asn Pro Ala Gly
            650             655                 660

Arg Phe Ser Thr Gln Glu Glu Ile Gln
            665             669

( 2 ) INFORMATION FOR SEQ ID NO:9:

( i ) SEQUENCE CHARACTERISTICS:

5,840,525

-continued ( A ) LENGTH: 732 amino acids
( B ) TYPE: amino acid
( D ) TOPOLOGY: linear ( x i ) SEQUENCE DESCRIPTION: SEQ ID NO:9:

| Asp | Lys | Leu | Phe | Pro | Asn | Pro | Ile | Arg | Ala | Leu | Gly | Pro | Asn | Ser |
|---|---|---|---|---|---|---|---|---|---|---|---|---|---|---|
| 1 | | | | 5 | | | | | 10 | | | | | 15 |
| Pro | Ala | Pro | Arg | Ala | Val | Arg | Val | Glu | Arg | Ser | Val | Ser | Gly | Glu |
| | | | | 20 | | | | | 25 | | | | | 30 |
| Met | Ser | Glu | Arg | Lys | Glu | Gly | Arg | Gly | Lys | Gly | Lys | Gly | Lys | Lys |
| | | | | 35 | | | | | 40 | | | | | 45 |
| Lys | Glu | Arg | Gly | Ser | Gly | Lys | Lys | Pro | Glu | Ser | Ala | Ala | Gly | Ser |
| | | | | 50 | | | | | 55 | | | | | 60 |
| Gln | Ser | Pro | Ala | Leu | Pro | Pro | Gln | Leu | Lys | Glu | Met | Lys | Ser | Gln |
| | | | | 65 | | | | | 70 | | | | | 75 |
| Glu | Ser | Ala | Ala | Gly | Ser | Lys | Leu | Val | Leu | Arg | Cys | Glu | Thr | Ser |
| | | | | 80 | | | | | 85 | | | | | 90 |
| Ser | Glu | Tyr | Ser | Ser | Leu | Arg | Phe | Lys | Trp | Phe | Lys | Asn | Gly | Asn |
| | | | | 95 | | | | | 100 | | | | | 105 |
| Glu | Leu | Asn | Arg | Lys | Asn | Lys | Pro | Gln | Asn | Ile | Lys | Ile | Gln | Lys |
| | | | | 110 | | | | | 115 | | | | | 120 |
| Lys | Pro | Gly | Lys | Ser | Glu | Leu | Arg | Ile | Asn | Lys | Ala | Ser | Leu | Ala |
| | | | | 125 | | | | | 130 | | | | | 135 |
| Asp | Ser | Gly | Glu | Tyr | Met | Cys | Lys | Val | Ile | Ser | Lys | Leu | Gly | Asn |
| | | | | 140 | | | | | 145 | | | | | 150 |
| Asp | Ser | Ala | Ser | Ala | Asn | Ile | Thr | Ile | Val | Glu | Ser | Asn | Glu | Ile |
| | | | | 155 | | | | | 160 | | | | | 165 |
| Ile | Thr | Gly | Met | Pro | Ala | Ser | Thr | Glu | Gly | Ala | Tyr | Val | Ser | Ser |
| | | | | 170 | | | | | 175 | | | | | 180 |
| Glu | Ser | Pro | Ile | Arg | Ile | Ser | Val | Ser | Thr | Glu | Gly | Ala | Asn | Thr |
| | | | | 185 | | | | | 190 | | | | | 195 |
| Ser | Ser | Ser | Thr | Ser | Thr | Ser | Thr | Thr | Gly | Thr | Ser | His | Leu | Val |
| | | | | 200 | | | | | 205 | | | | | 210 |
| Lys | Cys | Ala | Glu | Lys | Glu | Lys | Thr | Phe | Cys | Val | Asn | Gly | Gly | Glu |
| | | | | 215 | | | | | 220 | | | | | 225 |
| Cys | Phe | Met | Val | Lys | Asp | Leu | Ser | Asn | Pro | Ser | Arg | Tyr | Leu | Cys |
| | | | | 230 | | | | | 235 | | | | | 240 |
| Lys | Cys | Pro | Asn | Glu | Phe | Thr | Gly | Asp | Arg | Cys | Gln | Asn | Tyr | Val |
| | | | | 245 | | | | | 250 | | | | | 255 |
| Met | Ala | Ser | Phe | Tyr | Lys | His | Leu | Gly | Ile | Glu | Phe | Met | Glu | Ala |
| | | | | 260 | | | | | 265 | | | | | 270 |
| Glu | Glu | Leu | Tyr | Gln | Lys | Arg | Val | Leu | Thr | Ile | Thr | Gly | Ile | Cys |
| | | | | 275 | | | | | 280 | | | | | 285 |
| Ile | Ala | Leu | Leu | Val | Val | Gly | Ile | Met | Cys | Val | Val | Ala | Tyr | Cys |
| | | | | 290 | | | | | 295 | | | | | 300 |
| Lys | Thr | Lys | Lys | Gln | Arg | Lys | Lys | Leu | His | Asp | Arg | Leu | Arg | Gln |
| | | | | 305 | | | | | 310 | | | | | 315 |
| Ser | Leu | Arg | Ser | Glu | Arg | Asn | Asn | Met | Met | Asn | Ile | Ala | Asn | Gly |
| | | | | 320 | | | | | 325 | | | | | 330 |
| Pro | His | His | Pro | Asn | Pro | Pro | Pro | Glu | Asn | Val | Gln | Leu | Val | Asn |
| | | | | 335 | | | | | 340 | | | | | 345 |
| Gln | Tyr | Val | Ser | Lys | Asn | Val | Ile | Ser | Ser | Glu | His | Ile | Val | Glu |
| | | | | 350 | | | | | 355 | | | | | 360 |
| Arg | Glu | Ala | Glu | Thr | Ser | Phe | Ser | Thr | Ser | His | Tyr | Thr | Ser | Thr |
| | | | | 365 | | | | | 370 | | | | | 375 |

| | | | | | | | | | | | | |
|---|---|---|---|---|---|---|---|---|---|---|---|---|
| Ala | His | His | Ser | Thr 380 | Thr | Val | Thr | Gln | Thr 385 | Pro | Ser | His | Ser | Trp 390 |
| Ser | Asn | Gly | His | Thr 395 | Glu | Ser | Ile | Leu | Ser 400 | Glu | Ser | His | Ser | Val 405 |
| Ile | Val | Met | Ser | Ser 410 | Val | Glu | Asn | Ser | Arg 415 | His | Ser | Ser | Pro | Thr 420 |
| Gly | Gly | Pro | Arg | Gly 425 | Arg | Leu | Asn | Gly | Thr 430 | Gly | Gly | Pro | Arg | Glu 435 |
| Cys | Asn | Ser | Phe | Leu 440 | Arg | His | Ala | Arg | Glu 445 | Thr | Pro | Asp | Ser | Tyr 450 |
| Arg | Asp | Ser | Pro | His 455 | Ser | Glu | Arg | Tyr | Val 460 | Ser | Ala | Met | Thr | Thr 465 |
| Pro | Ala | Arg | Met | Ser 470 | Pro | Val | Asp | Phe | His 475 | Thr | Pro | Ser | Ser | Pro 480 |
| Lys | Ser | Pro | Pro | Ser 485 | Glu | Met | Ser | Pro | Val 490 | Ser | Ser | Met | Thr 495 |
| Val | Ser | Met | Pro | Ser 500 | Met | Ala | Val | Ser | Pro 505 | Phe | Met | Glu | Glu | Glu 510 |
| Arg | Pro | Leu | Leu | Leu 515 | Val | Thr | Pro | Pro | Arg 520 | Leu | Arg | Glu | Lys | Lys 525 |
| Phe | Asp | His | His | Pro 530 | Gln | Gln | Phe | Ser | Ser 535 | Phe | His | His | Asn | Pro 540 |
| Ala | His | Asp | Ser | Asn 545 | Ser | Leu | Pro | Ala | Ser 550 | Pro | Leu | Arg | Ile | Val 555 |
| Glu | Asp | Glu | Glu | Tyr 560 | Glu | Thr | Thr | Gln | Glu 565 | Tyr | Glu | Pro | Ala | Gln 570 |
| Glu | Pro | Val | Lys | Lys 575 | Leu | Ala | Asn | Ser | Arg 580 | Arg | Ala | Lys | Arg | Thr 585 |
| Lys | Pro | Asn | Gly | His 590 | Ile | Ala | Asn | Arg | Leu 595 | Glu | Val | Asp | Ser | Asn 600 |
| Thr | Ser | Ser | Gln | Ser 605 | Ser | Asn | Ser | Glu | Ser 610 | Glu | Thr | Glu | Asp | Glu 615 |
| Arg | Val | Gly | Glu | Asp 620 | Thr | Pro | Phe | Leu | Gly 625 | Ile | Gln | Asn | Pro | Leu 630 |
| Ala | Ala | Ser | Leu | Glu 635 | Ala | Thr | Pro | Ala | Phe 640 | Arg | Leu | Ala | Asp | Ser 645 |
| Arg | Thr | Asn | Pro | Ala 650 | Gly | Arg | Phe | Ser | Thr 655 | Gln | Glu | Glu | Ile | Gln 660 |
| Ala | Arg | Leu | Ser | Ser 665 | Val | Ile | Ala | Asn | Gln 670 | Asp | Pro | Ile | Ala | Val 675 |
| Xaa | Asn | Leu | Asn | Lys 680 | His | Ile | Asp | Ser | Pro 685 | Val | Lys | Leu | Tyr | Phe 690 |
| Ile | Xaa | Xaa | Ser | Ile 695 | Pro | Pro | Xaa | Ile | Lys 700 | Gln | Phe | Ile | Leu | Phe 705 |
| Xaa | Gln | Phe | Cys | Lys 710 | Xaa | Lys | Thr | Gly | Lys 715 | Lys | Leu | Leu | Xaa | Ile 720 |
| Lys | Tyr | Met | Tyr | Val 725 | Lys | Met | Lys | Lys | Lys 730 | Lys | Lys 732 |

( 2 ) INFORMATION FOR SEQ ID NO:10:

( i ) SEQUENCE CHARACTERISTICS:
        ( A ) LENGTH: 66 amino acids
        ( B ) TYPE: amino acid
        ( D ) TOPOLOGY: linear ( x i ) SEQUENCE DESCRIPTION: SEQ ID NO:10:

| Ser | His | Leu | Val | Lys | Cys | Ala | Glu | Lys | Glu | Lys | Thr | Phe | Cys | Val |
| 1 | | | | 5 | | | | | 10 | | | | | 15 |

| Asn | Gly | Gly | Glu | Cys | Phe | Met | Val | Lys | Asp | Leu | Ser | Asn | Pro | Ser |
| | | | | 20 | | | | | 25 | | | | | 30 |

| Arg | Tyr | Leu | Cys | Lys | Cys | Gln | Pro | Gly | Phe | Thr | Gly | Ala | Arg | Cys |
| | | | | 35 | | | | | 40 | | | | | 45 |

| Thr | Glu | Asn | Val | Pro | Met | Lys | Val | Gln | Asn | Gln | Glu | Lys | Ala | Glu |
| | | | | 50 | | | | | 55 | | | | | 60 |

| Glu | Leu | Tyr | Gln | Lys | Arg |
| | | | | 65 | 66 |

( 2 ) INFORMATION FOR SEQ ID NO:11:

( i ) SEQUENCE CHARACTERISTICS:
        ( A ) LENGTH: 71 amino acids
        ( B ) TYPE: amino acid
        ( D ) TOPOLOGY: linear ( x i ) SEQUENCE DESCRIPTION: SEQ ID NO:11:

| Ser | His | Leu | Val | Lys | Cys | Ala | Glu | Lys | Glu | Lys | Thr | Phe | Cys | Val |
| 1 | | | | 5 | | | | | 10 | | | | | 15 |

| Asn | Gly | Gly | Glu | Cys | Phe | Met | Val | Lys | Asp | Leu | Ser | Asn | Pro | Ser |
| | | | | 20 | | | | | 25 | | | | | 30 |

| Arg | Tyr | Leu | Cys | Lys | Cys | Pro | Asn | Glu | Phe | Thr | Gly | Asp | Arg | Cys |
| | | | | 35 | | | | | 40 | | | | | 45 |

| Gln | Asn | Tyr | Val | Met | Ala | Ser | Phe | Tyr | Lys | His | Leu | Gly | Ile | Glu |
| | | | | 50 | | | | | 55 | | | | | 60 |

| Phe | Met | Glu | Ala | Glu | Glu | Leu | Tyr | Gln | Lys | Arg |
| | | | | 65 | | | | | 70 | 71 |

( 2 ) INFORMATION FOR SEQ ID NO:12:

( i ) SEQUENCE CHARACTERISTICS:
        ( A ) LENGTH: 2010 bases
        ( B ) TYPE: nucleic acid
        ( C ) STRANDEDNESS: single
        ( D ) TOPOLOGY: linear ( x i ) SEQUENCE DESCRIPTION: SEQ ID NO:12:

| | | | | | |
|---|---|---|---|---|---|
| GGGCGCGAGC | GCCTCAGCGC | GGCCGCTCGC | TCTCCCCCTC | GAGGGACAAA | 50 |
| CTTTTCCCAA | ACCCGATCCG | AGCCCTTGGA | CCAAACTCGC | CTGCGCCGAG | 100 |
| AGCCGTCCGC | GTAGAGCGCT | CCGTCTCCGG | CGAGATGTCC | GAGCGCAAAG | 150 |
| AAGGCAGAGG | CAAAGGGAAG | GGCAAGAAGA | AGGAGCGAGG | CTCCGGCAAG | 200 |
| AAGCCGGAGT | CCGCGGCGGG | CAGCCAGAGC | CCAGCCTTGC | CTCCCCGATT | 250 |
| GAAAGAGATG | AAAAGCCAGG | AATCGGCTGC | AGGTTCCAAA | CTAGTCCTTC | 300 |
| GGTGTGAAAC | CAGTTCTGAA | TACTCCTCTC | TCAGATTCAA | GTGGTTCAAG | 350 |
| AATGGGAATG | AATTGAATCG | AAAAAACAAA | CCACAAAATA | TCAAGATACA | 400 |
| AAAAAAGCCA | GGGAAGTCAG | AACTTCGCAT | TAACAAAGCA | TCACTGGCTG | 450 |
| ATTCTGGAGA | GTATATGTGC | AAAGTGATCA | GCAAATTAGG | AAATGACAGT | 500 |
| GCCTCTGCCA | ATATCACCAT | CGTGGAATCA | AACGAGATCA | TCACTGGTAT | 550 |
| GCCAGCCTCA | ACTGAAGGAG | CATATGTGTC | TTCAGAGTCT | CCCATTAGAA | 600 |
| TATCAGTATC | CACAGAAGGA | GCAAATACTT | CTTCATCTAC | ATCTACATCC | 650 |

| | | | | |
|---|---|---|---|---|
| ACCACTGGGA | CAAGCCATCT | TGTAAAATGT | GCGGAGAAGG | AGAAAACTTT | 700 |
| CTGTGTGAAT | GGAGGGGAGT | GCTTCATGGT | GAAAGACCTT | TCAAACCCCT | 750 |
| CGAGATACTT | GTGCAAGTGC | CAACCTGGAT | TCACTGGAGC | AAGATGTACT | 800 |
| GAGAATGTGC | CCATGAAAGT | CCAAAACCAA | GAAAGGCGG | AGGAGCTGTA | 850 |
| CCAGAAGAGA | GTGCTGACCA | TAACCGGCAT | CTGCATCGCC | CTCCTTGTGG | 900 |
| TCGGCATCAT | GTGTGTGGTG | GCCTACTGCA | AAACCAAGAA | ACAGCGGAAA | 950 |
| AAGCTGCATG | ACCGTCTTCG | GCAGAGCCTT | CGGTCTGAAC | GAAACAATAT | 1000 |
| GATGAACATT | GCCAATGGGC | CTCACCATCC | TAACCCACCC | CCCGAGAATG | 1050 |
| TCCAGCTGGT | GAATCAATAC | GTATCTAAAA | ACGTCATCTC | CAGTGAGCAT | 1100 |
| ATTGTTGAGA | GAGAAGCAGA | GACATCCTTT | TCCACCAGTC | ACTATACTTC | 1150 |
| CACAGCCCAT | CACTCCACTA | CTGTCACCCA | GACTCCTAGC | CACAGCTGGA | 1200 |
| GCAACGGACA | CACTGAAAGC | ATCCTTTCCG | AAAGCCACTC | TGTAATCGTG | 1250 |
| ATGTCATCCG | TAGAAAACAG | TAGGCACAGC | AGCCCAACTG | GGGGCCCAAG | 1300 |
| AGGACGTCTT | AATGGCACAG | GAGGCCCTCG | TGAATGTAAC | AGCTTCCTCA | 1350 |
| GGCATGCCAG | AGAAACCCCT | GATTCCTACC | GAGACTCTCC | TCATAGTGAA | 1400 |
| AGGTATGTGT | CAGCCATGAC | CACCCCGGCT | CGTATGTCAC | CTGTAGATTT | 1450 |
| CCACACGCCA | AGCTCCCCCA | AATCGCCCCC | TTCGGAAATG | TCTCCACCCG | 1500 |
| TGTCCAGCAT | GACGGTGTCC | ATGCCTTCCA | TGGCGGTCAG | CCCCTTCATG | 1550 |
| GAAGAAGAGA | GACCTCTACT | TCTCGTGACA | CCACCAAGGC | TGCGGGAGAA | 1600 |
| GAAGTTTGAC | CATCACCCTC | AGCAGTTCAG | CTCCTTCCAC | CACAACCCCG | 1650 |
| CGCATGACAG | TAACAGCCTC | CCTGCTAGCC | CCTTGAGGAT | AGTGGAGGAT | 1700 |
| GAGGAGTATG | AAACGACCCA | AGAGTACGAG | CCAGCCCAAG | AGCCTGTTAA | 1750 |
| GAAACTCGCC | AATAGCCGGC | GGGCCAAAAG | AACCAAGCCC | AATGGCCACA | 1800 |
| TTGCTAACAG | ATTGGAAGTG | GACAGCAACA | CAAGCTCCCA | GAGCAGTAAC | 1850 |
| TCAGAGAGTG | AAACAGAAGA | TGAAAGAGTA | GGTGAAGATA | CGCCTTTCCT | 1900 |
| GGGCATACAG | AACCCCCTGG | CAGCCAGTCT | TGAGGCAACA | CCTGCCTTCC | 1950 |
| GCCTGGCTGA | CAGCAGGACT | AACCCAGCAG | GCCGCTTCTC | GACACAGGAA | 2000 |
| GAAATCCAGG | | | | | 2010 |

( 2 ) INFORMATION FOR SEQ ID NO:13:

( i ) SEQUENCE CHARACTERISTICS:
        ( A ) LENGTH: 669 amino acids
        ( B ) TYPE: amino acid
        ( D ) TOPOLOGY: linear ( x i ) SEQUENCE DESCRIPTION: SEQ ID NO:13:

```
Ala  Arg  Ala  Pro  Gln  Arg  Gly  Arg  Ser  Leu  Ser  Pro  Ser  Arg  Asp
 1                    5                        10                       15

Lys  Leu  Phe  Pro  Asn  Pro  Ile  Arg  Ala  Leu  Gly  Pro  Asn  Ser  Pro
                     20                        25                       30

Ala  Pro  Arg  Ala  Val  Arg  Val  Glu  Arg  Ser  Val  Ser  Gly  Glu  Met
                     35                        40                       45

Ser  Glu  Arg  Lys  Glu  Gly  Arg  Gly  Lys  Gly  Lys  Gly  Lys  Lys  Lys
                     50                        55                       60

Glu  Arg  Gly  Ser  Gly  Lys  Lys  Pro  Glu  Ser  Ala  Ala  Gly  Ser  Gln
                     65                        70                       75
```

| | | | | | | | | | | | | | |
|---|---|---|---|---|---|---|---|---|---|---|---|---|---|
|Ser|Pro|Ala|Leu|Pro<br>80|Pro|Arg|Leu|Lys|Glu<br>85|Met|Lys|Ser|Gln|Glu<br>90|
|Ser|Ala|Ala|Gly|Ser<br>95|Lys|Leu|Val|Leu|Arg<br>100|Cys|Glu|Thr|Ser|Ser<br>105|
|Glu|Tyr|Ser|Ser|Leu<br>110|Arg|Phe|Lys|Trp|Phe<br>115|Lys|Asn|Gly|Asn|Glu<br>120|
|Leu|Asn|Arg|Lys|Asn<br>125|Lys|Pro|Gln|Asn|Ile<br>130|Lys|Ile|Gln|Lys|Lys<br>135|
|Pro|Gly|Lys|Ser|Glu<br>140|Leu|Arg|Ile|Asn|Lys<br>145|Ala|Ser|Leu|Ala|Asp<br>150|
|Ser|Gly|Glu|Tyr|Met<br>155|Cys|Lys|Val|Ile|Ser<br>160|Lys|Leu|Gly|Asn|Asp<br>165|
|Ser|Ala|Ser|Ala|Asn<br>170|Ile|Thr|Ile|Val|Glu<br>175|Ser|Asn|Glu|Ile|Ile<br>180|
|Thr|Gly|Met|Pro|Ala<br>185|Ser|Thr|Glu|Gly|Ala<br>190|Tyr|Val|Ser|Ser|Glu<br>195|
|Ser|Pro|Ile|Arg|Ile<br>200|Ser|Val|Ser|Thr|Glu<br>205|Gly|Ala|Asn|Thr|Ser<br>210|
|Ser|Ser|Thr|Ser|Thr<br>215|Ser|Thr|Thr|Gly|Thr<br>220|Ser|His|Leu|Val|Lys<br>225|
|Cys|Ala|Glu|Lys|Glu<br>230|Lys|Thr|Phe|Cys|Val<br>235|Asn|Gly|Gly|Glu|Cys<br>240|
|Phe|Met|Val|Lys|Asp<br>245|Leu|Ser|Asn|Pro|Ser<br>250|Arg|Tyr|Leu|Cys|Lys<br>255|
|Cys|Gln|Pro|Gly|Phe<br>260|Thr|Gly|Ala|Arg|Cys<br>265|Thr|Glu|Asn|Val|Pro<br>270|
|Met|Lys|Val|Gln|Asn<br>275|Gln|Glu|Lys|Ala|Glu<br>280|Glu|Leu|Tyr|Gln|Lys<br>285|
|Arg|Val|Leu|Thr|Ile<br>290|Thr|Gly|Ile|Cys|Ile<br>295|Ala|Leu|Leu|Val|Val<br>300|
|Gly|Ile|Met|Cys|Val<br>305|Val|Ala|Tyr|Cys|Lys<br>310|Thr|Lys|Lys|Gln|Arg<br>315|
|Lys|Lys|Leu|His|Asp<br>320|Arg|Leu|Arg|Gln|Ser<br>325|Leu|Arg|Ser|Glu|Arg<br>330|
|Asn|Asn|Met|Met|Asn<br>335|Ile|Ala|Asn|Gly|Pro<br>340|His|His|Pro|Asn|Pro<br>345|
|Pro|Pro|Glu|Asn|Val<br>350|Gln|Leu|Val|Asn|Gln<br>355|Tyr|Val|Ser|Lys|Asn<br>360|
|Val|Ile|Ser|Ser|Glu<br>365|His|Ile|Val|Glu|Arg<br>370|Glu|Ala|Glu|Thr|Ser<br>375|
|Phe|Ser|Thr|Ser|His<br>380|Tyr|Thr|Ser|Thr|Ala<br>385|His|His|Ser|Thr|Thr<br>390|
|Val|Thr|Gln|Thr|Pro<br>395|Ser|His|Ser|Trp|Ser<br>400|Asn|Gly|His|Thr|Glu<br>405|
|Ser|Ile|Leu|Ser|Glu<br>410|Ser|His|Ser|Val|Ile<br>415|Val|Met|Ser|Ser|Val<br>420|
|Glu|Asn|Ser|Arg|His<br>425|Ser|Ser|Pro|Thr|Gly<br>430|Gly|Pro|Arg|Gly|Arg<br>435|
|Leu|Asn|Gly|Thr|Gly<br>440|Gly|Pro|Arg|Glu|Cys<br>445|Asn|Ser|Phe|Leu|Arg<br>450|
|His|Ala|Arg|Glu|Thr<br>455|Pro|Asp|Ser|Tyr|Arg<br>460|Asp|Ser|Pro|His|Ser<br>465|
|Glu|Arg|Tyr|Val|Ser|Ala|Met|Thr|Thr|Pro|Ala|Arg|Met|Ser|Pro|

|  |  |  |  | 470 |  |  |  | 475 |  |  |  | 480 |
|---|---|---|---|---|---|---|---|---|---|---|---|---|
| Val | Asp | Phe | His | Thr | Pro | Ser | Ser | Pro | Lys | Ser | Pro | Pro | Ser | Glu |
|  |  |  |  | 485 |  |  |  | 490 |  |  |  | 495 |
| Met | Ser | Pro | Pro | Val | Ser | Ser | Met | Thr | Val | Ser | Met | Pro | Ser | Met |
|  |  |  |  | 500 |  |  |  | 505 |  |  |  | 510 |
| Ala | Val | Ser | Pro | Phe | Met | Glu | Glu | Glu | Arg | Pro | Leu | Leu | Leu | Val |
|  |  |  |  | 515 |  |  |  | 520 |  |  |  | 525 |
| Thr | Pro | Pro | Arg | Leu | Arg | Glu | Lys | Lys | Phe | Asp | His | His | Pro | Gln |
|  |  |  |  | 530 |  |  |  | 535 |  |  |  | 540 |
| Gln | Phe | Ser | Ser | Phe | His | His | Asn | Pro | Ala | His | Asp | Ser | Asn | Ser |
|  |  |  |  | 545 |  |  |  | 550 |  |  |  | 555 |
| Leu | Pro | Ala | Ser | Pro | Leu | Arg | Ile | Val | Glu | Asp | Glu | Glu | Tyr | Glu |
|  |  |  |  | 560 |  |  |  | 565 |  |  |  | 570 |
| Thr | Thr | Gln | Glu | Tyr | Glu | Pro | Ala | Gln | Glu | Pro | Val | Lys | Lys | Leu |
|  |  |  |  | 575 |  |  |  | 580 |  |  |  | 585 |
| Ala | Asn | Ser | Arg | Arg | Ala | Lys | Arg | Thr | Lys | Pro | Asn | Gly | His | Ile |
|  |  |  |  | 590 |  |  |  | 595 |  |  |  | 600 |
| Ala | Asn | Arg | Leu | Glu | Val | Asp | Ser | Asn | Thr | Ser | Ser | Gln | Ser | Ser |
|  |  |  |  | 605 |  |  |  | 610 |  |  |  | 615 |
| Asn | Ser | Glu | Ser | Glu | Thr | Glu | Asp | Glu | Arg | Val | Gly | Glu | Asp | Thr |
|  |  |  |  | 620 |  |  |  | 625 |  |  |  | 630 |
| Pro | Phe | Leu | Gly | Ile | Gln | Asn | Pro | Leu | Ala | Ala | Ser | Leu | Glu | Ala |
|  |  |  |  | 635 |  |  |  | 640 |  |  |  | 645 |
| Thr | Pro | Ala | Phe | Arg | Leu | Ala | Asp | Ser | Arg | Thr | Asn | Pro | Ala | Gly |
|  |  |  |  | 650 |  |  |  | 655 |  |  |  | 660 |
| Arg | Phe | Ser | Thr | Gln | Glu | Glu | Ile | Gln |
|  |  |  |  | 665 |  |  |  | 669 |

( 2 ) INFORMATION FOR SEQ ID NO:14:

( i ) SEQUENCE CHARACTERISTICS:
        ( A ) LENGTH: 95 amino acids
        ( B ) TYPE: amino acid
        ( D ) TOPOLOGY: linear ( x i ) SEQUENCE DESCRIPTION: SEQ ID NO:14:

| Ser | His | Leu | Val | Lys | Cys | Ala | Glu | Lys | Glu | Lys | Thr | Phe | Cys | Val |
|---|---|---|---|---|---|---|---|---|---|---|---|---|---|---|
| 1 |  |  |  | 5 |  |  |  |  | 10 |  |  |  |  | 15 |
| Asn | Gly | Gly | Glu | Cys | Phe | Met | Val | Lys | Asp | Leu | Ser | Asn | Pro | Ser |
|  |  |  |  | 20 |  |  |  |  | 25 |  |  |  |  | 30 |
| Arg | Tyr | Leu | Cys | Lys | Cys | Gln | Pro | Gly | Phe | Thr | Gly | Ala | Arg | Cys |
|  |  |  |  | 35 |  |  |  |  | 40 |  |  |  |  | 45 |
| Thr | Glu | Asn | Val | Pro | Met | Lys | Val | Gln | Asn | Gln | Glu | Lys | Ala | Glu |
|  |  |  |  | 50 |  |  |  |  | 55 |  |  |  |  | 60 |
| Glu | Leu | Tyr | Gln | Lys | Arg | Val | Leu | Thr | Ile | Thr | Gly | Ile | Cys | Ile |
|  |  |  |  | 65 |  |  |  |  | 70 |  |  |  |  | 75 |
| Ala | Leu | Leu | Val | Val | Gly | Ile | Met | Cys | Val | Val | Ala | Tyr | Cys | Lys |
|  |  |  |  | 80 |  |  |  |  | 85 |  |  |  |  | 90 |
| Thr | Lys | Lys | Gln | Arg |
|  |  |  |  | 95 |

( 2 ) INFORMATION FOR SEQ ID NO:15:

( i ) SEQUENCE CHARACTERISTICS:
        ( A ) LENGTH: 91 amino acids
        ( B ) TYPE: amino acid
        ( D ) TOPOLOGY: linear ( x i ) SEQUENCE DESCRIPTION: SEQ ID NO:15:

| Asn | Ser | Asp | Ser | Glu | Cys | Pro | Leu | Ser | His | Asp | Gly | Tyr | Cys | Leu |
|---|---|---|---|---|---|---|---|---|---|---|---|---|---|---|
| 1 | | | | 5 | | | | | 10 | | | | | 15 |

| His | Asp | Gly | Val | Cys | Met | Tyr | Ile | Glu | Ala | Leu | Asp | Lys | Tyr | Ala |
|---|---|---|---|---|---|---|---|---|---|---|---|---|---|---|
| | | | | 20 | | | | | 25 | | | | | 30 |

| Cys | Asn | Cys | Val | Val | Gly | Tyr | Ile | Gly | Glu | Arg | Cys | Gln | Tyr | Arg |
|---|---|---|---|---|---|---|---|---|---|---|---|---|---|---|
| | | | | 35 | | | | | 40 | | | | | 45 |

| Asp | Leu | Lys | Trp | Trp | Glu | Leu | Arg | His | Ala | Gly | His | Gly | Gln | Gln |
|---|---|---|---|---|---|---|---|---|---|---|---|---|---|---|
| | | | | 50 | | | | | 55 | | | | | 60 |

| Gln | Lys | Val | Ile | Val | Val | Ala | Val | Cys | Val | Val | Val | Leu | Val | Met |
|---|---|---|---|---|---|---|---|---|---|---|---|---|---|---|
| | | | | 65 | | | | | 70 | | | | | 75 |

| Leu | Leu | Leu | Leu | Ser | Leu | Trp | Gly | Ala | His | Tyr | Tyr | Arg | Thr | Gln |
|---|---|---|---|---|---|---|---|---|---|---|---|---|---|---|
| | | | | 80 | | | | | 85 | | | | | 90 |

| Lys |
|---|
| 91 |

( 2 ) INFORMATION FOR SEQ ID NO:16:

( i ) SEQUENCE CHARACTERISTICS:
    ( A ) LENGTH: 82 amino acids
    ( B ) TYPE: amino acid
    ( D ) TOPOLOGY: linear ( x i ) SEQUENCE DESCRIPTION: SEQ ID NO:16:

| Asn | Asp | Cys | Pro | Asp | Ser | His | Thr | Gln | Phe | Cys | Phe | His | Gly | Thr |
|---|---|---|---|---|---|---|---|---|---|---|---|---|---|---|
| 1 | | | | 5 | | | | | 10 | | | | | 15 |

| Cys | Arg | Phe | Leu | Val | Gln | Glu | Asp | Lys | Pro | Ala | Cys | Val | Cys | His |
|---|---|---|---|---|---|---|---|---|---|---|---|---|---|---|
| | | | | 20 | | | | | 25 | | | | | 30 |

| Ser | Gly | Tyr | Val | Gly | Ala | Arg | Cys | Glu | His | Ala | Asp | Leu | Leu | Ala |
|---|---|---|---|---|---|---|---|---|---|---|---|---|---|---|
| | | | | 35 | | | | | 40 | | | | | 45 |

| Val | Val | Ala | Ala | Ser | Gln | Lys | Lys | Gln | Ala | Ile | Thr | Ala | Leu | Val |
|---|---|---|---|---|---|---|---|---|---|---|---|---|---|---|
| | | | | 50 | | | | | 55 | | | | | 60 |

| Val | Val | Ser | Ile | Val | Ala | Leu | Ala | Val | Leu | Ile | Ile | Thr | Cys | Val |
|---|---|---|---|---|---|---|---|---|---|---|---|---|---|---|
| | | | | 65 | | | | | 70 | | | | | 75 |

| Leu | Ile | His | Cys | Cys | Gln | Val |
|---|---|---|---|---|---|---|
| | | | | 80 | | 82 |

( 2 ) INFORMATION FOR SEQ ID NO:17:

( i ) SEQUENCE CHARACTERISTICS:
    ( A ) LENGTH: 87 amino acids
    ( B ) TYPE: amino acid
    ( D ) TOPOLOGY: linear ( x i ) SEQUENCE DESCRIPTION: SEQ ID NO:17:

| Lys | Lys | Lys | Asn | Pro | Cys | Asn | Ala | Glu | Phe | Gln | Asn | Phe | Cys | Ile |
|---|---|---|---|---|---|---|---|---|---|---|---|---|---|---|
| 1 | | | | 5 | | | | | 10 | | | | | 15 |

| His | Gly | Glu | Cys | Lys | Tyr | Ile | Glu | His | Leu | Glu | Ala | Val | Thr | Cys |
|---|---|---|---|---|---|---|---|---|---|---|---|---|---|---|
| | | | | 20 | | | | | 25 | | | | | 30 |

| Lys | Cys | Gln | Gln | Glu | Tyr | Phe | Gly | Glu | Arg | Cys | Gly | Glu | Lys | Ser |
|---|---|---|---|---|---|---|---|---|---|---|---|---|---|---|
| | | | | 35 | | | | | 40 | | | | | 45 |

| Met | Lys | Thr | His | Ser | Met | Ile | Asp | Ser | Ser | Leu | Ser | Lys | Ile | Ala |
|---|---|---|---|---|---|---|---|---|---|---|---|---|---|---|
| | | | | 50 | | | | | 55 | | | | | 60 |

| Leu | Ala | Ala | Ile | Ala | Ala | Phe | Met | Ser | Ala | Val | Ile | Leu | Thr | Ala |
|---|---|---|---|---|---|---|---|---|---|---|---|---|---|---|
| | | | | 65 | | | | | 70 | | | | | 75 |

| Val | Ala | Val | Ile | Thr | Val | Gln | Leu | Arg | Arg | Gln | Tyr |
|---|---|---|---|---|---|---|---|---|---|---|---|
| | | | | 80 | | | | | 85 | | 87 |

( 2 ) INFORMATION FOR SEQ ID NO:18:

( i ) SEQUENCE CHARACTERISTICS:
    ( A ) LENGTH: 87 amino acids
    ( B ) TYPE: amino acid
    ( D ) TOPOLOGY: linear ( x i ) SEQUENCE DESCRIPTION: SEQ ID NO:18:

```
Lys  Lys  Lys  Asn  Pro  Cys  Ala  Ala  Lys  Phe  Gln  Asn  Phe  Cys  Ile
 1                  5                        10                       15

His  Gly  Glu  Cys  Arg  Tyr  Ile  Glu  Asn  Leu  Glu  Val  Val  Thr  Cys
                    20                       25                       30

His  Cys  His  Gln  Asp  Tyr  Phe  Gly  Glu  Arg  Cys  Gly  Glu  Lys  Thr
                    35                       40                       45

Met  Lys  Thr  Gln  Lys  Lys  Asp  Asp  Ser  Asp  Leu  Ser  Lys  Ile  Ala
                    50                       55                       60

Leu  Ala  Ala  Ile  Ile  Val  Phe  Val  Ser  Ala  Val  Ser  Val  Ala  Ala
                    65                       70                       75

Ile  Gly  Ile  Ile  Thr  Ala  Val  Leu  Leu  Arg  Lys  Arg
                    80                       85        87
```

( 2 ) INFORMATION FOR SEQ ID NO:19:

( i ) SEQUENCE CHARACTERISTICS:
    ( A ) LENGTH: 86 amino acids
    ( B ) TYPE: amino acid
    ( D ) TOPOLOGY: linear ( x i ) SEQUENCE DESCRIPTION: SEQ ID NO:19:

```
Lys  Lys  Arg  Asp  Pro  Cys  Leu  Arg  Lys  Tyr  Lys  Asp  Phe  Cys  Ile
 1                  5                        10                       15

His  Gly  Glu  Cys  Lys  Tyr  Val  Lys  Glu  Leu  Arg  Ala  Pro  Ser  Cys
                    20                       25                       30

Ile  Cys  His  Pro  Gly  Tyr  His  Gly  Glu  Arg  Cys  His  Gly  Leu  Ser
                    35                       40                       45

Leu  Pro  Val  Glu  Asn  Arg  Leu  Tyr  Thr  Tyr  Asp  His  Thr  Thr  Ile
                    50                       55                       60

Leu  Ala  Val  Val  Ala  Val  Val  Leu  Ser  Ser  Val  Cys  Leu  Leu  Val
                    65                       70                       75

Ile  Val  Gly  Leu  Leu  Met  Phe  Arg  Tyr  His  Arg
                    80                       85   86
```

( 2 ) INFORMATION FOR SEQ ID NO:20:

( i ) SEQUENCE CHARACTERISTICS:
    ( A ) LENGTH: 13 amino acids
    ( B ) TYPE: amino acid
    ( D ) TOPOLOGY: linear ( x i ) SEQUENCE DESCRIPTION: SEQ ID NO:20:

```
Arg  Pro  Asn  Ala  Arg  Leu  Pro  Pro  Gly  Val  Phe  Tyr  Cys
 1                  5                        10             13
```

( 2 ) INFORMATION FOR SEQ ID NO:21:

( i ) SEQUENCE CHARACTERISTICS:
    ( A ) LENGTH: 25 bases
    ( B ) TYPE: nucleic acid
    ( C ) STRANDEDNESS: single
    ( D ) TOPOLOGY: linear ( x i ) SEQUENCE DESCRIPTION: SEQ ID NO:21:

CCTCGCTCCT TCTTCTTGCC CTTCC  25

( 2 ) INFORMATION FOR SEQ ID NO:22:

( i ) SEQUENCE CHARACTERISTICS:
        ( A ) LENGTH: 496 bases
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
AA  AGA  GCC  GGC  GAG  GAG  TTC  CCC  GAA  ACT  TGT  TGG  AAC                 38
    Arg  Ala  Gly  Glu  Glu  Phe  Pro  Glu  Thr  Cys  Trp  Asn
    1              5                        10

TCC  GGG  CTC  GCG  CGG  AGG  CCA  GGA  GCT  GAG  CGG  CGG  CGG                 77
Ser  Gly  Leu  Ala  Arg  Arg  Pro  Gly  Ala  Glu  Arg  Arg  Arg
          15                  20                           25

CTG  CCG  GAC  GAT  GGG  AGC  GTG  AGC  AGG  ACG  GTG  ATA  ACC                116
Leu  Pro  Asp  Asp  Gly  Ser  Val  Ser  Arg  Thr  Val  Ile  Thr
                    30                       35

TCT  CCC  CGA  TCG  GGT  TGC  GAG  GGC  GCC  GGG  CAG  AGG  CCA                155
Ser  Pro  Arg  Ser  Gly  Cys  Glu  Gly  Ala  Gly  Gln  Arg  Pro
     40                       45                       50

GGA  CGC  GAG  CCG  CCA  GCG  GTG  GGA  CCC  ATC  GAC  GAC  TTC                194
Gly  Arg  Glu  Pro  Pro  Ala  Val  Gly  Pro  Ile  Asp  Asp  Phe
               55                       60

CCG  GGG  CGA  CAG  GAG  CAG  CCC  CGA  GAG  CCA  GGG  CGA  GCG                233
Pro  Gly  Arg  Gln  Glu  Gln  Pro  Arg  Glu  Pro  Gly  Arg  Ala
65                       70                       75

CCC  GTT  CCA  GGT  GGC  CGG  ACC  GCC  CGC  CGC  GTC  CGC  GCC                272
Pro  Val  Pro  Gly  Gly  Arg  Thr  Ala  Arg  Arg  Val  Arg  Ala
          80                       85                           90

GCG  CTC  CCT  GCA  GGC  AAC  GGG  AGA  CGC  CCC  CGC  GCA  GCG                311
Ala  Leu  Pro  Ala  Gly  Asn  Gly  Arg  Arg  Pro  Arg  Ala  Ala
                    95                      100

CGA  GCG  CCT  CAG  CGC  GGC  CGC  TCG  CTC  TCC  CCC  TCG  AGG                350
Arg  Ala  Pro  Gln  Arg  Gly  Arg  Ser  Leu  Ser  Pro  Ser  Arg
     105                      110                      115

GAC  AAA  CTT  TTC  CCA  AAC  CCG  ATC  CGA  GCC  CTT  GGA  CCA                389
Asp  Lys  Leu  Phe  Pro  Asn  Pro  Ile  Arg  Ala  Leu  Gly  Pro
               120                      125

AAC  TCG  CCT  GCG  CCG  AGA  GCC  GTC  CGC  GTA  GAG  CGC  TCC                428
Asn  Ser  Pro  Ala  Pro  Arg  Ala  Val  Arg  Val  Glu  Arg  Ser
130                      135                      140

GTC  TCC  GGC  GAG  ATG  TCC  GAG  CGC  AAA  GAA  GGC  AGA  GGC                467
Val  Ser  Gly  Glu  Met  Ser  Glu  Arg  Lys  Glu  Gly  Arg  Gly
          145                      150                      155

AAA  GGG  AAG  GGC  AAG  AAG  AAG  GAG  CGA  GG                                 496
Lys  Gly  Lys  Gly  Lys  Lys  Lys  Glu  Arg
                    160                      164
```

( 2 ) INFORMATION FOR SEQ ID NO:23:

( i ) SEQUENCE CHARACTERISTICS:
        ( A ) LENGTH: 2490 bases
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
GTGGCTGCGG   GGCAATTGAA   AAAGAGCCGG   CGAGGAGTTC   CCCGAAACTT                   50

GTTGGAACTC   CGGGCTCGCG   CGGAGGCCAG   GAGCTGAGCG   GCGGCGGCTG                  100

CCGGACGATG   GGAGCGTGAG   CAGGACGGTG   ATAACCTCTC   CCCGATCGGG                  150
```

-continued

```
TTGCGAGGGC GCCGGGCAGA GGCCAGGACG CGAGCCGCCA GCGGCGGGAC              200

CCATCGACGA CTTCCCGGGG CGACAGGAGC AGCCCCGAGA GCCAGGGCGA              250

GCGCCCGTTC CAGGTGGCCG GACCGCCCGC CGCGTCCGCG CCGCGCTCCC              300

TGCAGGCAAC GGGAGACGCC CCCGCGCAGC GCGAGCGCCT CAGCGCGGCC              350

GCTCGCTCTC CCCATCGAGG GACAAACTTT TCCCAAACCC GATCCGAGCC              400

CTTGGACCAA ACTCGCCTGC GCCGAGAGCC GTCCGCGTAG AGCGCTCCGT              450
```

| CTCCGGCGAG | ATG | TCC | GAG | CGC | AAA | GAA | GGC | AGA | GGC | AAA | 490 |
|---|---|---|---|---|---|---|---|---|---|---|---|
|  | Met | Ser | Glu | Arg | Lys | Glu | Gly | Arg | Gly | Lys |  |
|  | 1 |  |  | 5 |  |  |  |  |  | 10 |  |

| GGG | AAG | GGC | AAG | AAG | AAG | GAG | CGA | GGC | TCC | GGC | AAG | AAG | 529 |
|---|---|---|---|---|---|---|---|---|---|---|---|---|---|
| Gly | Lys | Gly | Lys | Lys | Lys | Glu | Arg | Gly | Ser | Gly | Lys | Lys |  |
|  |  |  |  | 15 |  |  |  |  | 20 |  |  |  |  |

| CCG | GAG | TCC | GCG | GCG | GGC | AGC | CAG | AGC | CCA | GCC | TTG | CCT | 568 |
|---|---|---|---|---|---|---|---|---|---|---|---|---|---|
| Pro | Glu | Ser | Ala | Ala | Gly | Ser | Gln | Ser | Pro | Ala | Leu | Pro |  |
|  | 25 |  |  |  |  | 30 |  |  |  |  | 35 |  |  |

| CCC | CAA | TTG | AAA | GAG | ATG | AAA | AGC | CAG | GAA | TCG | GCT | GCA | 607 |
|---|---|---|---|---|---|---|---|---|---|---|---|---|---|
| Pro | Gln | Leu | Lys | Glu | Met | Lys | Ser | Gln | Glu | Ser | Ala | Ala |  |
|  |  |  | 40 |  |  |  |  | 45 |  |  |  |  |  |

| GGT | TCC | AAA | CTA | GTC | CTT | CGG | TGT | GAA | ACC | AGT | TCT | GAA | 646 |
|---|---|---|---|---|---|---|---|---|---|---|---|---|---|
| Gly | Ser | Lys | Leu | Val | Leu | Arg | Cys | Glu | Thr | Ser | Ser | Glu |  |
| 50 |  |  |  |  | 55 |  |  |  |  | 60 |  |  |  |

| TAC | TCC | TCT | CTC | AGA | TTC | AAG | TGG | TTC | AAG | AAT | GGG | AAT | 685 |
|---|---|---|---|---|---|---|---|---|---|---|---|---|---|
| Tyr | Ser | Ser | Leu | Arg | Phe | Lys | Trp | Phe | Lys | Asn | Gly | Asn |  |
|  |  | 65 |  |  |  |  | 70 |  |  |  |  | 75 |  |

| GAA | TTG | AAT | CGA | AAA | AAC | AAA | CCA | CAA | AAT | ATC | AAG | ATA | 724 |
|---|---|---|---|---|---|---|---|---|---|---|---|---|---|
| Glu | Leu | Asn | Arg | Lys | Asn | Lys | Pro | Gln | Asn | Ile | Lys | Ile |  |
|  |  |  |  | 80 |  |  |  |  | 85 |  |  |  |  |

| CAA | AAA | AAG | CCA | GGG | AAG | TCA | GAA | CTT | CGC | ATT | AAC | AAA | 763 |
|---|---|---|---|---|---|---|---|---|---|---|---|---|---|
| Gln | Lys | Lys | Pro | Gly | Lys | Ser | Glu | Leu | Arg | Ile | Asn | Lys |  |
| 90 |  |  |  |  | 95 |  |  |  |  | 100 |  |  |  |

| GCA | TCA | CTG | GCT | GAT | TCT | GGA | GAG | TAT | ATG | TGC | AAA | GTG | 802 |
|---|---|---|---|---|---|---|---|---|---|---|---|---|---|
| Ala | Ser | Leu | Ala | Asp | Ser | Gly | Glu | Tyr | Met | Cys | Lys | Val |  |
|  |  | 105 |  |  |  |  | 110 |  |  |  |  |  |  |

| ATC | AGC | AAA | TTA | GGA | AAT | GAC | AGT | GCC | TCT | GCC | AAT | ATC | 841 |
|---|---|---|---|---|---|---|---|---|---|---|---|---|---|
| Ile | Ser | Lys | Leu | Gly | Asn | Asp | Ser | Ala | Ser | Ala | Asn | Ile |  |
| 115 |  |  |  |  | 120 |  |  |  |  | 125 |  |  |  |

| ACC | ATC | GTG | GAA | TCA | AAC | GAG | ATC | ATC | ACT | GGT | ATG | CCA | 880 |
|---|---|---|---|---|---|---|---|---|---|---|---|---|---|
| Thr | Ile | Val | Glu | Ser | Asn | Glu | Ile | Ile | Thr | Gly | Met | Pro |  |
|  |  | 130 |  |  |  |  | 135 |  |  |  |  | 140 |  |

| GCC | TCA | ACT | GAA | GGA | GCA | TAT | GTG | TCT | TCA | GAG | TCT | CCC | 919 |
|---|---|---|---|---|---|---|---|---|---|---|---|---|---|
| Ala | Ser | Thr | Glu | Gly | Ala | Tyr | Val | Ser | Ser | Glu | Ser | Pro |  |
|  |  |  |  | 145 |  |  |  |  | 150 |  |  |  |  |

| ATT | AGA | ATA | TCA | GTA | TCC | ACA | GAA | GGA | GCA | AAT | ACT | TCT | 958 |
|---|---|---|---|---|---|---|---|---|---|---|---|---|---|
| Ile | Arg | Ile | Ser | Val | Ser | Thr | Glu | Gly | Ala | Asn | Thr | Ser |  |
|  | 155 |  |  |  |  | 160 |  |  |  |  | 165 |  |  |

| TCA | TCT | ACA | TCT | ACA | TCC | ACC | ACT | GGG | ACA | AGC | CAT | CTT | 997 |
|---|---|---|---|---|---|---|---|---|---|---|---|---|---|
| Ser | Ser | Thr | Ser | Thr | Ser | Thr | Thr | Gly | Thr | Ser | His | Leu |  |
|  |  | 170 |  |  |  |  | 175 |  |  |  |  |  |  |

| GTA | AAA | TGT | GCG | GAG | AAG | GAG | AAA | ACT | TTC | TGT | GTG | AAT | 1036 |
|---|---|---|---|---|---|---|---|---|---|---|---|---|---|
| Val | Lys | Cys | Ala | Glu | Lys | Glu | Lys | Thr | Phe | Cys | Val | Asn |  |
| 180 |  |  |  |  | 185 |  |  |  |  | 190 |  |  |  |

| GGA | GGG | GAG | TGC | TTC | ATG | GTG | AAA | GAC | CTT | TCA | AAC | CCC | 1075 |
|---|---|---|---|---|---|---|---|---|---|---|---|---|---|
| Gly | Gly | Glu | Cys | Phe | Met | Val | Lys | Asp | Leu | Ser | Asn | Pro |  |
|  |  | 195 |  |  |  |  | 200 |  |  |  |  | 205 |  |

| TCG | AGA | TAC | TTG | TGC | AAG | TGC | CCA | AAT | GAG | TTT | ACT | GGT | 1114 |
|---|---|---|---|---|---|---|---|---|---|---|---|---|---|
| Ser | Arg | Tyr | Leu | Cys | Lys | Cys | Pro | Asn | Glu | Phe | Thr | Gly |  |
|  |  |  | 210 |  |  |  |  | 215 |  |  |  |  |  |

```
GAT CGC TGC CAA AAC TAC GTA ATG GCC AGC TTC TAC AAG              1153
Asp Arg Cys Gln Asn Tyr Val Met Ala Ser Phe Tyr Lys
    220             225             230

GCG GAG GAG CTG TAC CAG AAG AGA GTG CTG ACC ATA ACC              1192
Ala Glu Glu Leu Tyr Gln Lys Arg Val Leu Thr Ile Thr
            235             240

GGC ATC TGC ATC GCC CTC CTT GTG GTC GGC ATC ATG TGT              1231
Gly Ile Cys Ile Ala Leu Leu Val Val Gly Ile Met Cys
245             250             255

GTG GTG GCC TAC TGC AAA ACC AAG AAA CAG CGG AAA AAG              1270
Val Val Ala Tyr Cys Lys Thr Lys Lys Gln Arg Lys Lys
        260             265             270

CTG CAT GAC CGT CTT CGG CAG AGC CTT CGG TCT GAA CGA              1309
Leu His Asp Arg Leu Arg Gln Ser Leu Arg Ser Glu Arg
                275             280

AAC AAT ATG ATG AAC ATT GCC AAT GGG CCT CAC CAT CCT              1348
Asn Asn Met Met Asn Ile Ala Asn Gly Pro His His Pro
285             290             295

AAC CCA CCC CCC GAG AAT GTC CAG CTG GTG AAT CAA TAC              1387
Asn Pro Pro Pro Glu Asn Val Gln Leu Val Asn Gln Tyr
        300             305

GTA TCT AAA AAC GTC ATC TCC AGT GAG CAT ATT GTT GAG              1426
Val Ser Lys Asn Val Ile Ser Ser Glu His Ile Val Glu
310             315             320

AGA GAA GCA GAG ACA TCC TTT TCC ACC AGT CAC TAT ACT              1465
Arg Glu Ala Glu Thr Ser Phe Ser Thr Ser His Tyr Thr
        325             330             335

TCC ACA GCC CAT CAC TCC ACT ACT GTC ACC CAG ACT CCT              1504
Ser Thr Ala His His Ser Thr Thr Val Thr Gln Thr Pro
                340             345

AGC CAC AGC TGG AGC AAC GGA CAC ACT GAA AGC ATC CTT              1543
Ser His Ser Trp Ser Asn Gly His Thr Glu Ser Ile Leu
350             355             360

TCC GAA AGC CAC TCT GTA ATC GTG ATG TCA TCC GTA GAA              1582
Ser Glu Ser His Ser Val Ile Val Met Ser Ser Val Glu
        365             370

AAC AGT AGG CAC AGC AGC CCA ACT GGG GGC CCA AGA GGA              1621
Asn Ser Arg His Ser Ser Pro Thr Gly Gly Pro Arg Gly
375             380             385

CGT CTT AAT GGC ACA GGA GGC CCT CGT GAA TGT AAC AGC              1660
Arg Leu Asn Gly Thr Gly Gly Pro Arg Glu Cys Asn Ser
        390             395             400

TTC CTC AGG CAT GCC AGA GAA ACC CCT GAT TCC TAC CGA              1699
Phe Leu Arg His Ala Arg Glu Thr Pro Asp Ser Tyr Arg
                405             410

GAC TCT CCT CAT AGT GAA AGG TAT GTG TCA GCC ATG ACC              1738
Asp Ser Pro His Ser Glu Arg Tyr Val Ser Ala Met Thr
            415             420             425

ACC CCG GCT CGT ATG TCA CCT GTA GAT TTC CAC ACG CCA              1777
Thr Pro Ala Arg Met Ser Pro Val Asp Phe His Thr Pro
            430             435

AGC TCC CCC AAA TCG CCC CCT TCG GAA ATG TCT CCA CCC              1816
Ser Ser Pro Lys Ser Pro Pro Ser Glu Met Ser Pro Pro
440             445             450

GTG TCC AGC ATG ACG GTG TCC AAG CCT TCC ATG GCG GTC              1855
Val Ser Ser Met Thr Val Ser Lys Pro Ser Met Ala Val
        455             460             465

AGC CCC TTC ATG GAA GAA GAG AGA CCT CTA CTT CTC GTG              1894
Ser Pro Phe Met Glu Glu Glu Arg Pro Leu Leu Leu Val
            470             475
```

| | | | | | | | | | | | | |
|---|---|---|---|---|---|---|---|---|---|---|---|---|
| ACA | CCA | CCA | AGG | CTG | CGG | GAG | AAG | AAG | TTT | GAC | CAT | CAC | 1933
| Thr | Pro | Pro | Arg | Leu | Arg | Glu | Lys | Lys | Phe | Asp | His | His |
| | 480 | | | | | 485 | | | | | 490 | |
| CCT | CAG | CAG | TTC | AGC | TCC | TTC | CAC | CAC | AAC | CCC | GCG | CAT | 1972
| Pro | Gln | Gln | Phe | Ser | Ser | Phe | His | His | Asn | Pro | Ala | His |
| | | 495 | | | | | 500 | | | | | |
| GAC | AGT | AAC | AGC | CTC | CCT | GCT | AGC | CCC | TTG | AGG | ATA | GTG | 2011
| Asp | Ser | Asn | Ser | Leu | Pro | Ala | Ser | Pro | Leu | Arg | Ile | Val |
| 505 | | | | | 510 | | | | | 515 | | |
| GAG | GAT | GAG | GAG | TAT | GAA | ACG | ACC | CAA | GAG | TAC | GAG | CCA | 2050
| Glu | Asp | Glu | Glu | Tyr | Glu | Thr | Thr | Gln | Glu | Tyr | Glu | Pro |
| | | 520 | | | | | 525 | | | | | 530 |
| GCC | CAA | GAG | CCT | GTT | AAG | AAA | CTC | GCC | AAT | AGC | CGG | CGG | 2089
| Ala | Gln | Glu | Pro | Val | Lys | Lys | Leu | Ala | Asn | Ser | Arg | Arg |
| | | | | 535 | | | | | 540 | | | |
| GCC | AAA | AGA | ACC | AAG | CCC | AAT | GGC | CAC | ATT | GCT | AAC | AGA | 2128
| Ala | Lys | Arg | Thr | Lys | Pro | Asn | Gly | His | Ile | Ala | Asn | Arg |
| | 545 | | | | | 550 | | | | | 555 | |
| TTG | GAA | GTG | GAC | AGC | AAC | ACA | AGC | TCC | CAG | AGC | AGT | AAC | 2167
| Leu | Glu | Val | Asp | Ser | Asn | Thr | Ser | Ser | Gln | Ser | Ser | Asn |
| | | | 560 | | | | | 565 | | | | |
| TCA | GAG | AGT | GAA | ACA | GAA | GAT | GAA | AGA | GTA | GGT | GAA | GAT | 2206
| Ser | Glu | Ser | Glu | Thr | Glu | Asp | Glu | Arg | Val | Gly | Glu | Asp |
| 570 | | | | | 575 | | | | | 580 | | |
| ACG | CCT | TTC | CTG | GGC | ATA | CAG | AAC | CCC | CTG | GCA | GCC | AGT | 2245
| Thr | Pro | Phe | Leu | Gly | Ile | Gln | Asn | Pro | Leu | Ala | Ala | Ser |
| | | 585 | | | | | 590 | | | | | 595 |
| CTT | GAG | GCA | ACA | CCT | GCC | TTC | CGC | CTG | GCT | GAC | AGC | AGG | 2284
| Leu | Glu | Ala | Thr | Pro | Ala | Phe | Arg | Leu | Ala | Asp | Ser | Arg |
| | | | | 600 | | | | | 605 | | | |
| ACT | AAC | CCA | GCA | GGC | CGC | TTC | TCG | ACA | CAG | GAA | GAA | ATC | 2323
| Thr | Asn | Pro | Ala | Gly | Arg | Phe | Ser | Thr | Gln | Glu | Glu | Ile |
| | 610 | | | | | 615 | | | | | 620 | |
| CAG | GCC | AGG | CTG | TCT | AGT | GTA | ATT | GCT | AAC | CAA | GAC | CCT | 2362
| Gln | Ala | Arg | Leu | Ser | Ser | Val | Ile | Ala | Asn | Gln | Asp | Pro |
| | | | 625 | | | | | 630 | | | | |
| ATT | GCT | GTA | TAAAACCTA | AATAAACACA | TAGATTCACC | TGTAAAACTT | | | | | | | 2410
| Ile | Ala | Val | | | | | | | | | | |
| 635 | | 637 | | | | | | | | | | |

```
TATTTTATAT AATAAAGTAT TCCACCTTAA ATTAAACAAT TTATTTTATT        2460

TTAGCAGTTC TGCAAATAAA AAAAAAAAA                                2490
```

( 2 ) INFORMATION FOR SEQ ID NO:24:

( i ) SEQUENCE CHARACTERISTICS:
        ( A ) LENGTH: 1715 bases
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
GCGCCTGCCT CCAACCTGCG GGCGGGAGGT GGGTGGCTGC GGGGCAATTG        50

AAAAAGAGCC GGCGAGGAGT TCCCCGAAAC TTGTTGGAAC TCCGGGCTCG        100

CGCGGAGGCC AGGAGCTGAG CGGCGGCGGC TGCCGGACGA TGGGAGCGTG        150

AGCAGGACGG TGATAACCTC TCCCCGATCG GGTTGCGAGG GCGCCGGGCA        200

GAGGCCAGGA CGCGAGCCGC CAGCGGCGGG ACCCATCGAC GACTTCCCGG        250

GGCGACAGGA GCAGCCCCGA GAGCCAGGGC GAGCGCCCGT TCCAGGTGGC        300
```

-continued

```
CGGACCGCCC  GCCGCGTCCG  CGCCGCGCTC  CCTGCAGGCA  ACGGGAGACG                    350

CCCCCGCGCA  GCGCGAGCGC  CTCAGCGCGG  CCGCTCGCTC  TCCCCATCGA                    400

GGGACAAACT  TTTCCCAAAC  CCGATCCGAG  CCCTTGGACC  AAACTCGCCT                    450

GCGCCGAGAG  CCGTCCGCGT  AGAGCGCTCC  GTCTCCGGCG  AG      ATG                   495
                                                        Met
                                                         1

TCC  GAG  CGC  AAA  GAA  GGC  AGA  GGC  AAA  GGG  AAG  GGC  AAG               534
Ser  Glu  Arg  Lys  Glu  Gly  Arg  Gly  Lys  Gly  Lys  Gly  Lys
               5                  10

AAG  AAG  GAG  CGA  GGC  TCC  GGC  AAG  AAG  CCG  GAG  TCC  GCG               573
Lys  Lys  Glu  Arg  Gly  Ser  Gly  Lys  Lys  Pro  Glu  Ser  Ala
15                       20                       25

GCG  GGC  AGC  CAG  AGC  CCA  GCC  TTG  CCT  CCC  CAA  TTG  AAA               612
Ala  Gly  Ser  Gln  Ser  Pro  Ala  Leu  Pro  Pro  Gln  Leu  Lys
          30                       35                         40

GAG  ATG  AAA  AGC  CAG  GAA  TCG  GCT  GCA  GGT  TCC  AAA  CTA               651
Glu  Met  Lys  Ser  Gln  Glu  Ser  Ala  Ala  Gly  Ser  Lys  Leu
                    45                       50

GTC  CTT  CGG  TGT  GAA  ACC  AGT  TCT  GAA  TAC  TCC  TCT  CTC               690
Val  Leu  Arg  Cys  Glu  Thr  Ser  Ser  Glu  Tyr  Ser  Ser  Leu
          55                       60                       65

AGA  TTC  AAG  TGG  TTC  AAG  AAT  GGG  AAT  GAA  TTG  AAT  CGA               729
Arg  Phe  Lys  Trp  Phe  Lys  Asn  Gly  Asn  Glu  Leu  Asn  Arg
                    70                       75

AAA  AAC  AAA  CCA  CAA  AAT  ATC  AAG  ATA  CAA  AAA  AAG  CCA               768
Lys  Asn  Lys  Pro  Gln  Asn  Ile  Lys  Ile  Gln  Lys  Lys  Pro
80                       85                       90

GGG  AAG  TCA  GAA  CTT  CGC  ATT  AAC  AAA  GCA  TCA  CTG  GCT               807
Gly  Lys  Ser  Glu  Leu  Arg  Ile  Asn  Lys  Ala  Ser  Leu  Ala
          95                      100                      105

GAT  TCT  GGA  GAG  TAT  ATG  TGC  AAA  GTG  ATC  AGC  AAA  TTA               846
Asp  Ser  Gly  Glu  Tyr  Met  Cys  Lys  Val  Ile  Ser  Lys  Leu
                   110                      115

GGA  AAT  GAC  AGT  GCC  TCT  GCC  AAT  ATC  ACC  ATC  GTG  GAA               885
Gly  Asn  Asp  Ser  Ala  Ser  Ala  Asn  Ile  Thr  Ile  Val  Glu
120                      125                      130

TCA  AAC  GAG  ATC  ATC  ACT  GGT  ATG  CCA  GCC  TCA  ACT  GAA               924
Ser  Asn  Glu  Ile  Ile  Thr  Gly  Met  Pro  Ala  Ser  Thr  Glu
          135                      140

GGA  GCA  TAT  GTG  TCT  TCA  GAG  TCT  CCC  ATT  AGA  ATA  TCA               963
Gly  Ala  Tyr  Val  Ser  Ser  Glu  Ser  Pro  Ile  Arg  Ile  Ser
145                      150                      155

GTA  TCC  ACA  GAA  GGA  GCA  AAT  ACT  TCT  TCA  TCT  ACA  TCT              1002
Val  Ser  Thr  Glu  Gly  Ala  Asn  Thr  Ser  Ser  Ser  Thr  Ser
          160                      165                      170

ACA  TCC  ACC  ACT  GGG  ACA  AGC  CAT  CTT  GTA  AAA  TGT  GCG              1041
Thr  Ser  Thr  Thr  Gly  Thr  Ser  His  Leu  Val  Lys  Cys  Ala
                    175                      180

GAG  AAG  GAG  AAA  ACT  TTC  TGT  GTG  AAT  GGA  GGG  GAG  TGC              1080
Glu  Lys  Glu  Lys  Thr  Phe  Cys  Val  Asn  Gly  Gly  Glu  Cys
185                      190                      195

TTC  ATG  GTG  AAA  GAC  CTT  TCA  AAC  CCC  TCG  AGA  TAC  TTG              1119
Phe  Met  Val  Lys  Asp  Leu  Ser  Asn  Pro  Ser  Arg  Tyr  Leu
          200                      205

TGC  AAG  TGC  CCA  AAT  GAG  TTT  ACT  GGT  GAT  CGC  TGC  CAA              1158
Cys  Lys  Cys  Pro  Asn  Glu  Phe  Thr  Gly  Asp  Arg  Cys  Gln
210                      215                      220

AAC  TAC  GTA  ATG  GCC  AGC  TTC  TAC  AGT  ACG  TCC  ACT  CCC              1197
Asn  Tyr  Val  Met  Ala  Ser  Phe  Tyr  Ser  Thr  Ser  Thr  Pro
```

```
                    225                      230                      235
TTT CTG TCT CTG CCT GAA TAGGA GCATGCTCAG TTGGTGCTGC                                1240
Phe Leu Ser Leu Pro Glu
                240 241

TTTCTTGTTG CTGCATCTCC CCTCAGATTC CACCTAGAGC TAGATGTGTC                             1290

TTACCAGATC TAATATTGAC TGCCTCTGCC TGTCGCATGA GAACATTAAC                             1340

AAAAGCAATT GTATTACTTC CTCTGTTCGC GACTAGTTGG CTCTGAGATA                             1390

CTAATAGGTG TGTGAGGCTC CGGATGTTTC TGGAATTGAT ATTGAATGAT                             1440

GTGATACAAA TTGATAGTCA ATATCAAGCA GTGAAATATG ATAATAAAGG                             1490

CATTTCAAAG TCTCACTTTT ATTGATAAAA TAAAAATCAT TCTACTGAAC                             1540

AGTCCATCTT CTTTATACAA TGACCACATC CTGAAAAGGG TGTTGCTAAG                             1590

CTGTAACCGA TATGCACTTG AAATGATGGT AAGTTAATTT TGATTCAGAA                             1640

TGTGTTATTT GTCACAAATA AACATAATAA AAGGAGTTCA GATGTTTTC                              1690

TTCATTAACC AAAAAAAAAA AAAAA                                                        1715
```

( 2 ) INFORMATION FOR SEQ ID NO:25:

( i ) SEQUENCE CHARACTERISTICS:
    ( A ) LENGTH: 2431 bases
    ( B ) TYPE: nucleic acid
    ( C ) STRANDEDNESS: single
    ( D ) TOPOLOGY: linear ( x i ) SEQUENCE DESCRIPTION: SEQ ID NO:25:

```
GAGGCGCCTG CCTCCAACCT GCGGGCGGGA GGTGGGTGGC TGCGGGGCAA                              50

TTGAAAAAGA GCCGGCGAGG AGTTCCCCGA AACTTGTTGG AACTCCGGGC                             100

TCGCGCGGAG GCCAGGAGCT GAGCGGCGGC GGCTGCCGGA CGATGGGAGC                             150

GTGAGCAGGA CGGTGATAAC CTCTCCCCGA TCGGGTTGCG AGGGCGCCGG                             200

GCAGAGGCCA GGACGCGAGC CGCCAGCGGC GGGACCCATC GACGACTTCC                             250

CGGGGCGACA GGAGCAGCCC CGAGAGCCAG GGCGAGCGCC CGTTCCAGGT                             300

GGCCGGACCG CCCGCCGCGT CCGCGCCGCG CTCCCTGCAG GCAACGGGAG                             350

ACGCCCCCGC GCAGCGCGAG CGCCTCAGCG CGGCCGCTCG CTCTCCCCAT                             400

CGAGGGACAA ACTTTTCCCA AACCCGATCC GAGCCCTTGG ACCAAACTCG                             450

CCTGCGCCGA GAGCCGTCCG CGTAGAGCGC TCCGTCTCCG GCGAG     AT                           497
                                                      Met
                                                       1

G TCC GAG CGC AAA GAA GGC AGA GGC AAA GGG AAG GGC AAG                              537
  Ser Glu Arg Lys Glu Gly Arg Gly Lys Gly Lys Gly Lys
              5                       10

AAG AAG GAG CGA GGC TCC GGC AAG AAG CCG GAG TCC GCG                                576
Lys Lys Glu Arg Gly Ser Gly Lys Lys Pro Glu Ser Ala
 15                  20                      25

GCG GGC AGC CAG AGC CCA GCC TTG CCT CCC CAA TTG AAA                                615
Ala Gly Ser Gln Ser Pro Ala Leu Pro Pro Gln Leu Lys
         30                      35                 40

GAG ATG AAA AGC CAG GAA TCG GCT GCA GGT TCC AAA CTA                                654
Glu Met Lys Ser Gln Glu Ser Ala Ala Gly Ser Lys Leu
             45                          50

GTC CTT CGG TGT GAA ACC AGT TCT GAA TAC TCC TCT CTC                                693
Val Leu Arg Cys Glu Thr Ser Ser Glu Tyr Ser Ser Leu
     55                      60                  65

AGA TTC AAG TGG TTC AAG AAT GGG AAT GAA TTG AAT CGA                                732
```

|     |     |     |     |     |     |     |     |     |     |     |     |     |
| --- | --- | --- | --- | --- | --- | --- | --- | --- | --- | --- | --- | --- |
| Arg | Phe | Lys | Trp<br>70 | Phe | Lys | Asn | Gly<br>75 | Asn | Glu | Leu | Asn | Arg |

| AAA | AAC | AAA | CCA | CAA | AAT | ATC | AAG | ATA | CAA | AAA | AAG | CCA | 771 |
| Lys<br>80 | Asn | Lys | Pro | Gln | Asn<br>85 | Ile | Lys | Ile | Gln | Lys<br>90 | Lys | Pro | |

| GGG | AAG | TCA | GAA | CTT | CGC | ATT | AAC | AAA | GCA | TCA | CTG | GCT | 810 |
| Gly | Lys | Ser<br>95 | Glu | Leu | Arg | Ile | Asn<br>100 | Lys | Ala | Ser | Leu | Ala<br>105 | |

| GAT | TCT | GGA | GAG | TAT | ATG | TGC | AAA | GTG | ATC | AGC | AAA | TTA | 849 |
| Asp | Ser | Gly | Glu | Tyr | Met<br>110 | Cys | Lys | Val | Ile | Ser<br>115 | Lys | Leu | |

| GGA | AAT | GAC | AGT | GCC | TCT | GCC | AAT | ATC | ACC | ATC | GTG | GAA | 888 |
| Gly | Asn | Asp<br>120 | Ser | Ala | Ser | Ala<br>125 | Asn | Ile | Thr | Ile | Val<br>130 | Glu | |

| TCA | AAC | GAG | ATC | ATC | ACT | GGT | ATG | CCA | GCC | TCA | ACT | GAA | 927 |
| Ser | Asn | Glu | Ile<br>135 | Ile | Thr | Gly | Met | Pro<br>140 | Ala | Ser | Thr | Glu | |

| GGA | GCA | TAT | GTG | TCT | TCA | GAG | TCT | CCC | ATT | AGA | ATA | TCA | 966 |
| Gly<br>145 | Ala | Tyr | Val | Ser | Ser<br>150 | Glu | Ser | Pro | Ile | Arg<br>155 | Ile | Ser | |

| GTA | TCC | ACA | GAA | GGA | GCA | AAT | ACT | TCT | TCA | TCT | ACA | TCT | 1005 |
| Val | Ser | Thr<br>160 | Glu | Gly | Ala | Asn | Thr<br>165 | Ser | Ser | Ser | Thr | Ser<br>170 | |

| ACA | TCC | ACC | ACT | GGG | ACA | AGC | CAT | CTT | GTA | AAA | TGT | GCG | 1044 |
| Thr | Ser | Thr | Thr | Gly<br>175 | Thr | Ser | His | Leu | Val<br>180 | Lys | Cys | Ala | |

| GAG | AAG | GAG | AAA | ACT | TTC | TGT | GTG | AAT | GGA | GGG | GAG | TGC | 1083 |
| Glu | Lys<br>185 | Glu | Lys | Thr | Phe | Cys<br>190 | Val | Asn | Gly | Gly | Glu<br>195 | Cys | |

| TTC | ATG | GTG | AAA | GAC | CTT | TCA | AAC | CCC | TCG | AGA | TAC | TTG | 1122 |
| Phe | Met | Val | Lys<br>200 | Asp | Leu | Ser | Asn | Pro<br>205 | Ser | Arg | Tyr | Leu | |

| TGC | AAG | TGC | CCA | AAT | GAG | TTT | ACT | GGT | GAT | CGC | TGC | CAA | 1161 |
| Cys<br>210 | Lys | Cys | Pro | Asn | Glu<br>215 | Phe | Thr | Gly | Asp | Arg<br>220 | Cys | Gln | |

| AAC | TAC | GTA | ATG | GCC | AGC | TTC | TAC | AAG | GCG | GAG | GAG | CTG | 1200 |
| Asn | Tyr | Val | Met | Ala<br>225 | Ser | Phe | Tyr | Lys | Ala<br>230 | Glu | Glu | Leu<br>235 | |

| TAC | CAG | AAG | AGA | GTG | CTG | ACC | ATA | ACC | GGC | ATC | TGC | ATC | 1239 |
| Tyr | Gln | Lys | Arg | Val<br>240 | Leu | Thr | Ile | Thr | Gly<br>245 | Ile | Cys | Ile | |

| GCC | CTC | CTT | GTG | GTC | GGC | ATC | ATG | TGT | GTG | GTG | GCC | TAC | 1278 |
| Ala | Leu | Leu<br>250 | Val | Val | Gly | Ile | Met<br>255 | Cys | Val | Val | Ala<br>260 | Tyr | |

| TGC | AAA | ACC | AAG | AAA | CAG | CGG | AAA | AAG | CTG | CAT | GAC | CGT | 1317 |
| Cys | Lys | Thr | Lys<br>265 | Lys | Gln | Arg | Lys | Lys<br>270 | Leu | His | Asp | Arg | |

| CTT | CGG | CAG | AGC | CTT | CGG | TCT | GAA | CGA | AAC | AAT | ATG | ATG | 1356 |
| Leu | Arg<br>275 | Gln | Ser | Leu | Arg | Ser<br>280 | Glu | Arg | Asn | Asn | Met<br>285 | Met | |

| AAC | ATT | GCC | AAT | GGG | CCT | CAC | CAT | CCT | AAC | CCA | CCC | CCC | 1395 |
| Asn | Ile | Ala | Asn<br>290 | Gly | Pro | His | His<br>295 | Pro | Asn | Pro | Pro<br>300 | Pro | |

| GAG | AAT | GTC | CAG | CTG | GTG | AAT | CAA | TAC | GTA | TCT | AAA | AAC | 1434 |
| Glu | Asn | Val | Gln | Leu<br>305 | Val | Asn | Gln | Tyr | Val<br>310 | Ser | Lys | Asn | |

| GTC | ATC | TCC | AGT | GAG | CAT | ATT | GTT | GAG | AGA | GAA | GCA | GAG | 1473 |
| Val | Ile<br>315 | Ser | Ser | Glu | His | Ile<br>320 | Val | Glu | Arg | Glu | Ala<br>325 | Glu | |

| ACA | TCC | TTT | TCC | ACC | AGT | CAC | TAT | ACT | TCC | ACA | GCC | CAT | 1512 |

```
              Thr   Ser   Phe   Ser   Thr   Ser   His   Tyr   Thr   Ser   Thr   Ala   His
                          330                     335

CAC   TCC   ACT   ACT   GTC   ACC   CAG   ACT   CCT   AGC   CAC   AGC   TGG                    1551
His   Ser   Thr   Thr   Val   Thr   Gln   Thr   Pro   Ser   His   Ser   Trp
340                     345                                 350

AGC   AAC   GGA   CAC   ACT   GAA   AGC   ATC   CTT   TCC   GAA   AGC   CAC                    1590
Ser   Asn   Gly   His   Thr   Glu   Ser   Ile   Leu   Ser   Glu   Ser   His
            355                           360                                 365

TCT   GTA   ATC   GTG   ATG   TCA   TCC   GTA   GAA   AAC   AGT   AGG   CAC                    1629
Ser   Val   Ile   Val   Met   Ser   Ser   Val   Glu   Asn   Ser   Arg   His
                        370                     375

AGC   AGC   CCA   ACT   GGG   GGC   CCA   AGA   GGA   CGT   CTT   AAT   GGC                    1668
Ser   Ser   Pro   Thr   Gly   Gly   Pro   Arg   Gly   Arg   Leu   Asn   Gly
      380                           385                                 390

ACA   GGA   GGC   CCT   CGT   GAA   TGT   AAC   AGC   TTC   CTC   AGG   CAT                    1707
Thr   Gly   Gly   Pro   Arg   Glu   Cys   Asn   Ser   Phe   Leu   Arg   His
                  395                           400

GCC   AGA   GAA   ACC   CCT   GAT   TCC   TAC   CGA   GAC   TCT   CCT   CAT                    1746
Ala   Arg   Glu   Thr   Pro   Asp   Ser   Tyr   Arg   Asp   Ser   Pro   His
405                     410                                 415

AGT   GAA   AGG   TAAAA   CCGAAGGCAA   AGCTACTGCA   GAGGAGAAAC                                  1790
Ser   Glu   Arg
            420

TCAGTCAGAG   AATCCCTGTG   AGCACCTGCG   GTCTCACCTC   AGGAAATCTA                                  1840

CTCTAATCAG   AATAAGGGGC   GGCAGTTACC   TGTTCTAGGA   GTGCTCCTAG                                  1890

TTGATGAAGT   CATCTCTTTG   TTTGACGGAA   CTTATTTCTT   CTGAGCTTCT                                  1940

CTCGTCGTCC   CAGTGACTGA   CAGGCAACAG   ACTCTTAAAG   AGCTGGGATG                                  1990

CTTTGATGCG   GAAGGTGCAG   CACATGGAGT   TTCCAGCTCT   GGCCATGGGC                                  2040

TCAGACCCAC   TCGGGGTCTC   AGTGTCCTCA   GTTGTAACAT   TAGAGAGATG                                  2090

GCATCAATGC   TTGATAAGGA   CCCTTCTATA   ATTCCAATTG   CCAGTTATCC                                  2140

AAACTCTGAT   TCGGTGGTCG   AGCTGGCCTC   GTGTTCTTAT   CTGCTAACCC                                  2190

TGTCTTACCT   TCCAGCCTCA   GTTAAGTCAA   ATCAAGGGCT   ATGTCATTGC                                  2240

TGAATGTCAT   GGGGGGCAAC   TGCTTGCCCT   CCACCCTATA   GTATCTATTT                                  2290

TATGAAATTC   CAAGAAGGGA   TGAATAAATA   AATCTCTTGG   ATGCTGCGTC                                  2340

TGGCAGTCTT   CACGGGTGGT   TTTCAAAGCA   GAAAAAAAAA   AAAAAAAAA                                   2390

AAAAAAAAAA   AAAAAAAAA   AAAAAAAAA   AAAAAAAAA   A                                              2431

( 2 ) INFORMATION FOR SEQ ID NO:26:

( i ) SEQUENCE CHARACTERISTICS:
            ( A ) LENGTH: 625 amino acids
            ( B ) TYPE: amino acid
            ( D ) TOPOLOGY: linear ( x i ) SEQUENCE DESCRIPTION: SEQ ID NO:26:

Met   Ser   Glu   Arg   Lys   Glu   Gly   Arg   Gly   Lys   Gly   Lys   Gly   Lys   Lys
  1                     5                           10                            15

Lys   Glu   Arg   Gly   Ser   Gly   Lys   Lys   Pro   Glu   Ser   Ala   Ala   Gly   Ser
                        20                          25                            30

Gln   Ser   Pro   Ala   Leu   Pro   Pro   Arg   Leu   Lys   Glu   Met   Lys   Ser   Gln
                        35                          40                            45

Glu   Ser   Ala   Ala   Gly   Ser   Lys   Leu   Val   Leu   Arg   Cys   Glu   Thr   Ser
                        50                          55                            60

Ser   Glu   Tyr   Ser   Ser   Leu   Arg   Phe   Lys   Trp   Phe   Lys   Asn   Gly   Asn
```

|   |   |   | 65 |   |   |   | 70 |   |   |   | 75 |
|---|---|---|---|---|---|---|---|---|---|---|---|

Glu Leu Asn Arg Lys Asn Lys Pro Gln Asn Ile Lys Ile Gln Lys
                80                      85                       90

Lys Pro Gly Lys Ser Glu Leu Arg Ile Asn Lys Ala Ser Leu Ala
                95                     100                      105

Asp Ser Gly Glu Tyr Met Cys Lys Val Ile Ser Lys Leu Gly Asn
               110                     115                      120

Asp Ser Ala Ser Ala Asn Ile Thr Ile Val Glu Ser Asn Glu Ile
               125                     130                      135

Ile Thr Gly Met Pro Ala Ser Thr Glu Gly Ala Tyr Val Ser Ser
               140                     145                      150

Glu Ser Pro Ile Arg Ile Ser Val Ser Thr Glu Gly Ala Asn Thr
               155                     160                      165

Ser Ser Ser Thr Ser Thr Ser Thr Thr Gly Thr Ser His Leu Val
               170                     175                      180

Lys Cys Ala Glu Lys Glu Lys Thr Phe Cys Val Asn Gly Gly Glu
               185                     190                      195

Cys Phe Met Val Lys Asp Leu Ser Asn Pro Ser Arg Tyr Leu Cys
               200                     205                      210

Lys Cys Gln Pro Gly Phe Thr Gly Ala Arg Cys Thr Glu Asn Val
               215                     220                      225

Pro Met Lys Val Gln Asn Gln Glu Lys Ala Glu Glu Leu Tyr Gln
               230                     235                      240

Lys Arg Val Leu Thr Ile Thr Gly Ile Cys Ile Ala Leu Leu Val
               245                     250                      255

Val Gly Ile Met Cys Val Val Ala Tyr Cys Lys Thr Lys Lys Gln
               260                     265                      270

Arg Lys Lys Leu His Asp Arg Leu Arg Gln Ser Leu Arg Ser Glu
               275                     280                      285

Arg Asn Asn Met Met Asn Ile Ala Asn Gly Pro His His Pro Asn
               290                     295                      300

Pro Pro Pro Glu Asn Val Gln Leu Val Asn Gln Tyr Val Ser Lys
               305                     310                      315

Asn Val Ile Ser Ser Glu His Ile Val Glu Arg Glu Ala Glu Thr
               320                     325                      330

Ser Phe Ser Thr Ser His Tyr Thr Ser Thr Ala His His Ser Thr
               335                     340                      345

Thr Val Thr Gln Thr Pro Ser His Ser Trp Ser Asn Gly His Thr
               350                     355                      360

Glu Ser Ile Leu Ser Glu Ser His Ser Val Ile Val Met Ser Ser
               365                     370                      375

Val Glu Asn Ser Arg His Ser Ser Pro Thr Gly Gly Pro Arg Gly
               380                     385                      390

Arg Leu Asn Gly Thr Gly Gly Pro Arg Glu Cys Asn Ser Phe Leu
               395                     400                      405

Arg His Ala Arg Glu Thr Pro Asp Ser Tyr Arg Asp Ser Pro His
               410                     415                      420

Ser Glu Arg Tyr Val Ser Ala Met Thr Thr Pro Ala Arg Met Ser
               425                     430                      435

Pro Val Asp Phe His Thr Pro Ser Ser Pro Lys Ser Pro Pro Ser
               440                     445                      450

Glu Met Ser Pro Pro Val Ser Ser Met Thr Val Ser Met Pro Ser
               455                     460                      465

| Met | Ala | Val | Ser | Pro<br>470 | Phe | Met | Glu | Glu<br>475 | Arg | Pro | Leu | Leu<br>480 |
|---|---|---|---|---|---|---|---|---|---|---|---|---|
| Val | Thr | Pro | Pro | Arg<br>485 | Leu | Arg | Glu | Lys<br>490 | Phe | Asp | His | His | Pro<br>495 |
| Gln | Gln | Phe | Ser | Ser<br>500 | Phe | His | His | Asn<br>505 | Pro | Ala | His | Asp | Ser | Asn<br>510 |
| Ser | Leu | Pro | Ala | Ser<br>515 | Pro | Leu | Arg | Ile<br>520 | Val | Glu | Asp | Glu | Glu | Tyr<br>525 |
| Glu | Thr | Thr | Gln | Glu<br>530 | Tyr | Glu | Pro | Ala<br>535 | Gln | Glu | Pro | Val | Lys | Lys<br>540 |
| Leu | Ala | Asn | Ser | Arg<br>545 | Arg | Ala | Lys | Arg<br>550 | Thr | Lys | Pro | Asn | Gly | His<br>555 |
| Ile | Ala | Asn | Arg | Leu<br>560 | Glu | Val | Asp | Ser<br>565 | Asn | Thr | Ser | Ser | Gln | Ser<br>570 |
| Ser | Asn | Ser | Glu | Ser<br>575 | Glu | Thr | Glu | Asp<br>580 | Glu | Arg | Val | Gly | Glu | Asp<br>585 |
| Thr | Pro | Phe | Leu | Gly<br>590 | Ile | Gln | Asn | Pro<br>595 | Leu | Ala | Ala | Ser | Leu | Glu<br>600 |
| Ala | Thr | Pro | Ala | Phe<br>605 | Arg | Leu | Ala | Asp<br>610 | Ser | Arg | Thr | Asn | Pro | Ala<br>615 |
| Gly | Arg | Phe | Ser | Thr<br>620 | Gln | Glu | Glu | Ile | Gln<br>625 |

( 2 ) INFORMATION FOR SEQ ID NO:27:

( i ) SEQUENCE CHARACTERISTICS:
        ( A ) LENGTH: 645 amino acids
        ( B ) TYPE: amino acid
        ( D ) TOPOLOGY: linear ( x i ) SEQUENCE DESCRIPTION: SEQ ID NO:27:

| Met<br>1 | Ser | Glu | Arg | Lys<br>5 | Glu | Gly | Arg | Gly<br>10 | Lys | Gly | Lys | Gly | Lys | Lys<br>15 |
|---|---|---|---|---|---|---|---|---|---|---|---|---|---|---|
| Lys | Glu | Arg | Gly | Ser<br>20 | Gly | Lys | Lys | Pro<br>25 | Glu | Ser | Ala | Ala | Gly | Ser<br>30 |
| Gln | Ser | Pro | Ala | Leu<br>35 | Pro | Pro | Gln | Leu<br>40 | Lys | Glu | Met | Lys | Ser | Gln<br>45 |
| Glu | Ser | Ala | Ala | Gly<br>50 | Ser | Lys | Leu | Val<br>55 | Leu | Arg | Cys | Glu | Thr | Ser<br>60 |
| Ser | Glu | Tyr | Ser | Ser<br>65 | Leu | Arg | Phe | Lys<br>70 | Trp | Phe | Lys | Asn | Gly | Asn<br>75 |
| Glu | Leu | Asn | Arg | Lys<br>80 | Asn | Lys | Pro | Gln<br>85 | Asn | Ile | Lys | Ile | Gln | Lys<br>90 |
| Lys | Pro | Gly | Lys | Ser<br>95 | Glu | Leu | Arg | Ile<br>100 | Asn | Lys | Ala | Ser | Leu | Ala<br>105 |
| Asp | Ser | Gly | Glu | Tyr<br>110 | Met | Cys | Lys | Val<br>115 | Ile | Ser | Lys | Leu | Gly | Asn<br>120 |
| Asp | Ser | Ala | Ser | Ala<br>125 | Asn | Ile | Thr | Ile<br>130 | Val | Glu | Ser | Asn | Glu | Ile<br>135 |
| Ile | Thr | Gly | Met | Pro<br>140 | Ala | Ser | Thr | Glu<br>145 | Gly | Ala | Tyr | Val | Ser | Ser<br>150 |
| Glu | Ser | Pro | Ile | Arg<br>155 | Ile | Ser | Val | Ser<br>160 | Thr | Glu | Gly | Ala | Asn | Thr<br>165 |
| Ser | Ser | Ser | Thr | Ser<br>170 | Thr | Ser | Thr | Thr<br>175 | Gly | Thr | Ser | His | Leu | Val<br>180 |
| Lys | Cys | Ala | Glu | Lys | Glu | Lys | Thr | Phe | Cys | Val | Asn | Gly | Gly | Glu |

```
                        185                         190                         195
Cys Phe Met Val Lys Asp Leu Ser Asn Pro Ser Arg Tyr Leu Cys
                        200                         205                         210
Lys Cys Pro Asn Glu Phe Thr Gly Asp Arg Cys Gln Asn Tyr Val
                        215                         220                         225
Met Ala Ser Phe Tyr Lys His Leu Gly Ile Glu Phe Met Glu Ala
                        230                         235                         240
Glu Glu Leu Tyr Gln Lys Arg Val Leu Thr Ile Thr Gly Ile Cys
                        245                         250                         255
Ile Ala Leu Leu Val Val Gly Ile Met Cys Val Val Ala Tyr Cys
                        260                         265                         270
Lys Thr Lys Lys Gln Arg Lys Lys Leu His Asp Arg Leu Arg Gln
                        275                         280                         285
Ser Leu Arg Ser Glu Arg Asn Asn Met Met Asn Ile Ala Asn Gly
                        290                         295                         300
Pro His His Pro Asn Pro Pro Pro Glu Asn Val Gln Leu Val Asn
                        305                         310                         315
Gln Tyr Val Ser Lys Asn Val Ile Ser Ser Glu His Ile Val Glu
                        320                         325                         330
Arg Glu Ala Glu Thr Ser Phe Ser Thr Ser His Tyr Thr Ser Thr
                        335                         340                         345
Ala His His Ser Thr Thr Val Thr Gln Thr Pro Ser His Ser Trp
                        350                         355                         360
Ser Asn Gly His Thr Glu Ser Ile Leu Ser Glu Ser His Ser Val
                        365                         370                         375
Ile Val Met Ser Ser Val Glu Asn Ser Arg His Ser Ser Pro Thr
                        380                         385                         390
Gly Gly Pro Arg Gly Arg Leu Asn Gly Thr Gly Gly Pro Arg Glu
                        395                         400                         405
Cys Asn Ser Phe Leu Arg His Ala Arg Glu Thr Pro Asp Ser Tyr
                        410                         415                         420
Arg Asp Ser Pro His Ser Glu Arg Tyr Val Ser Ala Met Thr Thr
                        425                         430                         435
Pro Ala Arg Met Ser Pro Val Asp Phe His Thr Pro Ser Ser Pro
                        440                         445                         450
Lys Ser Pro Pro Ser Glu Met Ser Pro Pro Val Ser Ser Met Thr
                        455                         460                         465
Val Ser Met Pro Ser Met Ala Val Ser Pro Phe Met Glu Glu Glu
                        470                         475                         480
Arg Pro Leu Leu Leu Val Thr Pro Pro Arg Leu Arg Glu Lys Lys
                        485                         490                         495
Phe Asp His His Pro Gln Gln Phe Ser Phe His His Asn Pro
                        500                         505                         510
Ala His Asp Ser Asn Ser Leu Pro Ala Ser Pro Leu Arg Ile Val
                        515                         520                         525
Glu Asp Glu Glu Tyr Glu Thr Thr Gln Glu Tyr Glu Pro Ala Gln
                        530                         535                         540
Glu Pro Val Lys Lys Leu Ala Asn Ser Arg Arg Ala Lys Arg Thr
                        545                         550                         555
Lys Pro Asn Gly His Ile Ala Asn Arg Leu Glu Val Asp Ser Asn
                        560                         565                         570
Thr Ser Ser Gln Ser Ser Asn Ser Glu Ser Glu Thr Glu Asp Glu
                        575                         580                         585
```

| | | | | | | | | | | | | | | |
|---|---|---|---|---|---|---|---|---|---|---|---|---|---|---|
| Arg | Val | Gly | Glu | Asp 590 | Thr | Pro | Phe | Leu | Gly 595 | Ile | Gln | Asn | Pro | Leu 600 |
| Ala | Ala | Ser | Leu | Glu 605 | Ala | Thr | Pro | Ala | Phe 610 | Arg | Leu | Ala | Asp | Ser 615 |
| Arg | Thr | Asn | Pro | Ala 620 | Gly | Arg | Phe | Ser | Thr 625 | Gln | Glu | Glu | Ile | Gln 630 |
| Ala | Arg | Leu | Ser | Ser 635 | Val | Ile | Ala | Asn | Gln 640 | Asp | Pro | Ile | Ala | Val 645 |

( 2 ) INFORMATION FOR SEQ ID NO:28:

( i ) SEQUENCE CHARACTERISTICS:
        ( A ) LENGTH: 637 amino acids
        ( B ) TYPE: amino acid
        ( D ) TOPOLOGY: linear ( x i ) SEQUENCE DESCRIPTION: SEQ ID NO:28:

| | | | | | | | | | | | | | | |
|---|---|---|---|---|---|---|---|---|---|---|---|---|---|---|
| Met 1 | Ser | Glu | Arg | Lys 5 | Glu | Gly | Arg | Gly | Lys 10 | Gly | Lys | Gly | Lys | Lys 15 |
| Lys | Glu | Arg | Gly | Ser 20 | Gly | Lys | Lys | Pro | Glu 25 | Ser | Ala | Ala | Gly | Ser 30 |
| Gln | Ser | Pro | Ala | Leu 35 | Pro | Pro | Gln | Leu | Lys 40 | Glu | Met | Lys | Ser | Gln 45 |
| Glu | Ser | Ala | Ala | Gly 50 | Ser | Lys | Leu | Val | Leu 55 | Arg | Cys | Glu | Thr | Ser 60 |
| Ser | Glu | Tyr | Ser | Ser 65 | Leu | Arg | Phe | Lys | Trp 70 | Phe | Lys | Asn | Gly | Asn 75 |
| Glu | Leu | Asn | Arg | Lys 80 | Asn | Lys | Pro | Gln | Asn 85 | Ile | Lys | Ile | Gln | Lys 90 |
| Lys | Pro | Gly | Lys | Ser 95 | Glu | Leu | Arg | Ile | Asn 100 | Lys | Ala | Ser | Leu | Ala 105 |
| Asp | Ser | Gly | Glu | Tyr 110 | Met | Cys | Lys | Val | Ile 115 | Ser | Lys | Leu | Gly | Asn 120 |
| Asp | Ser | Ala | Ser | Ala 125 | Asn | Ile | Thr | Ile | Val 130 | Glu | Ser | Asn | Glu | Ile 135 |
| Ile | Thr | Gly | Met | Pro 140 | Ala | Ser | Thr | Glu | Gly 145 | Ala | Tyr | Val | Ser | Ser 150 |
| Glu | Ser | Pro | Ile | Arg 155 | Ile | Ser | Val | Ser | Thr 160 | Glu | Gly | Ala | Asn | Thr 165 |
| Ser | Ser | Ser | Thr | Ser 170 | Thr | Ser | Thr | Thr | Gly 175 | Thr | Ser | His | Leu | Val 180 |
| Lys | Cys | Ala | Glu | Lys 185 | Glu | Lys | Thr | Phe | Cys 190 | Val | Asn | Gly | Gly | Glu 195 |
| Cys | Phe | Met | Val | Lys 200 | Asp | Leu | Ser | Asn | Pro 205 | Ser | Arg | Tyr | Leu | Cys 210 |
| Lys | Cys | Pro | Asn | Glu 215 | Phe | Thr | Gly | Asp | Arg 220 | Cys | Gln | Asn | Tyr | Val 225 |
| Met | Ala | Ser | Phe | Tyr 230 | Lys | Ala | Glu | Glu | Leu 235 | Tyr | Gln | Lys | Arg | Val 240 |
| Leu | Thr | Ile | Thr | Gly 245 | Ile | Cys | Ile | Ala | Leu 250 | Leu | Val | Val | Gly | Ile 255 |
| Met | Cys | Val | Val | Ala 260 | Tyr | Cys | Lys | Thr | Lys 265 | Lys | Gln | Arg | Lys | Lys 270 |
| Leu | His | Asp | Arg | Leu 275 | Arg | Gln | Ser | Leu | Arg 280 | Ser | Glu | Arg | Asn | Asn 285 |
| Met | Met | Asn | Ile | Ala | Asn | Gly | Pro | His | His | Pro | Asn | Pro | Pro | Pro |

|     |     |     |     | 290 |     |     |     | 295 |     |     |     | 300 |
| --- | --- | --- | --- | --- | --- | --- | --- | --- | --- | --- | --- | --- |

Glu Asn Val Gln Leu Val Asn Gln Tyr Val Ser Lys Asn Val Ile
                  305                        310                        315

Ser Ser Glu His Ile Val Glu Arg Glu Ala Glu Thr Ser Phe Ser
                  320                        325                        330

Thr Ser His Tyr Thr Ser Thr Ala His His Ser Thr Thr Val Thr
                  335                        340                        345

Gln Thr Pro Ser His Ser Trp Ser Asn Gly His Thr Glu Ser Ile
                  350                        355                        360

Leu Ser Glu Ser His Ser Val Ile Val Met Ser Ser Val Glu Asn
                  365                        370                        375

Ser Arg His Ser Ser Pro Thr Gly Gly Pro Arg Gly Arg Leu Asn
                  380                        385                        390

Gly Thr Gly Gly Pro Arg Glu Cys Asn Ser Phe Leu Arg His Ala
                  395                        400                        405

Arg Glu Thr Pro Asp Ser Tyr Arg Asp Ser Pro His Ser Glu Arg
                  410                        415                        420

Tyr Val Ser Ala Met Thr Thr Pro Ala Arg Met Ser Pro Val Asp
                  425                        430                        435

Phe His Thr Pro Ser Ser Pro Lys Ser Pro Pro Ser Glu Met Ser
                  440                        445                        450

Pro Pro Val Ser Ser Met Thr Val Ser Lys Pro Ser Met Ala Val
                  455                        460                        465

Ser Pro Phe Met Glu Glu Glu Arg Pro Leu Leu Leu Val Thr Pro
                  470                        475                        480

Pro Arg Leu Arg Glu Lys Lys Phe Asp His His Pro Gln Gln Phe
                  485                        490                        495

Ser Ser Phe His His Asn Pro Ala His Asp Ser Asn Ser Leu Pro
                  500                        505                        510

Ala Ser Pro Leu Arg Ile Val Glu Asp Glu Glu Tyr Glu Thr Thr
                  515                        520                        525

Gln Glu Tyr Glu Pro Ala Gln Glu Pro Val Lys Lys Leu Ala Asn
                  530                        535                        540

Ser Arg Arg Ala Lys Arg Thr Lys Pro Asn Gly His Ile Ala Asn
                  545                        550                        555

Arg Leu Glu Val Asp Ser Asn Thr Ser Ser Gln Ser Ser Asn Ser
                  560                        565                        570

Glu Ser Glu Thr Glu Asp Glu Arg Val Gly Glu Asp Thr Pro Phe
                  575                        580                        585

Leu Gly Ile Gln Asn Pro Leu Ala Ala Ser Leu Glu Ala Thr Pro
                  590                        595                        600

Ala Phe Arg Leu Ala Asp Ser Arg Thr Asn Pro Ala Gly Arg Phe
                  605                        610                        615

Ser Thr Gln Glu Glu Ile Gln Ala Arg Leu Ser Ser Val Ile Ala
                  620                        625                        630

Asn Gln Asp Pro Ile Ala Val
                  635            637

( 2 ) INFORMATION FOR SEQ ID NO:29:

( i ) SEQUENCE CHARACTERISTICS:
        ( A ) LENGTH: 420 amino acids
        ( B ) TYPE: amino acid
        ( D ) TOPOLOGY: linear ( x i ) SEQUENCE DESCRIPTION: SEQ ID NO:29:

```
Met  Ser  Glu  Arg  Lys  Glu  Gly  Arg  Gly  Lys  Gly  Lys  Gly  Lys  Lys
 1              5                        10                       15

Lys  Glu  Arg  Gly  Ser  Gly  Lys  Lys  Pro  Glu  Ser  Ala  Ala  Gly  Ser
              20                       25                       30

Gln  Ser  Pro  Ala  Leu  Pro  Pro  Gln  Leu  Lys  Glu  Met  Lys  Ser  Gln
              35                       40                       45

Glu  Ser  Ala  Ala  Gly  Ser  Lys  Leu  Val  Leu  Arg  Cys  Glu  Thr  Ser
              50                       55                       60

Ser  Glu  Tyr  Ser  Ser  Leu  Arg  Phe  Lys  Trp  Phe  Lys  Asn  Gly  Asn
              65                       70                       75

Glu  Leu  Asn  Arg  Lys  Asn  Lys  Pro  Gln  Asn  Ile  Lys  Ile  Gln  Lys
              80                       85                       90

Lys  Pro  Gly  Lys  Ser  Glu  Leu  Arg  Ile  Asn  Lys  Ala  Ser  Leu  Ala
              95                      100                      105

Asp  Ser  Gly  Glu  Tyr  Met  Cys  Lys  Val  Ile  Ser  Lys  Leu  Gly  Asn
             110                      115                      120

Asp  Ser  Ala  Ser  Ala  Asn  Ile  Thr  Ile  Val  Glu  Ser  Asn  Glu  Ile
             125                      130                      135

Ile  Thr  Gly  Met  Pro  Ala  Ser  Thr  Glu  Gly  Ala  Tyr  Val  Ser  Ser
             140                      145                      150

Glu  Ser  Pro  Ile  Arg  Ile  Ser  Val  Ser  Thr  Glu  Gly  Ala  Asn  Thr
             155                      160                      165

Ser  Ser  Ser  Thr  Ser  Thr  Ser  Thr  Thr  Gly  Thr  Ser  His  Leu  Val
             170                      175                      180

Lys  Cys  Ala  Glu  Lys  Glu  Lys  Thr  Phe  Cys  Val  Asn  Gly  Gly  Glu
             185                      190                      195

Cys  Phe  Met  Val  Lys  Asp  Leu  Ser  Asn  Pro  Ser  Arg  Tyr  Leu  Cys
             200                      205                      210

Lys  Cys  Pro  Asn  Glu  Phe  Thr  Gly  Asp  Arg  Cys  Gln  Asn  Tyr  Val
             215                      220                      225

Met  Ala  Ser  Phe  Tyr  Lys  Ala  Glu  Glu  Leu  Tyr  Gln  Lys  Arg  Val
             230                      235                      240

Leu  Thr  Ile  Thr  Gly  Ile  Cys  Ile  Ala  Leu  Leu  Val  Val  Gly  Ile
             245                      250                      255

Met  Cys  Val  Val  Ala  Tyr  Cys  Lys  Thr  Lys  Lys  Gln  Arg  Lys  Lys
             260                      265                      270

Leu  His  Asp  Arg  Leu  Arg  Gln  Ser  Leu  Arg  Ser  Glu  Arg  Asn  Asn
             275                      280                      285

Met  Met  Asn  Ile  Ala  Asn  Gly  Pro  His  His  Pro  Asn  Pro  Pro  Pro
             290                      295                      300

Glu  Asn  Val  Gln  Leu  Val  Asn  Gln  Tyr  Val  Ser  Lys  Asn  Val  Ile
             305                      310                      315

Ser  Ser  Glu  His  Ile  Val  Glu  Arg  Glu  Ala  Glu  Thr  Ser  Phe  Ser
             320                      325                      330

Thr  Ser  His  Tyr  Thr  Ser  Thr  Ala  His  His  Ser  Thr  Thr  Val  Thr
             335                      340                      345

Gln  Thr  Pro  Ser  His  Ser  Trp  Ser  Asn  Gly  His  Thr  Glu  Ser  Ile
             350                      355                      360

Leu  Ser  Glu  Ser  His  Ser  Val  Ile  Val  Met  Ser  Ser  Val  Glu  Asn
             365                      370                      375

Ser  Arg  His  Ser  Ser  Pro  Thr  Gly  Gly  Pro  Arg  Gly  Arg  Leu  Asn
             380                      385                      390

Gly  Thr  Gly  Gly  Pro  Arg  Glu  Cys  Asn  Ser  Phe  Leu  Arg  His  Ala
```

|  | | | | | | | | | | | | 395 | | | | 400 | | | | 405 | |
|---|---|---|---|---|---|---|---|---|---|---|---|---|---|---|---|---|---|---|---|---|---|
| Arg | Glu | Thr | Pro | Asp | Ser | Tyr | Arg | Asp | Ser | Pro | His | Ser | Glu | Arg |
| | | | | 410 | | | | | 415 | | | | | 420 |

(2) INFORMATION FOR SEQ ID NO:30:

(i) SEQUENCE CHARACTERISTICS:
        (A) LENGTH: 241 amino acids
        (B) TYPE: amino acid
        (D) TOPOLOGY: linear (xi) SEQUENCE DESCRIPTION: SEQ ID NO:30:

| Met | Ser | Glu | Arg | Lys | Glu | Gly | Arg | Gly | Lys | Gly | Lys | Gly | Lys | Lys |
|---|---|---|---|---|---|---|---|---|---|---|---|---|---|---|
| 1 | | | | 5 | | | | | 10 | | | | | 15 |
| Lys | Glu | Arg | Gly | Ser | Gly | Lys | Lys | Pro | Glu | Ser | Ala | Ala | Gly | Ser |
| | | | | 20 | | | | | 25 | | | | | 30 |
| Gln | Ser | Pro | Ala | Leu | Pro | Pro | Gln | Leu | Lys | Glu | Met | Lys | Ser | Gln |
| | | | | 35 | | | | | 40 | | | | | 45 |
| Glu | Ser | Ala | Ala | Gly | Ser | Lys | Leu | Val | Leu | Arg | Cys | Glu | Thr | Ser |
| | | | | 50 | | | | | 55 | | | | | 60 |
| Ser | Glu | Tyr | Ser | Ser | Leu | Arg | Phe | Lys | Trp | Phe | Lys | Asn | Gly | Asn |
| | | | | 65 | | | | | 70 | | | | | 75 |
| Glu | Leu | Asn | Arg | Lys | Asn | Lys | Pro | Gln | Asn | Ile | Lys | Ile | Gln | Lys |
| | | | | 80 | | | | | 85 | | | | | 90 |
| Lys | Pro | Gly | Lys | Ser | Glu | Leu | Arg | Ile | Asn | Lys | Ala | Ser | Leu | Ala |
| | | | | 95 | | | | | 100 | | | | | 105 |
| Asp | Ser | Gly | Glu | Tyr | Met | Cys | Lys | Val | Ile | Ser | Lys | Leu | Gly | Asn |
| | | | | 110 | | | | | 115 | | | | | 120 |
| Asp | Ser | Ala | Ser | Ala | Asn | Ile | Thr | Ile | Val | Glu | Ser | Asn | Glu | Ile |
| | | | | 125 | | | | | 130 | | | | | 135 |
| Ile | Thr | Gly | Met | Pro | Ala | Ser | Thr | Glu | Gly | Ala | Tyr | Val | Ser | Ser |
| | | | | 140 | | | | | 145 | | | | | 150 |
| Glu | Ser | Pro | Ile | Arg | Ile | Ser | Val | Ser | Thr | Glu | Gly | Ala | Asn | Thr |
| | | | | 155 | | | | | 160 | | | | | 165 |
| Ser | Ser | Ser | Thr | Ser | Thr | Ser | Thr | Thr | Gly | Thr | Ser | His | Leu | Val |
| | | | | 170 | | | | | 175 | | | | | 180 |
| Lys | Cys | Ala | Glu | Lys | Glu | Lys | Thr | Phe | Cys | Val | Asn | Gly | Gly | Glu |
| | | | | 185 | | | | | 190 | | | | | 195 |
| Cys | Phe | Met | Val | Lys | Asp | Leu | Ser | Asn | Pro | Ser | Arg | Tyr | Leu | Cys |
| | | | | 200 | | | | | 205 | | | | | 210 |
| Lys | Cys | Pro | Asn | Glu | Phe | Thr | Gly | Asp | Arg | Cys | Gln | Asn | Tyr | Val |
| | | | | 215 | | | | | 220 | | | | | 225 |
| Met | Ala | Ser | Phe | Tyr | Ser | Thr | Ser | Thr | Pro | Phe | Leu | Ser | Leu | Pro |
| | | | | 230 | | | | | 235 | | | | | 240 |
| Glu | | | | | | | | | | | | | | |
| 241 | | | | | | | | | | | | | | |

NUCLEIC ACIDS, VECTORS AND HOST CELLS ENCODING HEREGULIN

CROSS REFERENCES

This application is a divisional of U.S. Ser. No. 08/126,145 filed 23 Sep. 1993, which application is a continuation of U.S. Ser. No. 07/880,917 filed 11 May 1992 (now abandoned), which application is a continuation-in-part of U.S. Ser. No. 07/847,743 filed 06 Mar. 1992 (issued as U.S. Pat. No. 5,367,060 on 22 Nov. 1994), which application is a continuation-in-part of U.S. Ser. No. 07/790,801 filed 08 Nov. 1991 (now abandoned), which application is a continuation-in-part of U.S. Ser. No. 07/765,212 filed 25 Sep. 1991 (now abandoned), which application is a continuation-in-part of U.S. Ser. No. 07/705,256 filed 24 May 1991 (now abandoned).

BACKGROUND OF THE INVENTION

1. Field of the Invention

This invention relates to polypeptide ligands that bind to receptors implicated in cellular growth. In particular, it relates to polypeptide ligands that bind to the p185$^{HER2}$ receptor.

2. Description of Background and Related Art

Cellular protooncogenes encode proteins that are thought to regulate normal cellular proliferation and differentiation. Alterations in their structure or amplification of their expression lead to abnormal cellular growth and have been associated with carcinogenesis (Bishop J M, *Science* 235: 305–311 [1987]); (Rhims J S, *Cancer Detection and Prevention* 11: 139–149 [1988]); (Nowell P C, *Cancer Res.* 46: 2203–2207 [1986]); (Nicolson G L, *Cancer Res.* 47: 1473–1487 [1987]). Protooncogenes were first identified by either of two approaches. First, molecular characterization of the genomes of transforming retroviruses showed that the genes responsible for the transforming ability of the virus in many cases were altered versions of genes found in the genomes of normal cells. The normal version is the protooncogene, which is altered by mutation to give rise to the oncogene. An example of such a gene pair is represented by the EGF receptor and the v-erb-B gene product. The virally encoded v-erb-B gene product has suffered truncation and other alterations that render it constitutively active and endow it with the ability to induce cellular transformation (Yarden et al., *Ann. Rev. Biochem.* 57: 443–478, 1988).

The second method for detecting cellular transforming genes that behave in a dominant fashion involves transfection of cellular DNA from tumor cells of various species into nontransformed target cells of a heterologous species. Most often this was done by transfection of human, avian, or rat DNAs into the murine NIH 3T3 cell line (Bishop J M, *Science* 235: 305–311 [1987]); (Rhims J S, *Cancer Detection and Prevention* 11: 139–149 [1988]); (Nowell P C, *Cancer. Res.* 46: 2203–2207 [1986]); (Nicolson G L, *Cancer. Res.* 47: 1473–1487 [1987]); (Yarden et al., *Ann. Rev. Biochem.* 57: 443–478 [19881]. Following several cycles of genomic DNA isolation and retransfection, the human or other species DNA was molecularly cloned from the murine background and subsequently characterized. In some cases, the same genes were isolated following transfection and cloning as those identified by the direct characterization of transforming viruses. In other cases, novel oncogenes were identified. An example of a novel oncogene identified by this transfection assay is the neu oncogene. It was discovered by Weinberg and colleagues in a transfection experiment in which the initial DNA was derived from a carcinogen-induced rat neuroblastoma (Padhy et al., *Cell* 28: 865–871 [1982]); (Schechter et al., *Nature* 312: 513–516 [1984]). Characterization of the rat neu oncogene revealed that it had the structure of a growth factor receptor tyrosine kinase, had homology to the EGF receptor, and differed from its normal counterpart, the neu protooncogene, by an activating mutation in its transmembrane domain (Bargmann et al., *Cell* 45: 649–657 [1986]). The human counterpart to neu is the HER2 protooncogene, also designated c-erb- B2 (Coussens et al., *Science* 230: 1137–1139 [1985]); U.S. Ser. No. 07/143,912).

The association of the HER2 protooncogene with cancer was established by yet a third approach, that is, its association with human breast cancer. The HER2 protooncogene was first discovered in cDNA libraries by virtue of its homology with the EGF receptor, with which it shares structural similarities throughout (Yarden et al., *Ann. Rev. Biochem.* 57: 443–478 [1988]). When radioactive probes derived from the cDNA sequence encoding p185$^{HER2}$ were used to screen DNA samples from breast cancer patients, amplification of the HER2 protooncogene was observed in about 30% of the patient samples (Slamon et al., *Science* 235: 177–182 [1987]). Further studies have confirmed this original observation and extended it to suggest an important correlation between HER2 protooncogene amplification and/or overexpression and worsened prognosis in ovarian cancer and non-small cell lung cancer (Slamon et al., *Science* 244: 707–712 [1989]); (Wright et al., *Cancer Res* 49: 2087–2090, 1989); (Paik et al., *J. Clin. Oncology* 8: 103–112 [1990]); (Berchuck et al., *Cancer Res.* 50: 4087–4091, 1990); (Kern et al., *Cancer Res.* 50: 5184–5191, 1990).

The association of HER2 amplification/overexpression with aggressive malignancy, as described above, implies that it may have an Important role in progression of human cancer; however, many tumor-related cell surface antigens have been described in the past, few of which appear to have a direct role in the genesis or progression of disease (Schlom et al. *Cancer Res.* 50: 820–827, 1990); (Szala et al., *Proc. Natl. Acad. Sci.* 98: 3542–3546).

Among the protooncogenes are those that encode cellular growth factors which act through endoplasmic kinase phosphorylation of cytoplasmic protein. The HER1 gene (or erb-B1) encodes the epidermal growth factor (EGF) receptor. The β-chain of platelet-derived growth factor is encoded by the c-sis gene. The granulocyte-macrophage colony stimulating factor is encoded by the c-fms gene. The neu protooncogene has been identified in ethylnitrosourea-induced rat neuroblastomas. The HER2 gene encodes the 1,255 amino acid tyrosine kinase receptor-like glycoprotein p185$^{HER2}$ that has homology to the human epidermal growth factor receptor.

The known receptor tyrosine kinases all have the same general structural motif: an extracellular domain that binds ligand, and an intracellular tyrosine kinase domain that is necessary for signal transduction and transformation. These two domains are connected by a single stretch of approximately 20 mostly hydrophobic amino acids, called the transmembrane spanning sequence. This transmembrane spanning sequence is thought to play a role in transferring the signal generated by ligand binding from the outside of the cell to the inside. Consistent with this general structure, the human p185$^{HER2}$ glycoprotein, which is located on the cell surface, may be divided into three principal portions: an extracellular domain, or ECD (also known as XCD); a transmembrane spanning sequence; and a cytoplasmic, intracellular tyrosine kinase domain. While it is presumed that the extracellular domain is a ligand receptor, the p185$^{HER2}$ ligand has not yet been positively identified.

No specific ligand binding to p185$^{HER2}$ has been identified, although Lupu et al., (Science 249: 1552–1555, 1989) describe an inhibitory 30 kDa glycoprotein secreted from human breast cancer cells which is alleged to be a putative ligand for p185$^{HER2}$. Lupu et al., Science, 249: 1552–1555 (1990); Proceedings of the American Assoc. for Cancer Research, Vol 32, Abs 297, March 1991) reported the purification of a 30 kD factor from MDA-MB-231 cells and a 75 kD factor from SK-BR-3 cells that stimulates p185$^{HER2}$. The 75 kD factor reportedly induced phosphorylation of p185$^{HER2}$ and modulated cell proliferation and colony formation of SK-BR-3 cells overexpressing the p185$^{HER2}$ receptor. The 30 kD factor competes with muMab 4D5 for binding to p185$^{HER2}$, its growth effect on SK-BR-3 cells was dependent on 30 kD concentration (stimulatory at low concentrations and inhibitory at higher concentrations). Furthermore, it stimulated the growth of MDA-MB-468 cells (EGF-R positive, p185$^{HER2}$ negative), it stimulated phosphosylation of the EGF receptor and it could be obtained from SK-BR-3 cells. In the rat neu system, Yarden et al., (Biochemistry, 30: 3543–3550, 1991) describe a 35 kDa glycoprotein candidate ligand for the neu encoded receptor secreted by ras transformed fibroblasts. Dobashi et al., Proc. Natl. Acad. Sci. USA, 88: 8582–8586 (1991); Biochem. Biophys. Res. Commun.; 179: 1536–1542 (1991) described a neu protein-specific activating factor (NAF) which is secreted by human T-cell line ATL-2 and which has a molecular weight in the range of 8–24 kD. A 25 kD ligand from activated macrophages was also described (Tarakhovsky, et al., J. Cancer Res., 2188–2196 (1991).

Methods for the in vivo assay of tumors using HER2 specific monoclonal antibodies and methods of treating tumor cells using HER2 specific monoclonal antibodies are described in U.S. Ser. No. 07/143,912.

There is a current and continuing need in the art to identify the actual ligand or ligands that activate p185$^{HER2}$, and to identify their biological role(s), including their roles in cell-growth and differentiation, cell-transformation and the creation of malignant neoplasms.

Accordingly, it is an object of this invention to identify and purify one or more novel p185$^{HER2}$ ligand polypeptide (s) that bind and stimulate p185$^{HER2}$.

It is another object to provide nucleic acid encoding novel p185$^{HER2}$ binding ligand polypeptides and to use this nucleic acid to produce a p185$^{HER2}$ binding ligand polypeptide in recombinant cell culture for therapeutic or diagnostic use, and for the production of therapeutic antagonists for use in certain metabolic disorders including, but not necessarily restricted to the killing, inhibition and/or diagnostic imaging of tumors and tumorigenic cells.

It is a further object to provide derivatives and modified forms of novel glycoprotein ligands, including amino acid sequence variants, fusion polypeptides combining a p185$^{HER2}$ binding ligand and a heterologous protein and covalent derivatives of a p185$^{HER2}$ binding ligand.

It is an additional object to prepare immunogens for raising antibodies against p185$^{HER2}$ binding ligands, as well as to obtain antibodies capable of binding to such ligands, and antibodies which bind a p185$^{HER2}$ binding ligand and prevent the ligand from activating p185$^{HER2}$. It is a further object to prepare immunogens comprising a p185$^{HER2}$ binding ligand fused with an immunogenic heterologous polypeptide.

These and other objects of the invention will be apparent to the ordinary artisan upon consideration of the specification as a whole.

SUMMARY OF THE INVENTION

In accordance with the objects of this invention, we have identified and isolated novel ligand families which bind to p185$^{HER2}$. These ligands are denominated the heregulin (HRG) polypeptides, and include HRG-α, HRG-β1, HRG-β2, HRG-β3 and other HRG polypeptides which cross-react with antibodies directed against these family members and/ or which are substantially homologous as defined infra. A preferred HRG is the ligand disclosed in FIG. 4 and its fragments, further designated HRG-α. Other preferred HRGs are the ligands and their fragments disclosed in FIG. 8, and designated HRG-β1, HRG-β2 disclosed in FIG. 12, and HRG-β3 disclosed in FIG. 13.

In another aspect, the invention provides a composition comprising HRG which is isolated from its source environment, in particular HRG that is free of contaminating human polypeptides. HRG is purified by absorption to heparin sepharose, cation (e.g. polyaspartic acid) exchange resins, and reversed phase HPLC.

HRG or HRG fragments (which also may be synthesized by in vitro methods) are fused (by recombinant expression or an in vitro peptidyl bond) to an immunogenic polypeptide and this fusion polypeptide, in turn, is used to raise antibodies against an HRG epitope. Anti-HRG antibodies are recovered from the serum of immunized animals. Alternatively, monoclonal antibodies are prepared from cells in vitro or from in vivo immunized animals in conventional fashion. Preferred antibodies identified by routine screening will bind to HRG, but will not substantially cross-react with any other known ligands such as EGF, and will prevent HRG from activating p185$^{HER2}$. In addition, anti-HRG antibodies are selected that are capable of binding specifically to Individual family members of the HRG family, e.g. HRG-α, HRG-β1, HRG-β2, HRG-β3, and thereby may act as specific antagonists thereof.

HRG also is derivatized in vitro to prepare immobilized HRG and labeled HRG, particularly for purposes of diagnosis of HRG or its antibodies, or for affinity purification of HRG antibodies. Immobilized anti-HRG antibodies are useful in the diagnosis (in vitro or In vivo) or purification of HRG. In one preferred embodiment, a mixture of HRG and other peptides is passed over a column to which the anti-HRG antibodies are bound.

Substitutional, deletional, or insertional variants of HRG are prepared by in vitro or recombinant methods and screened, for example, for immuno-crossreactivity with the native forms of HRG and for HRG antagonist or agonist activity.

In another preferred embodiment, HRG is used for stimulating the activity of p185$^{HER2}$ in normal cells. In another preferred embodiment, a variant of HRG is used as an antagonist to inhibit stimulation of p185$^{HER2}$.

HRG, its derivatives, or its antibodies are formulated into physiologically acceptable vehicles, especially for therapeutic use. Such vehicles include sustained-release formulations of HRG or HRG variants. A composition is also provided comprising HRG and a pharmaceutically acceptable carrier, and an isolated polypeptide comprising HRG fused to a heterologous polypeptide.

In still other aspects, the invention provides an isolated nucleic acid encoding an HRG, which nucleic acid may be labeled or unlabeled with a detectable moiety, and a nucleic acid sequence that is complementary, or hybridizes under stringent conditions to, a nucleic acid sequence encoding an HRG.

The nucleic acid sequence is also useful in hybridization assays for HRG nucleic acid and in a method of determining the presence of an HRG, comprising hybridizing the DNA (or RNA) encoding (or complementary to) an HRG to a test sample nucleic acid and determining the presence of an HRG. The invention also provides a method of amplifying a nucleic acid test sample comprising priming a nucleic acid polymerase (chain) reaction with nucleic acid (DNA or RNA) encoding (or complementary to) a HRG.

In still further aspects, the nucleic acid is DNA and further comprises a replicable vector comprising the nucleic acid encoding an HRG operably linked to control sequences recognized by a host transformed by the vector; host cells transformed with the vector; and a method of using a nucleic acid encoding an HRG to effect the production of HRG, comprising expressing HRG nucleic acid In a culture of the transformed host cells and recovering an HRG from the host cell culture.

In further embodiments, the invention provides a method for producing HRG comprising inserting into the DNA of a cell containing the nucleic acid encoding an HRG a transcription modulatory element in sufficient proximity and orientation to an HRG nucleic acid to influence (suppress or stimulate) transcription thereof, with an optional further step comprising culturing the cell containing the transcription modulatory element and an HRG nucleic acid.

In still further embodiments, the invention provides a cell comprising the nucleic acid encoding an HRG and an exogenous transcription modulatory element in sufficient proximity and orientation to an HRG nucleic acid to influence transcription thereof; and a host cell containing the nucleic acid encoding an HRG operably linked to exogenous control sequences recognized by the host cell.

PolyAspartic acid column chromography of heregulin-α was conducted and the elution profile of proteins measured at $A_{214}$. The 0.6M NaCl pool from the heparin Sepharose purification step was diluted to 0.2M NaCl with water and loaded onto the polyaspartic acid column equilibrated in 17 mM Na phosphate, pH 6.8 with 30% ethanol. A linear NaCl gradient from 0.3 to 0.6M was initiated at 0 time and was complete at 30 minutes. Fractions were tested in HRG tyrosine autophosphorylation assay. The fractions corresponding to peak C were pooled for further purification on C4 reversed phase HPLC.

Figure 2A:
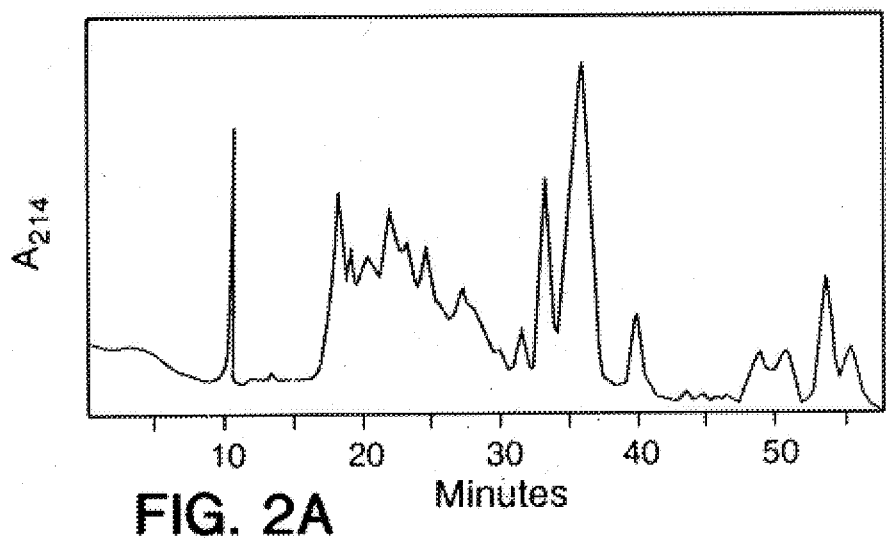
Figure 2B:
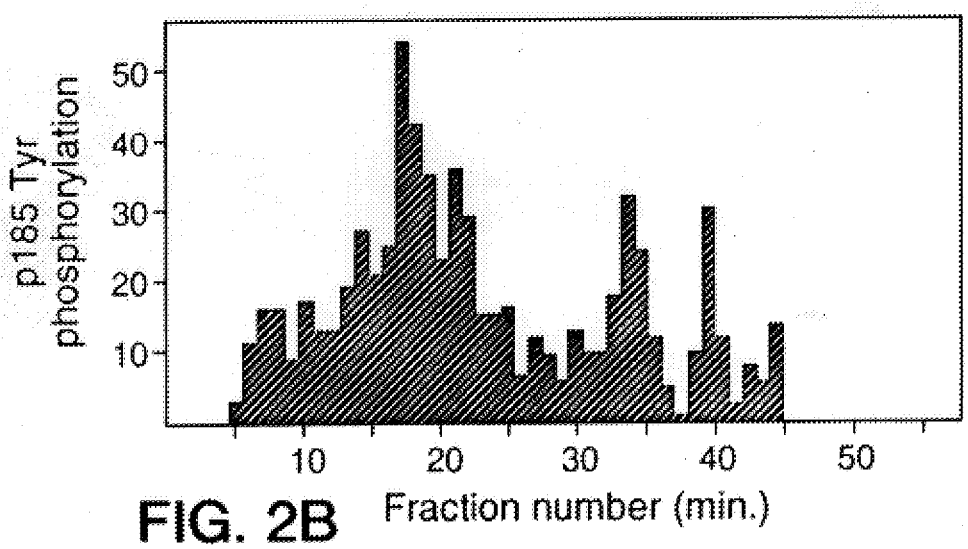
Figure 2C:
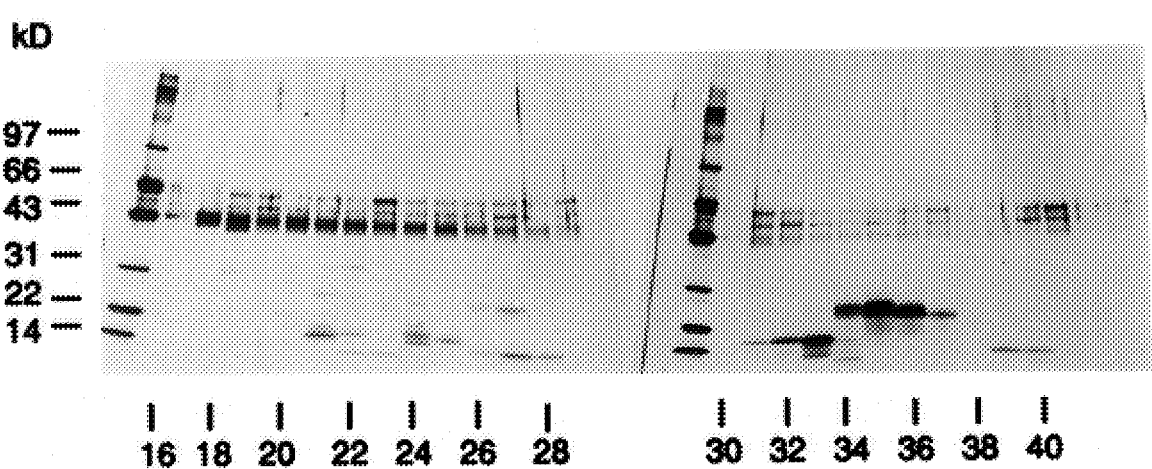

FIG. 2A–2C C4 Reversed Phase Purification of Heregulin-2.

Panel A: Pool C from the polyaspartic acid column was applied to a C4 HPLC column (SynChropak RP-4) equilibrated in 0.1% TFA and the proteins eluted with a linear acetonitrile gradient at 0.25%/minute. The absorbance trace for the run numbered C4–17 is shown. One milliliter fractions were collected for assay.

Panel B: Ten microliter aliquots of the fractions were tested in HRG tyrosine autophosphorylation assay. Levels of phosphotyrosine in the $p185^{HER2}$ protein were quantitated by a specific antiphosphotyrosine antibody and displayed in arbitrary units on the abscissa.

Panel C: Ten microliter fractions were taken and subjected to SDS gel electrophoresis on 4–20% acrylamide gradient gels according to the procedure of Laemmli (Nature, 227: 680–685, 1970). The molecular weights of the standard proteins are indicated to the left of the lane containing the standards. The major peak of tyrosine phosphorylation activity found in fraction 17 was associated with a prominent 45,000 Da band (HRG-α).

Figure 3:
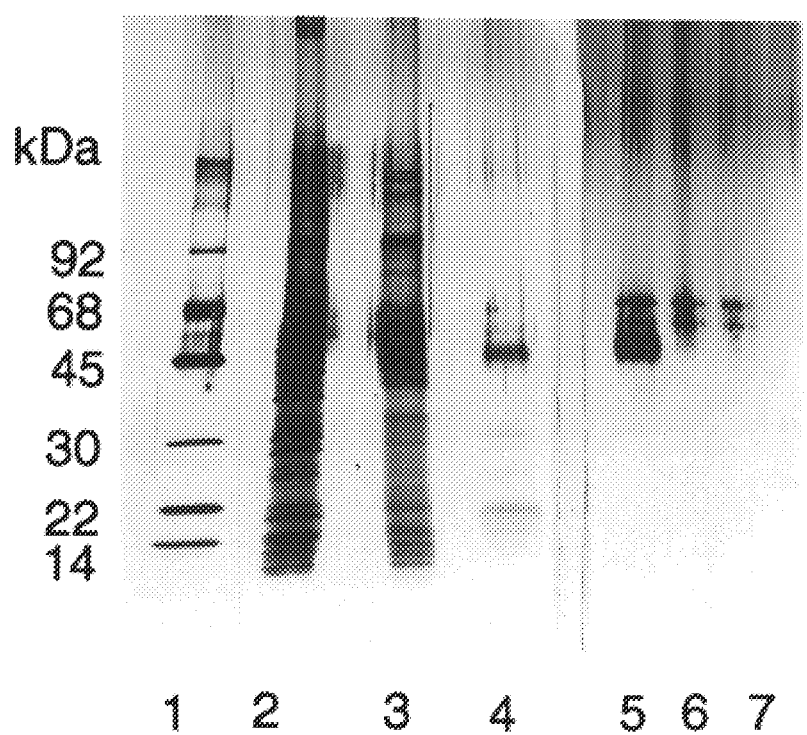

FIG. 3. SDS Polyacrylamide Gel Showing Purification of Heregulin-α.

Molecular weight markers are shown in Lane 1. Aliquots from the MDA-MB-231 conditioned media (Lane 2), the 0.6M NaCl pool from the heparin Sepharose column (Lane 3), Pool C from the polyaspartic acid column (Lane 4) and Fraction 17 from the HPLC column (C4–17) (Lane 5) were electrophoresed on a 4–20% gradient gel and silver stained. Lanes 6 and 7 contained buffer only and shows the presence of gel artifacts in the 50–65 KDa molecular weight region.

FIGS. 4a–4d depict the deduced amino acid sequence of the cDNA contained in $\lambda gt_{10}her16$ (SEQ ID NO: 12 and SEQ ID NO: 13). The nucleotides are numbered at the top left of each line and the amino acids written in three letter code are numbered at the bottom left of each line. The nucleotide sequence corresponding to the probe is nucleotides 681–720. The probable transmembrane domain is amino acids 287–309. The six cysteines of the EGF motif are 226, 234, 240, 254, 256 and 265. The five potential three-amino acid N-linked glycosylation sites are 164–166, 170–172, 208–210, 437–439 and 609–611. The serine-threonine potential O-glycosylation sites are 209–221. Serine-glycine dipeptide potential glycosaminoglycan addition sites are amino acids 42–43, 64–65 and 151–152. The initiating methionine(MET) is at position #45 of FIG. 4 although the processed N-terminal residue is S46.

Figure 5:
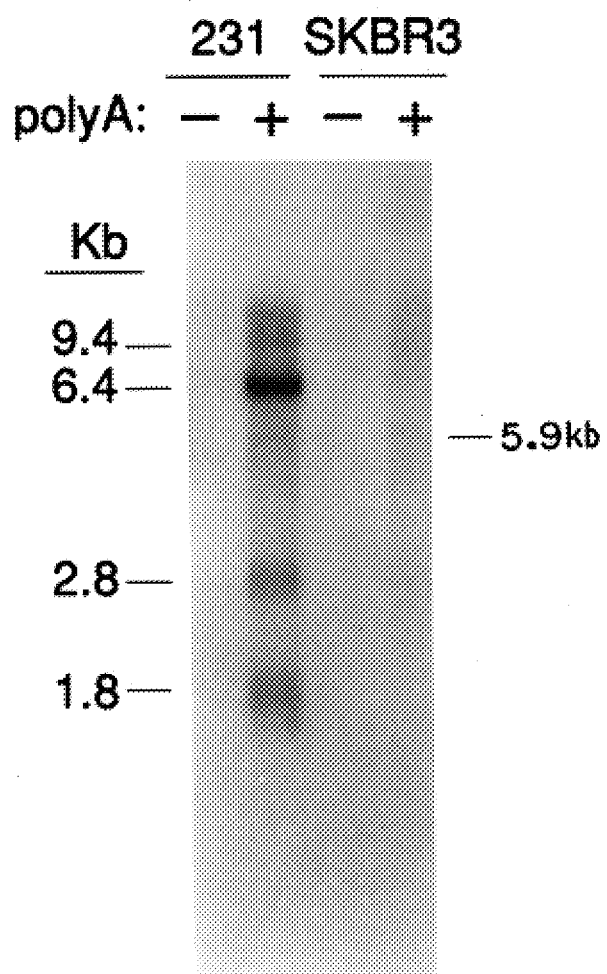

FIG. 5 Northern blot analysis of MDA-MB-231 and SKBR3 RNAs

Labeled from left to right are the following: 1) MDA-MB-231 polyA minus-RNA, (RNA remaining after polyA-containing RNA is removed); 2) MDA-MB-231 polyA plus-mRNA (RNA which contains polyA); 3) SKBR3 polyA minus-RNA; and, 4) SKBR3 polyA plus-mRNA. The probe used for this analysis was a radioactively (32p) labelled internal xho1 DNA restriction endonuclease fragment from the cDNA portion of λgt10her16.

FIG. 6 Sequence Comparisons in the EGF Family of Proteins.

Sequences of several EGF-like proteins (SEQ ID NOS: 14, 15, 16, 17, 18, and 19) around the cysteine domain are aligned with the sequence of HRG-α. The location in FIG. 6 of the cysteines and the invariant glycine and arginine residues at positions 238 and 264 clearly show that HRG-α is a member of the EGF family. The region in FIG. 6 of highest amino acid identity of the family members relative to HRG-α (30–40%) is found between Cys 234 and Cys 265. The strongest identity (40%) is with the heparin-binding EGF (HB-EGF) species. HRG-A has a unique 3 amino acid insert between Cys 240 and Cys 254. Potential transmembrane domains are boxed (287–309). Bars indicate the carboxy-terminal sites for EGF and TGF-alpha where proteolytic cleavage detaches the mature growth factors from their transmembrane associated proforms. HB-EGF is heparin binding-epidermal growth factor; EGF is epidermal growth factor; TGF-alpha is transforming growth factor alpha; and schwannoma is the schwannoma-derived growth factor. The residue numbers in FIG. 6 reflect the FIG. 4 convention.

Figure 7:
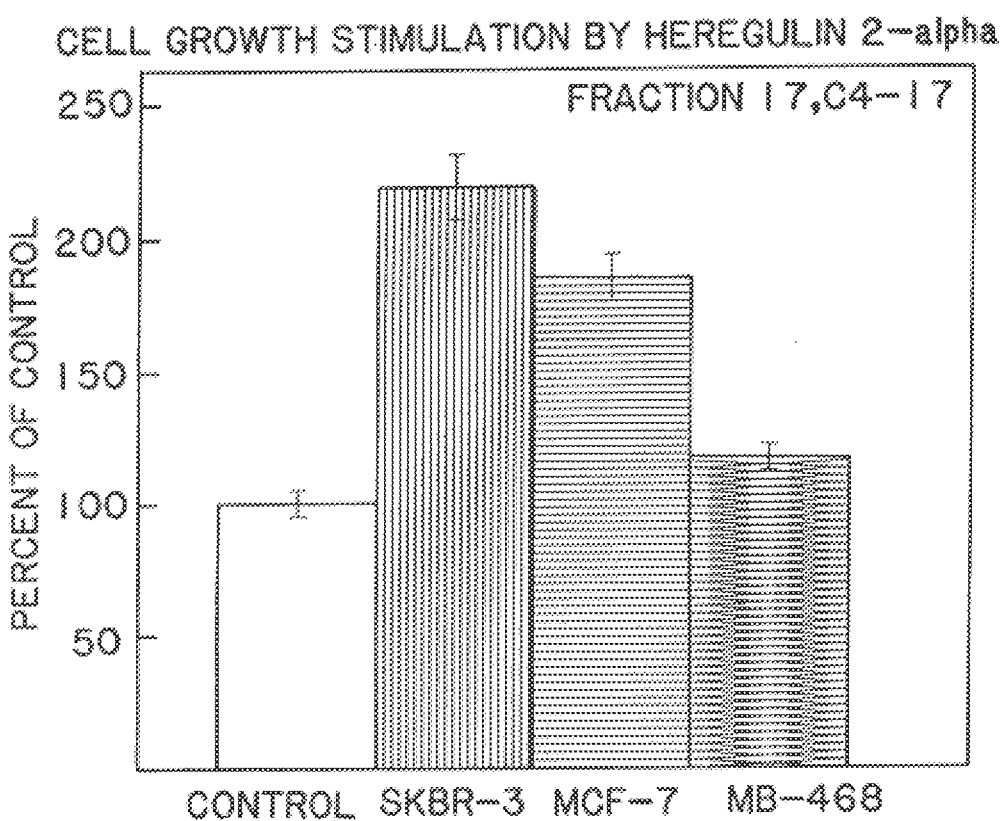

FIG. 7 Stimulation of Cell Growth by HRG-α.

Three different cell lines were tested for growth responses to 1 nM HRG-α. Cell protein was quantitated by crystal violet staining and the responses normalized to control, untreated cells.

FIGS. 8a–8d (SEQ ID NO: 7) depict the entire potential coding DNA nucleotide sequence of the heregulin-β1 and the deduced amino acid sequence of the cDNA contained in λher 11.1 dbl (SEQ ID NO: 9). The nucleotides are numbered at the top left of each line and the amino acids written in three letter code are numbered at the bottom left of each line. The probable transmembrane amino acid domain is amino acids 278–300. The six cysteines of the EGF motif are 212, 220, 226, 240, 242 and 251. The five potential three-amino acid N-linked glycosylation sites are 150–152, 156–158, 196–198, 428–430 and 600–612. The serine-threonine potential O-glycosylation sites are 195–207. Serine-glycine dipeptide potential glycosaminoglycan addition sites are amino acids 28–29, 50–51 and 137–138. The initiating methionine (MET) is at position #31. HRG-β1 is processed to the N-terminal residue S32.

Figure 9:
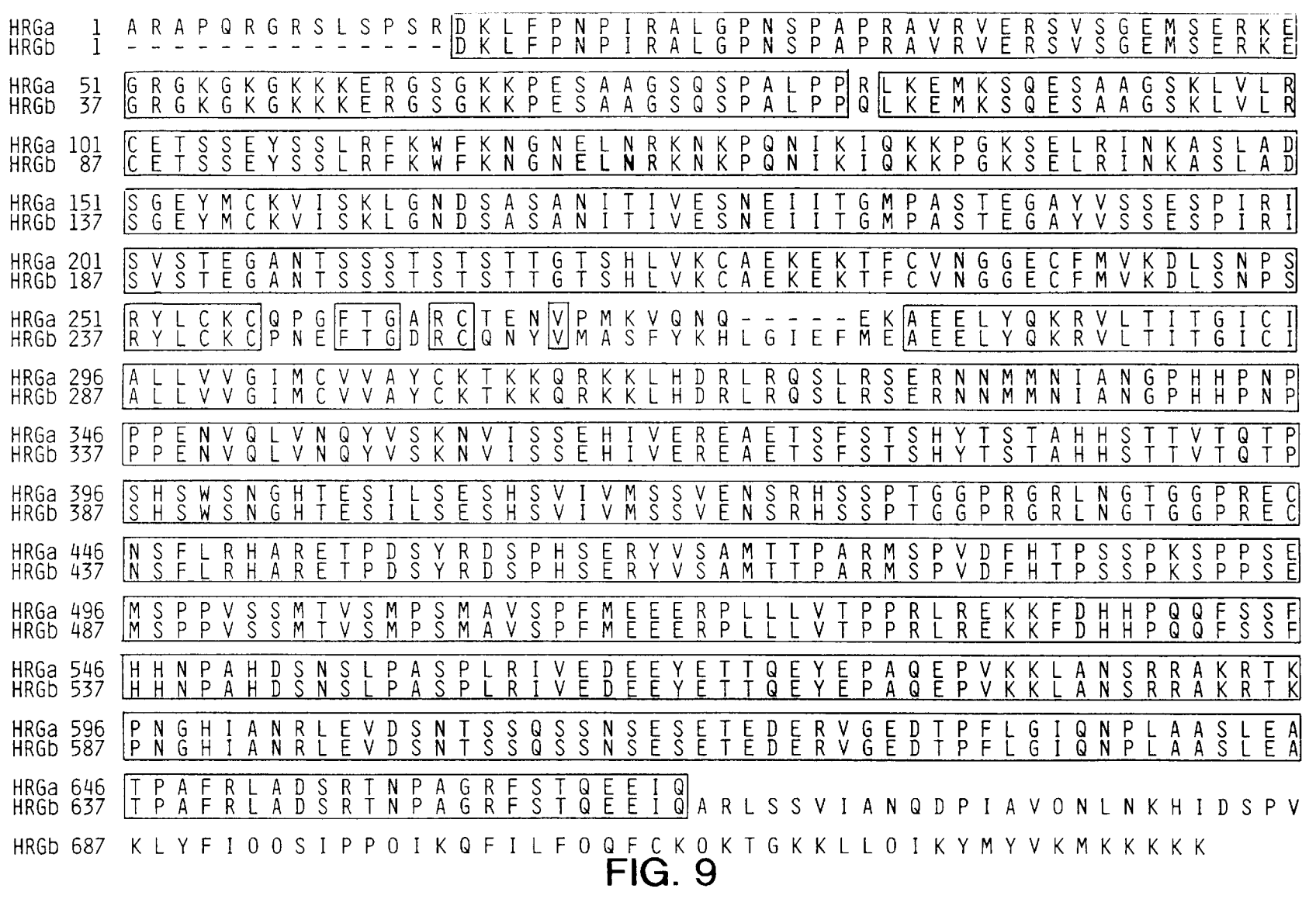

FIG. 9 depicts a comparison of the amino acid sequences of heregulin-α and -β1. A dash (-) indicates no amino acid at that position. (SEQ ID NO: 8 and SEQ ID NO: 9). This FIG. uses the numbering convention of FIGS. 4 and 6.

Figure 10:
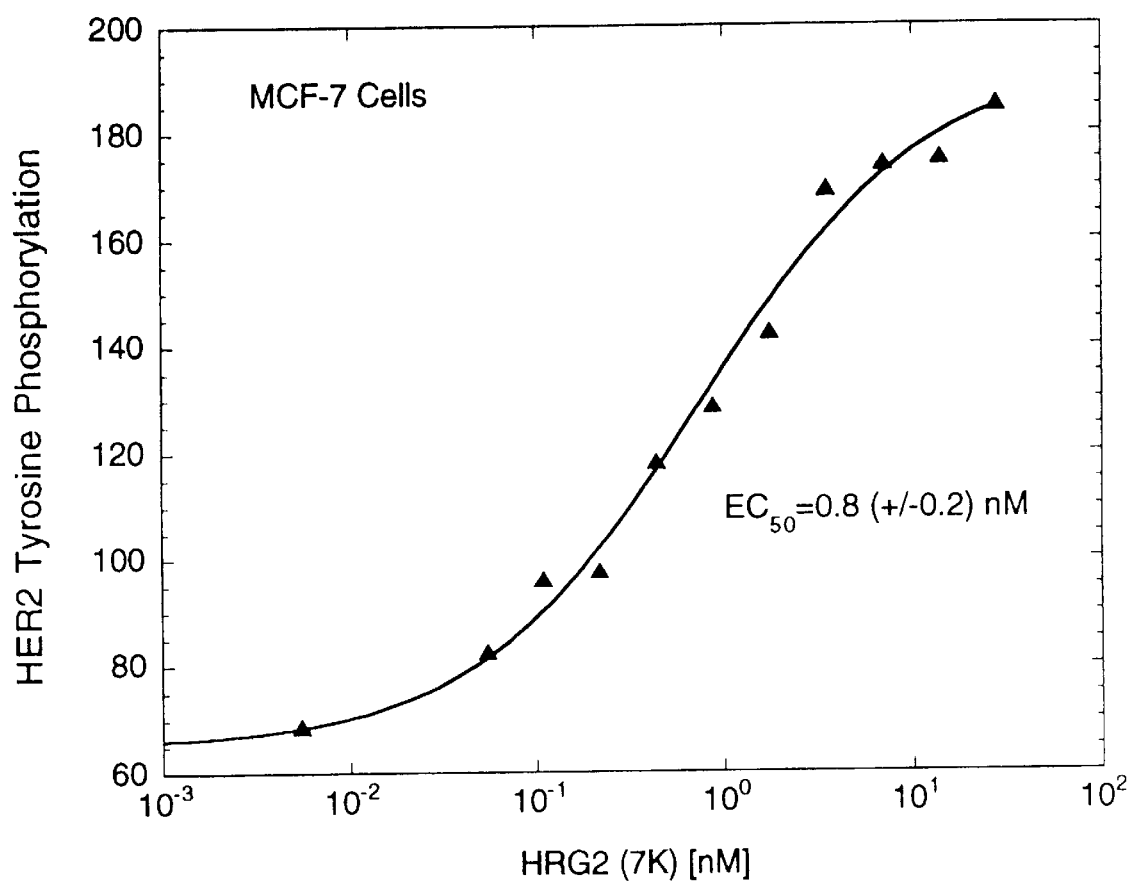

FIG. 10 shows the stimulation of HER2 autophosphorylation using recombinant HRG-α as measured by HER2 tyrosine phosphorylation.

FIG. 11 depicts the nucleotide and inputed amino acid sequence of λ15'her13 (SEQ ID NO: 22); the amino acid residue numbering convention is unique to this figure.

FIGS. 12a–12e depict the nucleotide sequence of λher76, encoding heregulin-β2 (SEQ ID NO: 23). This figure commences amino acid residue numbering with the expressed N-terminal MET; the N-terminus is S2.

FIGS. 13a–13c depict the nucleotide sequence of λher78, encoding heregulin-β3 (SEQ ID NO: 24). This figure uses the amino acid numbering convention of FIG. 12; S2 is the processed N-terminus.

FIGS. 14a–14d depict the nucleotide sequence of λher84, encoding a heregulin-β2-like polypeptide (SEQ ID NO: 25). This figure uses the amino acid numbering convention of FIG. 12; S2 is the processed N-terminus.

FIGS. 15a–15c depict the amino acid homologies between the known heregulins (α, β1, β2, β2-like and β3 in descending order) and illustrates the amino acid insertions, deletions or substitutions that distinguish the different forms (SEQ ID NOS: 26–30). This figure uses the amino acid numbering convention of FIGS. 12–14.

DETAILED DESCRIPTION OF THE PREFERRED EMBODIMENTS

I. Definitions

In general, the following words or phrases have the indicated definition when used in the description, examples, and claims.

Heregulin ("HRG") is defined herein to be any isolated polypeptide sequence which possesses a biological activity of a polypeptide disclosed in FIGS. 4, 8, 12, 13, or 15, and fragments, alleles or animal analogues thereof or their animal analogues. HRG excludes any polypeptide heretofore identified, including any known polypeptide which is otherwise anticipatory under 35 U.S.C. 102, as well as polypeptides obvious over such known polypeptides under 35 U.S.C. 103, including in particular EFG, TFG-α, amphiregulin (Plowman et al. Mol. Cell. Biol. 10: 1969 (1990), HB-EGF (Higashimaya et al., Science 251: 936 [1991]), schwannoma factor or polypeptides obvious thereover.

Biological activity for the purposes herein means an in vivo effector or antigenic function that is directly or indirectly performed by an HRG polypeptide (whether in its native or denatured conformation), or by any subsequence thereof. Effector functions include receptor binding or activation, induction of differentiation, mitogenic or growth promoting activity, immune modulation, DNA regulatory functions and the like, whether presently known or inherent. Antigenic functions include possession of an epitope or antigenic site that is capable of cross-reacting with antibodies raised against a naturally occurring or denatured HRG polypeptide or fragment thereof.

Biologically active HRG includes polypeptides having both an effector and antigenic function, or only one of such functions. HRG includes antagonist polypeptides to HRG, provided that such antagonists include an epitope of a native HRG. A principal known effector function of HRG is its ability to bind to $p185^{HER2}$ and activate the receptor tyrosine kinase.

HRG includes the translated amino acid sequence of full length human HRGs (proHRG) set forth herein in the Figures; deglycosylated or unglycosylated derivatives; amino acid sequence variants; and covalent derivatives of HRG, provided that they possess biological actvity. While the native proform of HRG is probably a membrane-bound polypeptide, soluble forms, such as those forms lacking a functional transmembrane domain (proHRG or its fragments), are also included within this definition.

Fragments of intact HRG are included within the definition of HRG. Two principal domains are included within the fragments. These are the growth factor domain ("GFD"), homologous to the EGF family and located at about residues S216-A227 to N268-R286 (FIG. 9, HRG-α; the GFD domains for other HRGs (FIG. 15) are the homologous sequences.). Preferably, the GFDs for HRG-α, β1, β2, β2-like and β3 are, respectively, G175-K241, G175-K246, G175-K238, G175-K238 and G175-E241 (FIG. 15).

Another fragment of interest is the N-terminal domain ("NTD"). The NTD extends from the N-terminus of processed HRG (S2) to the residue adjacent to an N-terminal residue of the GFD, i.e., about T172-C182 (FIG. 15) and preferably T174. An additional group of fragments are NTD-GFD domains, equivalent to the extracellular domains of HRG-α and β1-β2. Another fragment is the C-terminal peptide ("CTP") located about 20 residues N-terminal to the first residue of the transmembrane domain, either alone or in combination with the C-terminal remainder of the HRG.

In preferred embodiments, antigenically active HRG is a polypeptide that binds with an affinity of at least about $10^7$ I/mole to an antibody raised against a naturally occurring HRG sequence. Ordinarily the polypeptide binds with an affinity of at least about $10^8$ I/mole. Most preferably, the antigenically active HRG is a polypeptide that binds to an antibody raised against one of HRGs in its native conformation. HRG in its native conformation generally is HRG as found in nature which has not been denatured by chaotropic agents, heat or other treatment that substantially modifies the three dimensional structure of HRG as determined, for example, by migration on nonreducing, nondenaturing sizing gels. Antibody used in this determination is rabbit polyclonal antibody raised by formulating native HRG from a non-rabbit species in Freund's complete adjuvant, subcutaneously injecting the formulation into rabbits, and boosting the immune response by intraperitoneal injection of the formulation until the titer of anti-HRG antibody plateaus.

Ordinarily, biologically active HRG will have an amino acid sequence having at least 75% amino acid sequence identity with an HRG sequence, more preferably at least 80%, even more preferably at least 90%, and most preferably at least 95%. Identity or homology with respect to an HRG sequence is defined herein as the percentage of amino acid residues in the candidate sequence that are identical with HRG residues in FIGS. 15, after aligning the sequences and introducing gaps, If necessary, to achieve the maximum percent homology, and not considering any conservative substitutions to be identical residues. None of N-terminal, C-terminal or internal extensions, deletions, or insertions Into HRG sequence shall be construed as affecting homology.

Thus, the biologically active HRG polypeptides that are the subject of this invention include each expressed or processed HRG sequence; fragments thereof having a consecutive sequence of at least 5, 10, 15, 20, 25, 30 or 40 amino acid residues; amino acid sequence variants of HRG wherein an amino acid residue has been inserted N- or C-terminal to, or within, HRG sequence or its fragment as defined above; amino acid sequence variants of HRG sequence or its fragment as defined above wherein a residue has been substituted by another residue. HRG polypeptides include those containing predetermined mutations by, e.g., site-directed or PCR mutagenesis. HRG includes HRG from such as species as rabbit, rat, porcine, non-human primate, equine, murine, and ovine HRG and alleles or other naturally occurring variants of the foregoing; derivatives of HRG or its fragments as defined above wherein HRG or its fragments have been covalently modified by substitution, chemical, enzymatic, or other appropriate means with a moiety other than a naturally occurring amino acid (for example a detectable moiety such as an enzyme or radioisotope); glycosylation variants of HRG (insertion of a glycosylation site or deletion of any glycosylation site by deletion, insertion or substitution of an appropriate residue); and soluble forms of HRG, such as HRG-GFD or those that lack a functional transmembrane domain.

Of particular interest are fusion proteins that contain HRG-NTD but are free of the GFD ordinarily associated with the HRG-NTD in question. The first 23 amino acids of the NTD are dominated by charged residues and contain a sequence (GKKKER; residues 13–18, FIG. 15) that closely resembles the consensus sequence motif for nuclear targeting (Roberts, Biochim. Biophys. Acta. 1008: 263 [1989]). Accordingly, the HRG includes fusions in which the NTD, or at least a polypeptide comprising its first about 23 residues, is fused at a terminus to a non-HRG polypeptide or to a GFD of another HRG family member. The non-HRG polypeptide in this embodiment is a regulatory protein, a growth factor such as EGF or TGF-α, or a polypeptide ligand that binds to a cell receptor, particularly a cell surface receptor found on the surface of a cell whose regulation is desired, e.g. a cancer cell.

In another embodiment, one or more of residues 13–18 independently are varied to produce a sequence incapable of nuclear targeting. For example G13 is mutated to any other naturally occurring residue including P, L, I, V, A, M, F, K, D or S; any one or more of K14–K16 are mutated to any other naturally occurring residue including R,H,D,E,N or Q; E17 to any other naturally occurring residue including D, R, K, H, N or Q; and R18 to any other naturally occurring residue including K, H, D, E, N or Q. All or any one of residues 13–18 are deleted as well, or extraneous residues are inserted adjacent to these residues; for example residues inserted adjacent to residue 13–18 which are the same as the above- suggested substitutions for the residues themselves.

In another embodiment, enzymes or a nuclear regulatory protein such as a transcriptional regulatory factor is fused to HRG-NTD, HRG-NTD-GFD, or HRG-GFD. The enzyme or factor is fused to the N- or C- terminus, or inserted between the NTD and GFD domains, or is substituted for the region of NTD between the first about 23 residues and the GFD.

"Isolated" HRG means HRG which has been identified and is free of components of its natural environment. Contaminant components of its natural environment include materials which would interfere with diagnostic or therapeutic uses for HRG, and may include proteins, hormones, and other substances. In preferred embodiments, HRG will be purified (1) to greater than 95% by weight of protein as determined by the Lowry method or other validated protein determination method, and most preferably more than 99% by weight, (2) to a degree sufficient to obtain at least 15 residues of N-terminal or internal amino acid sequence by use of the best commercially available amino acid sequenator marketed on the filing date hereof, or (3) to homogeneity by SDS-PAGE using Coomassie blue or, preferably, silver stain. Isolated HRG includes HRG in situ within heterologous recombinant cells since at least one component of HRG natural environment will not be present. Isolated HRG includes HRG from one species in a recombinant cell culture of another species since HRG in such circumstances will be devoid of source polypeptides. Ordinarily, however, isolated HRG will be prepared by at least one purification step.

In accordance with this invention, HRG nucleic acid is RNA or DNA containing greater than ten bases that encodes a biologically or antigenically active HRG, is complementary to nucleic acid sequence encoding such HRG, or hybridizes to nucleic acid sequence encoding such HRG and remains stably bound to it under stringent conditions.

Preferably, HRG nucleic acid encodes a polypeptide sharing at least 75% sequence identity, more preferably at least 80%, still more preferably at least 85%, even more preferably at 90%, and most preferably 95%, with an HRG sequence. Preferably, the HRG nucleic acid that hybridizes contains at least 20, more preferably at least about 40, and most preferably at least about 90 bases. Such hybridizing or complementary nucleic acid, however, is further defined as being novel under 35 U.S.C. 102 and unobvious under 35 U.S.C. 103 over any prior art nucleic acid and excludes nucleic acid encoding EGF, TGF-α, amphiregulin, HB-EGF, schwannoma factor or fragments or variants thereof which would have been obvious as of the filing date hereof.

Isolated HRG nucleic acid includes a nucleic acid that is free from at least one contaminant nucleic acid with which it is ordinarily associated in the natural source of HRG nucleic acid. Isolated HRG nucleic acid thus is present in other than in the form or setting in which it is found in nature. However, isolated HRG encoding nucleic acid includes HRG nucleic acid in ordinarily HRG-expressing cells where the nucleic acid is in a chromosomal location different from that of natural cells or is otherwise flanked by a different DNA sequence than that found in nature. Nucleic acid encoding HRG may be used in specific hybridization assays, particularly those portions of HRG encoding sequence that do not hybridize with other known DNA sequences, for example those encoding the EGF-like molecules of FIG. 6.

"Stringent conditions" are those that (1) employ low ionic strength and high temperature for washing, for example, 0.015M NACl/0.0015M sodium citrate/O/1% NaDodSO$_4$ at 50° C.; (2) employ during hybridization a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS.

Particular HRG-α nucleic acids are nucleic acids or oligonucleotides consisting of or comprising a nucleotide sequence selected from FIGS. 4a–4d and containing greater than 17 bases (when excluding nucleic acid sequences of human small polydisperse circular DNA (HUMPC125), chicken c-mos proto-oncogene homolog (CHKMOS), basement membrane heparin sulfate proteoglycan (HUMBMHSP) and human lipocortin 2 pseudogene (complete cds-like region, HUMLIP2B), ordinarily greater than 20 bases, preferably greater than 25 bases, together with the complementary sequences thereof.

Particular HRG-$\beta_1$, -$\beta_2$ or -$\beta_3$ nucleic acids are nucleic acids or oligonucleotides consisting of or comprising a nucleotide sequence selected from FIGS. 8a–8d, 12a–12e or 13a–13c and containing greater than 20 bases, but does not include the polyA sequence found at the 3' end of each gene as noted in the Figures, together with the complements to such sequences. Preferably the sequence contains contains greater than 25 bases. HRG-$\beta$ sequences also may exclude the human small polydisperse circular DNA sequence (HUMP-C125).

In other embodiments, the HRG nucleotide sequence contains a 15 or more base HRG sequence and is selected from within the sequence encoding the HRG domain extending from the N-terminus of the GFD to the N-terminus of the transmembrane sequence (or the complement of that nucleic acid sequence). For example, with respect to HRG-α, the nucleotide sequence is selected from within the sequence 678–869 (FIG. 4b) and contains a sequence of 15 or more bases from this section of the HRG nucleic acid.

In other embodiments, the HRG nucleic acid sequence is greater than 14 bases and is selected from a nucleotide sequence unique to each subtype, for instance a nucleic acid sequence encoding an amino acid sequence that is unique to each of the HRG subtypes (or the complement of that nucleic acid sequence). These sequences are useful in diagnostic assays for expression of the various subtypes, as well as specific amplification of the subtype DNA. For example, the HRG-α sequence of interest would be selected from the sequence encoding the unique N-terminus or GFD-transmembrane joining sequence, e.g. about bp771–860. Similarly, a unique HRG-$\beta$1 sequence is that which encodes the last 15 C-terminal amino acid residues; this sequence is not found in HRG-α.

In general, the length of the HRG-α or $\beta$ sequence beyond greater than the above-indicated number of bases is immaterial since all of such nucleic acids are useful as probes or amplification primers. The selected HRG sequence may contain additional HRG sequence, either the normal flanking sequence or other regions of the HRG nucleic acid, as well as other nucleic acid sequences. For purposes of hybridization, only the HRG sequence is material.

The term "control sequences" refers to DNA sequences necessary for the expression of an operably linked coding sequence In a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when It is placed into a functional relationship with another nucleic acid sequence. For example, DNA for a presequence or secretory leader is operably linked to DNA for a polypeptide If it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However enhancers do not have to be contiguous. Linking is accomplished by ligation at convenient restriction sites. If such sites do not exist, then synthetic oligonucleotide adaptors or linkers are used in accord with conventional practice.

An "exogenous" element is defined herein to mean nucleic acid sequence that is foreign to the cell, or homologous to the cell but in a position within the host cell nucleic acid in which the element is ordinarily not found.

As used herein, the expressions "cell", "cell line", and "cell culture" are used interchangeably, and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. It will be clear from the context where distinct designations are intended.

"Plasmids" are designated by a lower case "p" preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Restriction Enzyme Digestion" of DNA refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained, and then a number designating the particular enzyme. In general, about 1 pg of plasmid or DNA fragment is used with about 1–2 units of enzyme in about 20 $\mu$l of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in sections 1.56–1.61 of Sambrook et al., (*Molecular Cloning: A Laboratory Manual* New York: Cold Spring Harbor Laboratory Press, 1989).

"Ligation" refers to the process of forming phosphodiester bonds between two nucleic acid fragments. To ligate the DNA fragments together, the ends of the DNA fragments must be compatible with each other. In some cases, the ends will be directly compatible after endonuclease digestion. However, It may be necessary to first convert the staggered ends commonly produced after endonuclease digestion to blunt ends to make them compatible for ligation. To blunt the ends, the DNA is treated in a suitable buffer for at least 15 minutes at 15° C. with about 10 units of the Kienow fragment of DNA polymerase I or T4 DNA polymerase in the presence of the four deoxyribonucleotide triphosphates. The DNA is then purified by phenol-chloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 $\mu$g of DNA. If the DNA is to be ligated into a vector, the vector Is first linearized by digestion with the appropriate restriction endonuclease(s). The linearized fragment is then treated with bacterial alkaline phosphatase, or calf intestinal phosphatase to prevent self-ligation during the ligation step.

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195, issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.* 51: 263 (1987); Erlich, ed., *PCR Technology*, (Stockton Press, NY, 1989). As used herein, PCR is considered to be one, but not the only, example of a nucleic acid polymerase reaction method for amplifying a nucleic acid test sample, comprising the use of a known nucleic acid (DNA or RNA) as a primer, and utilizes a nucleic acid polymerase to amplify or generate a specific piece of nucleic acid or to amplify or generate a specific piece of nucleic acid which is complementary to a particular nucleic acid.

The "HRG tyrosine autophosphorylation assay" to detect the presence of HRG ligands was used to monitor the purification of a ligand for the p185$^{HER2}$ receptor. This assay is based on the assumption that a specific ligand for the p185$^{HER2}$ receptor will stimulate autophosphorylation of the receptor, in analogy with EGF and its stimulation of EGF receptor autophosphorylation. MDA-MB-453 cells or MCF7 cells which contain high levels of p185$^{HER2}$ receptors but negligible levels of human EGF receptors, were obtained from the American Type Culture Collection, Rockville, Md. (ATCC No HTB-131) and maintained in tissue culture with 10% fetal calf serum in DMEM/Hams F12 (1:1) media. For assay, the cells were trypsinized and plated at about 150,000 cells/well in 24 well dishes (Costar). After incubation with serum containing media overnight, the cells were placed in serum free media for 2–18 hours before assay. Test samples of 100 uL aliquots were added to each well. The cells were incubated for 5–30 minutes (typically 30 min) at 37° C. and the media removed. The cells in each well were treated with 100 uL SDS gel denaturing buffer (Seprosol, Enpotech, Inc.) and the plates heated at 100° C. for 5 minutes to dissolve the cells and denature the proteins. Aliquots from each well were electrophoresed on 5–20% gradient SDS gels (Novex, Encinitas, Calif.) according to the manufacturer's directions. After the dye front reached the bottom of the gel, the electrophoresis was terminated and a sheet of PVDF membrane (ProBlott, ABI) was placed on the gel and the proteins transferred from the gel to the membrane in a blotting chamber (BioRad) at 200 mAmps for 30–60 min. After blotting, the membranes were incubated with Tris buffered saline containing 0.1% Tween 20 detergent buffer with 5% BSA for 2–18 hrs to block nonspecific binding, and then treated with a mouse anti-phosphotyrosine antibody (Upstate Biological Inc., N.Y.). Subsequently, the membrane blots were treated with goat anti-mouse antibody conjugated to alkaline phosphatase. The gels were developed using the ProtoBlot System from Promega. After drying the membranes, the density of the bands corresponding to p185$^{HER2}$ in each sample lane was quantitated with a Hewlett Packard ScanJet Plus Scanner attached to a Macintosh computer. The number of receptors per cell in the MDA-MB-453 or MCF-7cells is such that under these experimental conditions the p185$^{HER2}$ receptor protein is the major protein which is labeled.

"Protein microsequencing" was accomplished based upon the following procedures. Proteins from the final HPLC step were either sequenced directly by automated Edman degradation with a model 470A Applied Biosystems gas phase sequencer equipped with a 120A PTH amino acid analyzer or sequenced after digestion with various chemicals or enzymes. PTH amino acids were integrated using the ChromPerfect data system (Justice Innovations, Palo Alto, Calif.). Sequence interpretation was performed on a VAX 11/785 Digital Equipment Corporation computer as described (Henzel et al., *J. Chromatography* 404: 41–52 (1987)). In some cases, aliquots of the HPLC fractions were electrophoresed on 5–20% SDS polyacrylamide gels, electrotransferred to a PVDF membrane (ProBlott, ABI, Foster City, Calif.) and stained with Coomassie Brilliant Blue (Matsudaira, P., *J. Biol. Chem.* 262: 10035–10038, 1987). The specific protein was excised from the blot for N terminal sequencing. To determine internal protein sequences, HPLC fractions were dried under vacuum (SpeedVac), resuspended in appropriate buffers, and digested with cyanogen bromide, the lysine-specific enzyme Lys-C (Wako Chemicals, Richmond, Va.) or Asp-N (Boehringer Mannheim, Indianapolis, Ind.). After digestion, the resultant peptides were sequenced as a mixture or were resolved by HPLC on a C4 column developed with a propanol gradient in 0.1% TFA before sequencing as described above.

II. USE AND PREPARATION OF HRG POLYPEPTIDES

1. PREPARATION OF HRG POLYPEPTIDES INCLUDING VARIANTS

The system to be employed in preparing HRG polypeptides will depend upon the particular HRG sequence selected. If the sequence is sufficiently small HRG is prepared by in vitro polypeptide synthetic methods. Most commonly, however, HRG is prepared in recombinant cell culture using the host-vector systems described below.

In general, mammalian host cells will be employed, and such hosts may or may not contain post-translational systems for processing HRG prosequences in the normal fashion. If the host cells contain such systems then it will be possible to recover natural subdomain fragments such as HRG-GFD OR HRG-NTD-GFD from the cultures. If not, then the proper processing can be accomplished by transforming the hosts with the required enzyme(s) or by cleaving the precursor in vitro. However, it is not necessary to transform cells with DNA encoding the complete prosequence for a selected HRG when it is desired to only produce fragments of HRG sequences such as an HRG-GFD. For example, to prepare HRG-GFD a start codon is ligated to the 5' end of DNA encoding an HRG-GFD, this DNA is used to transform host cells and the product expressed directly as the Met N-terminal form (if desired, the extraneous Met may be removed in vitro or by endogenous N-terminal demethionylases). Alternatively, HRG-GFD is expressed as a fusion with a signal sequence recognized by the host cell, which will process and secrete the mature HRG-GFD as is further described below. Amino acid sequence variants of native HRG-GFD sequences are produced in the same way.

HRG-NTD is produced in the same fashion as the full length molecule but from expression of DNA encoding only HRG-NTD, with the stop codon after one of S172-C182 (FIG. 15).

In addition, HRG variants are expressed from DNA encoding protein in which both the GFD and NTD domains are in their proper orientation but which contain an amino acid insertion, deletion or substitution at the NTD-GFD joining site (for example located within the sequence S172-C182. In another embodiment a stop codon is positioned at the 3' end of the NTD-GFD-encoding sequence (after any residue T/Q222-T245 of FIG. 15). The result is a soluble form of HRG-α or -β1 or -β2 which lacks its transmembrane sequence (this sequence also may be an internal signal sequence but will be referred to as a transmembrane sequence). In further variations of this embodiment, an internal 15 signal sequence of another polypeptide is substituted in place of the native HRG transmembrane domain, or a cytoplasmic domain of another cell membrane polypeptide, e.g. receptor kinase, is substituted for the HRG-α or HRG $\beta_1$-$\beta_2$ cytoplasmic peptide.

In a still further embodiment, the NTD, GFD and transmembrane domains of HRG and other EGF family members are substituted for one another, e.g. the NTD equivalent region of EGF is substituted for the NTD of HRG, or the GFD of HRG is substituted for EGF in the processed, soluble proform of EGF. Alternatively, an HRG or EGF family member transmembrane domain is fused onto the C-terminal E236 of HRG-$\beta_3$.

In a further variant, the HRG sequence spanning K241 to the C-terminus is fused at its N-terminus to the C-terminus of a non-HRG polypeptide.

Another embodiment comprises the functional or structural deletion of the proteolytic processing site in CTP, the GFD-transmembrane spanning domain. For example, the putative C-terminal lysine (K241) of processed HRG-α or $\beta_1$-$\beta_2$ is deleted, substituted with another residue, a residue other than K or R inserted between K241 and R242, or other disabling mutation is made in the prosequence.

In another embodiment, the domain of any EGF family member extending from (a) its cysteine corresponding to (b) C221 to the C-terminal residue of the family member is substituted for the analogous domain of HRG-α or -$\beta_1$ or -$\beta_2$ (or fused to the C-terminus of HRG-$\beta_3$). Such variants will be processed free of host cells in the same fashion as the family member rather than as the parental HRG. In more refined embodiments other specific cleavage sites (e.g. protease sites) are substituted into the CTP or GFD-transmembrane spanning domain (about residues T/Q222-T245, FIG. 15). For example, amphiregulin sequence E84-K99 or TGFA sequence E44-K58 is substituted for HRG-A residues E223-K241.

In a further embodiment, a variant (termed HRG-NTDxGFD) is prepared wherein (1) the lysine residue found in the NTD-GFD joining sequence VKC (residues 180–182, FIG. 15) is deleted or (preferably) substituted by another residue other than R such as H, A, T or S and (2) a stop codon Is Introduced in the sequence RCT or RCQ (residues 220–222, FIG. 15) in place of C, or T (for HRG-α) or O (for HRG-beta).

A preferred HRG-α ligand with binding affinity to p185$^{HER2}$ comprises amino acids 226–265 of FIG. 4. This HRG-A ligand further may comprise up to an additional 1–20 amino acids preceding amino acid 226 from FIG. 4 and 1–20 amino acids following amino acid 265 from FIG. 4. A preferred HRG-β ligand with binding affinity to p185$^{HER2}$ comprises amino acids 226–265 of FIG. 8. This HRG-β ligand may comprise up to an additional 1–20 amino acids preceding amino acid 226 from FIG. 8 and 1–20 amino acids following amino acid 265 from FIG. 8.

GFD sequences include those in which one or more residues corresponding to another member of the EGF family are deleted or substituted or have a residue inserted adjacent thereto. For example, F216 of HRG is substituted by Y, L202 with E, F189 with Y. or S203-P205 is deleted.

HRG also includes NTD-GFD having its C-terminus at one of the first about 1 to 3 extracellular domain residues (QKR, residues 240–243, HRE-α, FIG. 15) or first about 1–2 transmembrane region residues. In addition, in some HRG-GFD variants the codons are modified at the GFD-transmember proproteolysis site by substitution, insertion or deletion. The GFD proteolysis site is the domain that contains the GFD C-terminal residue and about 5 residues N- and 5 residues C-terminal from this residue. At this time neither the natural C-terminal residue for HRG-α or HRG-β has been identified, although it is known that Met-227 terminal and Val-229 terminal HRG-α-GFD are biologically active. The native C-terminus for HRG-α-GFD is probably Met-227, Lys-228, Val-229, Gln-230, Asn-231 or Gln-232, and for HRG $\beta_1$-$\beta_2$-GFD is probably Met-226, Ala-227, Ser-228, Phe-229, Trp-230, Lys 231 or (for HRG-$\beta_1$) K240 or (for HRG-$\beta_2$) K246. The native C-terminus Is determined readily by C-terminal sequencing, although it is not critical that HRG-GFD have the native terminus so long as the GFD sequence possesses the desired activity. In some embodiments of HRG-GFD variants, the amino acid change(s) in the CTP are screened for their ability to resist proteolysis in vitro and inhibit the protease responsible for generation of HRG-GFD.

If it is desired to prepare the full length HRG polypeptides and the 5' or 3' ends of the given HRG are not described herein, it may be necessary to prepare nucleic acids in which the missing domains are supplied by homologous regions from more complete HRG nucleic acids. Alternatively, the missing domains can be obtained by probing libraries using the DNAs disclosed in the Figures or fragments thereof.

A. Isolation of DNA Encoding Heregulin

The DNA encoding HRG may be obtained from any cDNA library prepared from tissue believed to possess HRG mRNA and to express it at a detectable level. HRG DNA also is obtained from a genomic library.

Libraries are screened with probes or analytical tools designed to identify the gene of interest or the protein encoded by it. For cDNA expression libraries, suitable probes include monoclonal or polyclonal antibodies that recognize and specifically bind to HRG; oligonucleotides of about 20–80 bases in length that encode known or suspected portions of HRG cDNA from the same or different species; and/or complementary or homologous cDNAs or fragments thereof that encode the same or a hydridizing gene. Appropriate probes for screening genomic DNA libraries include, but are not limited to, oligonucleotides; cDNAs or fragments thereof that encode the same or hybridizing DNA; and/or homologous genomic DNAs or fragments thereof. Screening the cDNA or genomic library with the selected probe may be conducted using standard procedures as described in chapters 10–12 of Sambrook et al., supra.

An alternative means to isolate the gene encoding HRG is to use polymerase chain reaction (PCR) methodology as described in section 14 of Sambrook et al., supra. This method requires the use of oligonucleotide probes that will hybridize to HRG. Strategies for selection of oligonucleotides are described below.

Another alternative method for obtaining the gene of interest is to chemically synthesize it using one of the methods described in Engels et al. (Agnew. *Chem. Int. Ed. Engl.*, 28: 716–734,1989), specifically incorporated by reference. These methods include triester, phosphite, phosphoramidite and H-Phosphonate methods, PCR and other autoprimer methods, and oligonucleotide syntheses on solid supports. These methods may be used if the entire nucleic acid sequence of the gene is known, or the sequence of the nucleic acid complementary to the coding strand is available, or alternatively, If the target amino acid sequence is known, one may Infer potential nucleic acid sequences using known and preferred coding residues for each amino acid residue.

A preferred method of practicing this Invention is to use carefully selected oligonucleotide sequences to screen cDNA libraries from various tissues, preferably human breast, colon, salivary gland, placental, fetal, brain, and carcinoma cell lines. Other biological sources of DNA encoding an heregulin-like ligand include other mammals and birds. Among the preferred mammals are members of the following orders: bovine, ovine, equine, murine, and rodentia.

The oligonucleotide sequences selected as probes should be of sufficient length and sufficiently unambiguous that false positives are minimized. The actual nucleotide sequence(s) is usually based on conserved or highly homologous nucleotide sequences or regions of HRG-α. The oligonucleotides may be degenerate at one or more positions. The use of degenerate oligonucleotides may be of particular importance where a library is screened from a species in which preferential codon usage in that species is not known. The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

Of particular interest is HRG nucleic acid that encodes the full-length propolypeptide. In some preferred embodiments, the nucleic acid sequence includes the native HRG signal transmembrane sequence. Nucleic acid having all the protein coding sequence is obtained by screening selected cDNA or genomic libraries, and, if necessary, using conventional primer extension procedures as described in section 7.79 of Sambrook et al., supra, to detect precursors and processing intermediates of mRNA that may not have been reverse-transcribed into cDNA.

HRG encoding DNA is used to isolate DNA encoding the analogous ligand from other animal species via hybridization employing the methods discussed above. The preferred animals are mammals, particularly bovine, ovine, equine, feline, canine and rodentia, and more specifically rats, mice and rabbits.

B. Amino Acid Sequence Variants of Heregulin

Amino acid sequence variants of HRG are prepared by introducing appropriate nucleotide changes into HRG DNA, or by in vitro synthesis of the desired HRG polypeptide. Such variants include, for example, deletions from, or insertions or substitutions of, residues within the amino acid sequence shown for human HRG sequences. Any combination of deletion, insertion, and substitution can be made to arrive at the final construct, provided that the final construct possesses the desired characteristics. The amino acid changes also may alter post-translational processes of HRG-α, such as changing the number or position of glycosylation sites, altering the membrane anchoring characteristics, altering the intra-cellular location of HRG by inserting, deleting, or otherwise affecting the transmembrane sequence of native HRG, or modifying its susceptibility to proteolytic cleavage.

In designing amino acid sequence variants of HRG, the location of the mutation site and the nature of the mutation will depend on HRG characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of other ligands adjacent to the located site.

A useful method for identification of HRG residues or regions for mutagenesis is called "alanine scanning mutagenesis" as described by Cunningham and Wells (*Science*, 244: 1081–1085, 1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, ala scanning or random mutagenesis may be conducted at the target codon or region and the expressed HRG variants are screened for the optimal combination of desired activity.

There are two principal variables in the construction of amino acid sequence variants: the location of the mutation site and the nature of the mutation. These are variants from HRG sequence, and may represent naturally occurring alleles (which will not require manipulation of HRG DNA) or predetermined mutant forms made by mutating the DNA, either to arrive at an allele or a variant not found in nature. In general, the location and nature of the mutation chosen will depend upon HRG characteristic to be modified. Obviously, such variations that, for example, convert HRG into a known receptor ligand, are not included within the scope of this invention, nor are any other HRG variants or polypeptide sequences that are not novel and unobvious over the prior art.

Amino acid sequence deletions generally range from about 1 to 30 residues, more preferably about 1 to 10 residues, and typically about 1 to 5 contiguous residues. Deletions may be introduced into regions of low homology with other EGF family precursors to modify the activity of HRG. Deletions from HRG in areas of substantial homology with other EGF family sequences will be more likely to modify the biological activity of HRG more significantly. The number of consecutive deletions will be selected so as to preserve the tertiary structure of HRG in the affected domain, e.g., cysteine crosslinking, beta-pleated sheet or alpha helix.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within HRG sequence) may range generally from about 1 to 10 residues, more preferably 1 to 5, and most preferably 1 to 3. Examples of terminal insertions include HRG with an N-terminal methionyl residue (an artifact of the direct expression of HRG in bacterial recombinant cell culture), and fusion of a heterologous N-terminal signal sequence to the N-terminus of HRG to facilitate the secretion of mature HRG from recombinant host cells. Such signal sequences generally will be obtained from, and thus be homologous to, the intended host cell species. Suitable sequences include STII or Ipp for *E. coli,* alpha factor for yeast, and viral signals such as herpes gD for mammalian cells.

Other insertional variants of HRG include the fusion to the N- or C-terminus of HRG to an immunogenic polypeptide, e.g., bacterial polypeptides such as beta-lactamase or an enzyme encoded by the *E. coli trp* locus, or yeast protein, bovine serum albumin, and chemotactic polypeptides. C-terminal fusions of HRG-NTD-GFD with proteins having a long half-life such as immunoglobulin constant regions (or other immunoglobulin regions), albumin, or ferritin, as described in WO 89/02922, published 6 Apr. 1989 are included.

Another group of variants are amino acid substitution variants. These variants have at least one amino acid residue in the HRG molecule removed and a different residue inserted in its place. The sites of greatest interest for substitutional mutagenesis include sites identified as the active site(s) of HRG, and sites where the amino acids found in HRG ligands from various species are substantially different in terms of side-chain bulk, charge, and/or hydrophobicity.

The amino terminus of the cytoplasmic region of HRG may be fused to the carboxy terminus of heterologous transmembrane domains and receptors, to form a fusion polypeptide useful for intracellular signaling of a ligand binding to the heterologous receptor.

Other sites of interest are those in which particular residues of HRG-like ligands obtained from various species are identical. These positions may be important for the biological activity of HRG. These sites, especially those falling within a sequence of at least three other identically conserved sites, are substituted in a relatively conservative manner. Such conservative substitutions are shown in Table 1 under the heading of "preferred substitutions". If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Substantial modifications in function or immunological identity of HRG are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.
Naturally occurring residues are divided into groups based on common side chain properties:

1) hydrophobic: norleucine, met, ala, val, leu, ile;
2) neutral hydrophilic: cys, ser, thr;
3) acidic: asp, glu;
4) basic: asn, gln, his, lys, arg;
5) residues that influence chain orientation: gly, pro; and
6) aromatic: trp, tyr, phe.

Non-conservative substitutions will entail exchanging a member of one of these classes for another. Such substituted residues may be Introduced into regions of HRG that are homologous with other receptor ligands, or, more preferably, into the non-homologous regions of the molecule.

In one embodiment of the invention, it is desirable to inactivate one or more protease cleavage sites that are present in the molecule. These sites are identified by inspection of the encoded amino acid sequence. Where potential protease cleavage sites are identified, e.g. at K241 R242, they are rendered inactive to proteolytic cleavage by substituting the targeted residue with another residue, preferably a basic residue such as glutamine or a hydrophylic residue such as serine; by deleting the residue; or by inserting a prolyl residue immediately after the residue.

In another embodiment, any methionyl residue other than the starting methionyl residue, or any residue located within about three residues N- or C-terminal to each such methionyl residue, is substituted by another residue (preferably in accord with Table 1) or deleted. We have found that oxidation of the 2 GFD M residues in the courses of *E. coli* expression appears to severely reduce GFD activity. Thus, these M residues are mutated in accord with Table 1. Alternatively, about 1–3 residues are inserted adjacent to such sites.

Any cysteine residues not involved in maintaining the proper conformation of HRG also may be substituted, generally with serine, to improve the oxidative stability of the molecule and prevent aberrant crosslinking.

Sites particularly suited for substitutions, deletions or insertions, or use as fragments, include, numbered from the N-terminus of HRG-A of FIG. 4:

1) potential glycosaminoglycan addition sites at the serine-glycine dipeptides at 42–43, 64–65, 151–152;
2) potential asparagine-linked glycosylation at positions 164, 170, 208 and 437, sites (NDS) 164–166, (NIT) 170–172, (NTS) 208–210, and NTS (609–611);
3) potential O-glycosylation in a cluster of serine and threonine at 209–218;
4) cysteines at 226, 234, 240, 254, 256 and 265;
5) transmembrane domain at 287–309;
6) loop 1 delineated by cysteines 226 and 240;
7) loop 2 delineated by cysteines 234 and 254;
8) loop 3 delineated by cysteines 256 and 265; and
9) potential protease processing sites at 2–3, 8–9, 23–24, 33–34, 36–37, 45–46, 48–49, 62–63, 66–67, 86–87, 110–111, 123–124, 134–135, 142–143, 272–273, 278–279 and 285–286;

Analogous regions in HRG-β1 may be determined by reference to FIG. 9 which aligns analogous amino acids in HRG-α and HRG-β1. The analogous HRG-β1 amino acids may be mutated or modified as discussed above for HRG-α. Analogous regions in HRG-β2 may be determined by reference to FIG. 15 which aligns analogous amino acids in HRG-α, HRG-β1 and HRG-β2. The analogous HRG-β2 amino acids may be mutated or modified as discussed above for HRG-α or HRG-β1. Analogous regions in HRG-β3 may be determined by reference to FIG. 15 which aligns analogous amino acids in HRG-α, HRG-β1 and HRG-β2. The analogous HRG-β3 amino acids may be mutated or modified as discussed above for HRG-α, HRG-β1, or HRG-β2.

DNA encoding amino acid sequence variants of HRG is prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of HRG. These techniques may utilize HRG nucleic acid (DNA or RNA), or nucleic acid complementary to HRG nucleic acid.

Oligonucleotide-mediated mutagenesis is a preferred method for preparing substitution, deletion, and insertion variants of HRG DNA. This technique is well known in the art as described by Adelman et al., *DNA,* 2: 183 (1983).

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA,* 75: 5765, 1978).

Single-stranded DNA template may also be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Kienow fragment of DNA polymerase I, is then added to synthesize the complementary strand of the template using the oligonucleotide as a primer for synthesis. A heteroduplex molecule is thus formed such that one strand of DNA encodes the mutated form of HRG, and the other strand (the original template) encodes the native, unaltered sequence of HRG. This heteroduplex molecule is then transformed into a suitable host cell, usually a prokaryote such as *E. coli* JM101. After the cells are grown, they are plated onto agarose plates and screened using the oligonucleotide primer radiolabeled with $^{32}$P-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: the single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase In the presence of all four deoxyribonucleotide triphosphates, ATP, and DNA ligase. This homoduplex molecule can then be transformed into a suitable host cell such as *E. coli* JM101, as described above.

Explanary substitutions common to any HRG include S2T or D; E3D or K; R4 K or E; K5R or E; E6D or K; G7P or Y; R8K or D; G9P or Y; K10R or E; G11P or Y; K12R or E; G19P or Y; S20T or F; G21P or Y; K22 or E; K23R or E; Q38D; S107N; G108P; N120K; D121K; S122 T; N126S; I126L; T127S; A163V; N164K; T165–T174; any residue to I, L, V, M, F, D, E, R or K; G175V or P; T176S or V; S177K or T; H178K or S; L179F or I; V180L or S; K181R or E; A 183N or V; E184K or D; K185R or E; E186D or Y; K187R or D; T188S or Q; F189Y or S; V191L or D; N192O or H; G193P or A; G194P or A; E195D or K; F197Y or I; M198V or Y; V199L or T; K200V or R; D201E or K; L202E or K; S203A or T; N204Δ; N204Q; P205Δ; P205G; S206T or R; R207K or A; Y208P or F; L209I or D; K211I or D; F216Y or I; T217 H or S; G218A or P; A/D219K or R; R220K or A; A235/240/232V or F; E236/241/233D or K; E237/242/234D or K; L238/243/235I or T; Y239/244/236F or T; Q240/245/237N or K; K241/246/238H or R; R242/247/238H or K; V243/248/239L or T; L244/249/240I or S; T245/250/241 S or I; 1246/251/242V or T and T247/252/243S or I. Specifically with respect to HRG-α, T222S, K or V; E223D, R or Q; N224Q, K or F; V225A, R or D; P226G, I K or F; M227V, T, R or Y; K228R, H or D; V229L, K or D; Q230N, R or Y; N231Q, K or Y; Q232N, R or Y; E233D, K or T and K 234R, H or D (adjacent K/R mutations are paired in alternative embodiments to create new proteolysis sites). Specifically with respect to HRG-β (any member), Q222N, R or Y; N223Q, K or Y; Y224F, T or R; V225A, K or D; M226V, T or R; A227V, K, Y or D; S228T, Y or R; F229Y, I or K and Y230F, T or R are suitable variants. Specifically with respect to HRG-β1, K231R or D, H232R or D; L233I, K, F or Y; G234P, R, A or S; I235I, K, F or Y; E236D, R or A; F237I, Y, K or A; M238V, T, R or A and E239D, R or A are suitable variants. Specifically with respect to HRG-$β_1$ and HRG-$β_2$, K231 R or D are suitable variants. Alternatively, each of these residues may be deleted or the indicated substituents inserted adjacent thereto. In addition, about from 1–10 variants are combined to produce combinations. These changes are made in the proHRG, NTD, GFD, NTD-GFD or other fragments or fusions. Q213-G215, A219 and the about 11–21 residues C-terminal to C221 differ among the various HRG classes. Residues at these are interchanged among HRG classes or EGF family members, are deleted, or a residue inserted adjacent thereto.

DNA encoding HRG-α mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

PCR mutagenesis is also suitable for making amino acid variants of HRG-α. While the following discussion refers to DNA, it is understood that the technique also finds application with RNA. The PCR technique generally refers to the following procedure (see Erlich, supra, the chapter by R. Higuchi, p. 61–70). When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation Into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

Another method for preparing variants, cassette mutagenesis, is based on the technique described by Wells et al. (*Gene,* 34: 315,1985). The starting material is the plasmid (or other vector) comprising HRG DNA to be mutated. The codon(s) in HRG DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in HRG DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated HRG DNA sequence.

C. Insertion of DNA Into a Cloning or Expression Vehicle

The cDNA or genomic DNA encoding native or variant HRG is inserted into a replicable vector for further cloning (amplification of the DNA) or for expression. Many vectors are available, and selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

(I) Signal Sequence Component

In general, the signal sequence may be a component of the vector, or It may be a part of HRG DNA that is Inserted into the vector. The native HRG DNA is believed to encode a signal sequence at the amino terminus (5' end of the DNA encoding HRG) of the polypeptide that is cleaved during post-translational processing of the polypeptide to form the mature HRG polypeptide ligand that binds to $p185^{HER2}$ receptor, although a conventional signal structure is not apparent. Native proHRG, is secreted from the cell but may remain lodged in the membrane because It contains a transmembrane domain and a cytoplasmic region in the carboxyl terminal region of the polypeptide. Thus, In a secreted, soluble version of HRG the carboxyl terminal domain of the molecule, including the transmembrane domain, is ordinarily deleted. This truncated variant HRG polypeptide may be secreted from the cell, provided that the DNA encoding the truncated variant encodes a signal sequence recognized by the host.

HRG of this invention may be expressed not only directly, but also as a fusion with a heterologous polypeptide, preferably a signal sequence or other polypeptide having a specific cleavage site at the N-and/or C-terminis of the mature protein or polypeptide. In general, the signal sequence may be a component of the vector, or it may be a part of HRG DNA that is inserted into the vector. Included within the scope of this invention are HRG with the native signal sequence deleted and replaced with a heterologous signal sequence.

The heterologous signal sequence selected should be one that is recognized and processed, i.e., cleaved by a signal peptidase, by the host cell. For prokaryotic host cells that do not recognize and process the native HRG signal sequence, the signal sequence is substituted by a prokaryotic signal sequence selected, for example, from the group of the alkaline phosphatase, penicillinase, Ipp, or heat-stable enterotoxin II leaders. For yeast secretion the native HRG signal sequence may be substituted by the yeast invertase, alpha factor, or acid phosphatase leaders. In mammalian cell expression the native signal sequence is satisfactory, although other mammalian signal sequences may be suitable.

(ii) Origin of Replication Component

Both expression and cloning vectors generally contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the $2\mu$ plasmid origin is suitable for yeast, and various viral origins (SV40, polyoma, adenovirus, VSV or BPV) are useful for cloning vectors In mammalian cells. Generally, the origin of replication component is not needed for mammalian expression vectors (the SV40 origin may typically be used only because It contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of HRG DNA. However, the recovery of genomic DNA encoding HRG is more complex than that of an exogenously replicated vector because restriction enzyme digestion is required to excise HRG DNA. DNA can be amplified by PCR and directly transfected into the host cells without any replication component.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J. Molec. Appl. Genet.* 1: 327, 1982), mycophenolic acid (Mulligan et al., *Science* 209: 1422, 1980) or hygromycin (Sugden et al., *Mol. Cell. Biol.* 5: 410–413, 1985). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up HRG nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes HRG. Amplification is the process by which genes in greater demand for the production of a protein critical for growth are reiterated in tandem within the chromosomes of successive generations of recombinant cells. Increased quantities of HRG are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA*, 77: 4216, 1980. The transformed cells are then exposed to increased levels of methotrexate. This leads to the synthesis of multiple copies of the DHFR gene, and, concomitantly, multiple copies of other DNA comprising the expression vectors, such as the DNA encoding HRG. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding HRG, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418 (see U.S. Pat. No. 4,965,199).

A suitable selection gene for use in yeast is the trp1 gene present in the yeast plasmid YRp7 (Stinchcomb et al., *Nature*, 282: 39, 1979; Kingsman et al. *Gene,* 7: 141, 1979; or Tschemper et al., *Gene,* 10: 157, 1980). The trp1 gene provides a selection marker for a mutant strain of yeast lacking the ability to grow in tryptophan, for example, ATCC No. 44076 or PEP4-1 (Jones, *Genetics,* 85: 12, 1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(iv) Promoter Component

Expression and cloning vectors usually contain a promoter that is recognized by the host organism and is operably linked to HRG nucleic acid. Promoters are untranslated sequences located upstream (5') to the start codon of a structural gene (generally within about 100 to 1000 bp) that control the transcription and translation of a particular nucleic acid sequence, such as HRG to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to DNA encoding HRG by removing the promoter from the source DNA by restriction enzyme digestion and inserting the isolated promoter sequence into the vector. Both the native HRG promoter sequence and many heterologous promoters may be used to direct amplification and/or expression of HRG DNA. However, heterologous promoters are preferred, as they generally permit greater transcription and higher yields of expressed HRG as compared to the native HRG promoter.

Promoters suitable for use with prokaryotic hosts include the β-lactamase and lactose promoter systems (Chang et al., *Nature*, 275: 615, 1978; and Goeddel et al., *Nature* 281: 544, 1979), alkaline phosphatase, a tryptophan (trp) promoter system (Goeddel, *Nucleic Acids Res.*, 8: 4057, 1980 and EP 36,776) and hybrid promoters such as the tac promoter (deBoer et al., *Proc. Natl. Acad. Sci. USA* 80: 21–25, 1983). However, other known bacterial promoters are suitable. Their nucleotide sequences have been published, thereby enabling a skilled worker operably to ligate them to DNA encoding HRG (Siebenlist et al., *Cell* 20: 269, 1980) using linkers or adaptors to supply any required restriction sites. Promoters for use in bacterial systems also generally will contain a Shine-Dalgarno (S.D.) sequence operably linked to the DNA encoding HRG.

Suitable promoting sequences for use with yeast hosts include the promoters for 3-phosphoglycerate kinase (Hitzeman et al., *J. Biol. Chem.*, 255: 2073, 1980) or other glycolytic enzymes (Hess et al., *J. Adv. Enzyme Reg* 7: 149, 1968; and Holland, *Biochemistry* 17: 4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et at, EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT (SEQ ID NO: 1) region where X may be any nucleotide. At the 3' end of most eukaryotic genes is an AATAAA sequence (SEQ ID NO: 2) that may be the signal for addition of the poly A tail to the 3' end of the coding sequence. All of these sequences are suitably inserted into mammalian expression vectors.

HRG gene transcription from vectors in mammalian host cells is controlled by promoters obtained from the genomes of viruses such as polyoma virus, fowlpox virus (UK 2,211, 504, published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with HRG sequence, provided such promoters are compatible with the host cell systems.

The early and late promoters of the SV40 virus are conveniently obtained as an SV40 restriction fragment that also contains the SV40 viral origin of replication (Fiers et al., *Nature*, 273: 113 (1978); Mulligan and Berg, *Science*, 209: 1422–1427 (1980); Pavlakis et al., *Proc. Natl. Acad. Sci. USA*, 78: 7398–7402 (1981)). The immediate early promoter of the human cytomegalovirus is conveniently obtained as a HindIII E restriction fragment (Greenaway et al., *Gene*, 18: 355–360 (1982)). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295: 503–508 (1982) on expressing cDNA encoding immune interferon in monkey cells; Reyes et al., *Nature*, 297: 598–601 (1982) on expression of human β-interferon cDNA in mouse cells under the control of a thymidine kinase promoter from herpes simplex virus; Canaani and Berg, *Proc. Natl. Acad. Sci. USA*, 79: 5166–5170 (1982) on expression of the human interferon β1 gene in cultured mouse and rabbit cells; and Gorman et al., *Proc. Natl. Acad. Sci. USA*, 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding HRG of this invention by higher eukaryotes is often increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins et al., *Proc. Natl. Acad. Sci. USA*, 78: 993, 1981) and 3' (Lusky et al., *Mol. Cell Bio.*, 3: 1108, 1983) to the transcription unit, within an intron (Banerji et al., *Cell*, 33: 729, 1983) as well as within the coding sequence itself (Osborne et al., *Mol. Cell Bio.*, 4: 1293, 1984). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers (see also Yaniv, *Nature*, 297: 17–18 (1982)) on enhancing elements for activation of eukaryotic promoters. The enhancer may be spliced into the vector at a position 5' or 3' to HRG DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding HRG. The 3' untranslated regions also include transcription termination sites.

Construction of suitable vectors containing one or more of the above listed components the desired coding and control sequences employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9: 309 (1981) or by the method of Maxam et al., *Methods in Enzymology* 65: 499 (1980).

Particularly useful in the practice of this invention are expression vectors that provide for the transient expression in mammalian cells of DNA encoding HRG. In general, transient expression involves the use of an expression vector that is able to replicate efficiently In a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of HRG that have HRG-like activity. Such a transient expression system is described in patent application U.S. Ser. No. 07/101,712.

Other methods, vectors, and host cells suitable for adaptation to the synthesis of HRG in recombinant vertebrate cell culture are described in Gething et al., *Nature* 293: 620–625, 1981; Mantei et al., *Nature,* 281: 40–46, 1979; Levinson et al., EP 117,060 and EP 117,058. A particularly useful expression plasmid for mammalian cell culture expression of HRG is pRK5 (EP pub. no. 307,247) or pSVI6B (U.S. Ser. No. 07/441,574, filed 22 Nov. 1989, the disclosure of which is incorporated herein by reference).

D. Selection and Transformation of Host Cells

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli,* Bacilli such as *B. subtilis,* Pseudomonas species such as *P. aeruginosa, Salmonella typhimurium,* or *Serratia marcescans.* One preferred *E. coli* cloning host is *E. coli* 294 (ATCC 31,446), although other strains such as *E. coli* B, *E. coli* $_x$1776 (ATCC 31,537), and *E. coli* W31 10 (ATCC 27,325) are suitable. These examples are illustrative rather than limiting. Preferably the host cell should secrete minimal amounts of proteolytic enzymes. Alternatively, in vitro methods of cloning, e.g., PCR or other nucleic acid polymerase reactions, are suitable.

In addition to prokaryotes, eukaryotic microbes such as filamentous fungi or yeast are suitable hosts for HRG-encoding vectors. *Saccharomyces cerevisiae,* or common baker's yeast, is the most commonly used among lower eukaryotic host microorganisms. However, a number of other genera, species, and strains are commonly available and useful herein, such as *Schizosaccharomyces pombe* (Beach and Nurse, *Nature,* 290: 140 (1981); EP 139,383, published May 2, 1985), Kluyveromyces hosts (U.S. Ser. No. 4,943,529) such as, e.g., *K. lactis* (Louvencourt et al., *J. Bacteriol.,* 737 (1983); *K. fragilis, K. bulgaricus, K. thermotolerans,* and *K. marxianus, yarrowia* (EP 402,226); *Pichia pastoris* (EP 183,070), Sreekrishna et al., *J. Basic Microbiol.,* 28: 265–278 (1988); Candida, *Trichoderma reesia* (EP 244,234); *Neurospora crassa* (Case et al., *Proc. Natl. Acad. Sci. USA,* 76: 5259–5263 (1979), and filamentous fungi such as, e.g., Neurospora, Penicillium, Tolypocfadium (WO 91/00357, published 10 Jan. 1991), and Aspergillus hosts such as *A. nidulans* (Ballance et al., *Biochem. Biophys. Res. Commun.,* 112: 284–289 (1983); Tilburn et al., *Gene,* 26: 205–221 (1983); Yelton et al., *Proc. Natl. Acad. Sci. USA,* 81: 1470–1474 (1984) and *A. niger* (Kelly and Hynes, *EMBO J.,* 4: 475–479 (1985)).

Suitable host cells for the expression of glycosylated HRG polypeptide are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive Insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified (see, e.g., Luckow et al., *Bio/Technology,* 6: 47–55 (1988); Miller et al., in *Genetic Engineering,* Setlow, J. K. et al., eds., Vol. 8 (Plenum Publishing, 1986), pp. 277–279; and Maeda et al., *Nature,* 315: 592–594 (1985)). A variety of such viral strains are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can be utilized as hosts. Typically, plant cells are transfected by incubation with certain strains of the bacterium *Agrobacterium tumefaciens,* which has been previously manipulated to contain HRG DNA. During incubation of the plant tell culture with *A. tumefaciens,* the DNA encoding HRG is transferred to the plant cell host such that it is transfected, and will, under appropriate conditions, express HRG DNA. In addition, regulatory and signal sequences compatible with plant cells are available, such as the nopaline synthase promoter and polyadenylation signal sequences (Depicker et al. *J. Mol. Appl. Gen.,* 1: 561 [1982]). In addition, DNA segments isolated from the upstream region of the T-DNA 780 gene are capable of activating or increasing transcription levels of plant-expressible genes in recombinant DNA-containing plant tissue (see EP 321,196, published 21 Jun. 1989).

However, interest has been greatest in vertebrate cells, and propagation of vertebrate cells in culture (tissue culture) has become a routine procedure in recent years (*Tissue Culture,* Academic Press, Kruse and Patterson, editors (1973)). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.,* 36: 59, 1977); baby hamster kidney cells (BHK, ATCC CCL 10); Chinese hamster ovary cells/ -DHFR (CHO, Urlaub and Chasin, *Proc. Natl. Acad. Sci. USA,* 77: 4216 [1980]); mouse sertoli cells (TM4, Mather, *Biol. Reprod.,* 23: 243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383: 44–68 [1982]); MRC 5 cells; FS4 cells; and a human hepatoma cell line (Hep G2). Preferred host cells are human embryonic kidney 293 and Chinese hamster ovary cells.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO$_4$ and electroporation. Successful transfection is generally recognized when any indication of the operation of this vector occurs within the host cell.

Transformation means introducing DNA into an organism so that the DNA is replicable, either as an extrachromosomal element or by chromosomal integration. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium fumefaciens* is used for transformation of certain plant cells, as described by Shaw et al., *Gene,* 23: 315 (1983) and WO 89/05859, published 29 Jun. 1989. For mammalian cells without such cell walls, the calcium phosphate precipitation method described in sections 16.30–16.37 of Sambrook et al., supra, is preferred. General aspects of mammalian cell host system transformations have been described by Axel in U.S. Pat. No. 4,399,216, issued 16 Aug. 1983. Transformations Into yeast are typically carried out according to the method of Van Solingen et al., *J. Bact.,* 130: 946 (1977) and Hsiao et al., *Proc. Natl. Acad. Sci. (USA),* 76: 3829 (1979). However, other methods for introducing DNA into cells such as by nuclear injection, electroporation, or protoplast fusion may also be used.

E. Culturing the Host Cells

Prokaryotic cells used to produce HRG polypeptide of this invention are cultured in suitable media as described generally in Sambrook et al., supra.

The mammalian host cells used to produce HRG of this invention may be cultured in a variety of media. Commercially available media such as Ham's F10 (Sigma), Minimal Essential Medium (IMEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.,* 58: 44 (1979), Barnes and Sato, *Anal. Biochem.,* 102: 255 (1980), U.S. Pat. Nos. 4,767,704; 4,657,866; 4,927,762; or 4,560,655; WO 90/03430; WO 87/00195; U.S. Pat. Re. 30,985; or copending U.S. Ser. Nos. 07/592,107 or 07/592,141, both filed on 3 Oct. 1990, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

It is further envisioned that HRG of this invention may be produced by homologous recombination, or with recombinant production methods utilizing control elements introduced into cells already containing DNA encoding HRG currently in use in the field. For example, a powerful promoter/enhancer element, a suppressor, or an exogenous transcription modulatory element is inserted in the genome of the intended host cell in proximity and orientation sufficient to influence the transcription of DNA encoding the desired HRG. The control element does not encode HRG of this invention, but the DNA is present in the host cell genome. One next screens for cells making HRG of this invention, or increased or decreased levels of expression, as desired.

F. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA,* 77: 5201–5205 [1980]), dot blotting (DNA analysis), or in situ hybridization, using an appropriately labeled probe based on the sequences provided herein. Various labels may be employed, most commonly radioisotopes, particularly $^{32}$p. However, other techniques may also be employed, such as using biotin-modified nucleotides for introduction Into a polynucleotide. The biotin then serves as the site for binding to avidin or antibodies which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled where the labels are usually visually detectable such as enzymatic labels, fluorescent labels, luminescent labels, and the like. A particularly sensitive staining technique suitable for use in the present invention is described by Hsu et al., *Am. J. Clin. Path.,* 75: 734–738 (1980).

Antibodies useful for immunohistochemical staining and/or assay of sample fluids may be either monoclonal or polyclonal, and may be prepared in any mammal. Conveniently, the antibodies may be prepared against a native HRG polypeptide or against a synthetic peptide based on the DNA sequences provided herein as described further in Section 4 below.

G. Purification of The Heregulin Polypeptide

HRG is recovered from a cellular membrane fraction. Alternatively, a proteolytically cleaved or a truncated expressed soluble HRG fragment or subdomain are recovered from the culture medium as soluble polypeptides.

When HRG is expressed in a recombinant cell other than one of human origin, HRG is completely free of proteins or polypeptides of human origin. However, it is desirable to purify HRG from recombinant cell proteins or polypeptides to obtain preparations that are substantially homogeneous as to HRG. As a first step, the culture medium or lysate is centrifuged to remove particulate cell debris. The membrane and soluble protein fractions are then separated. HRG is then purified from both the soluble protein fraction (requiring the presence of a protease) and from the membrane fraction of the culture lysate, depending on whether HRG is membrane bound. The following procedures are exemplary of suitable purification procedures: fractionation on immunoaffinity or ion-exchange columns; ethanol precipitation; reversed phase HPLC; chromatography on silica, heparin sepharose or on a cation exchange resin such as DEAE; chromatofocusing; SDS-PAGE; ammonium sulfate precipitation; and gel filtration using, for example, Sephadex G-75. HRG variants in which residues have been deleted, inserted or substituted are recovered in the same fashion as the native HRG, taking account of any substantial changes in properties occasioned by the variation. For example, preparation of a HRG fusion with another protein or polypeptide, e.g., a bacterial or viral antigen, facilitates purification; an immunoaffinity column containing antibody to the antigen can be used to adsorb the fusion. Immunoaffinity columns such as a rabbit polyclonal anti-HRG column can be employed to absorb HRG variant by binding it to at least one remaining immune epitope. A protease inhibitor such as phenylmethylsulfonylfluoride (PMSF) also may be useful to inhibit proteolytic degradation during purification, and antibiotics may be included to prevent the growth of adventitious contaminants. One skilled in the art will appreciate that purification methods suitable for native HRG may require modification to account for changes in the character of HRG variants upon expression in recombinant cell culture.

H. Covalent Modifications of HRG

Covalent modifications of HRG polypeptides are included within the scope of this invention. Both native HRG and amino acid sequence variants of HRG optionally are covalently modified. One type of covalent modification included within the scope of this invention is a HRG polypeptide fragment. HRG fragments, such as HRG-GDF, having up to about 40 amino acid residues are conveniently prepared by chemical synthesis, or by enzymatic or chemical cleavage of the full-length HRG polypeptide or HRG variant polypeptide. Other types of covalent modifications of HRG or fragments thereof are introduced into the molecule by reacting targeted amino acid residues of HRG or fragments thereof with an organic derivatizing agent that is capable of reacting with selected side chains or the N- or C-terminal residues.

Cysteinyl residues most commonly are reacted with a-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, $\neq$-bromo-$\beta$-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing $\alpha$-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125I or $^{131}$I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking HRG to a water-insoluble support matrix or surface for use in the method for purifying anti-HRG antibodies, and vice versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio] propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the $\alpha$-amino groups of lysine, arginine, and histidine side chains (T. E. Creighton, *Proteins: Structure and Molecular Properties,* W. H. Freeman & Co., San Francisco, pp. 79–86 [1983]), acetylation of the N-terminal amine, and amidation of any C-terminal carboxyl group.

HRG optionally is fused with a polypeptide heterologous to HRG. The heterologous polypeptide optionally is an anchor sequence such as that found in the decay accelerating system (DAF); a toxin such as ricin, pseudomonas exotoxin, gelonin, or other polypeptide that will result in target cell death. These heterologous polypeptides are covalently coupled to HRG through side chains or through the terminal residues. Similarly, HRG is conjugated to other molecules toxic or inhibitory to a target mammalian cell, e.g. such as tricothecenes, or antisense DNA that blocks expression of target genes.

HRG also is covalently modified by altering its native glycosylation pattern. One or more carbohydrate substitutents are modified by adding, removing or varying the monosaccharide components at a given site, or by modifying residues in HRG such that glycosylation sites are added or deleted.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Glycosylation sites are added to HRG by altering its amino acid sequence to contain one or more of the above-described tri-peptide sequences (for N-linked glycosylation sites). The alteration may also be made by the addition of, or substitution by, one or more serine or threonine residues to HRG (for O-linked glycosylation sites). For ease, HRG is preferably altered through changes at the DNA level, particularly by mutating the DNA encoding HRG at preselected bases such that codons are generated that will translate Into the desired amino acids.

Chemical or enzymatic coupling of glycosides to HRG increases the number of carbohydrate substituents. These procedures are advantageous in that they do not require production of the polypeptide in a host cell that is capable of N- and O- linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, published 11 Sep. 1987, and in Aplin and Wriston (*CRC Crit. Rev. Biochem.,* pp. 259–306 [1981]).

Carbohydrate moieties present on an HRG also are removed chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al. (*Arch. Biochem. Biophys.,* 259: 52 [1987]) and by Edge et al. (*Anal. Biochem.,* 118: 131 [1981]). Carbohydrate moieties are removed from HRG by a variety of endo- and exo- glycosidases as described by Thotakura et al. (*Meth. Enzymol.,* 138: 350 [1987]).

Glycosylation added during expression in cells also is suppressed by tunicamycin as described by Duskin et al. (*J. Biol. Chem.,* 257: 3105 [1982]). Tunicamycin blocks the formation of protein-N-glycoside linkages.

HRG also is modified by linking HRG to various non-proteinaceous polymers, e.g., polyethylene glycol, polypropylene glycol or polyoxyalkylenes, in the manner set forth in U.S. Pat. Nos. 4,640,835; 4,496,689; 4,301,144; 4,670, 417; 4,791,192 or 4,179,337.

One preferred way to increase the in vivo circulating half life of non-membrane bound HRG is to conjugate it to a polymer that confers extended half-life, such as polyethylene glycol (PEG). (Maxfield, et al., Polymer 16,505–509 [1975]; Bailey, F. E., et al., in Nonionic Surfactants [Schick, M. J., ed.] pp.794–821 [1967]; Abuchowski, A. et al., J. Biol. Chem. 252: 3582–3586 [1977]; Abuchowski, A. et al., *Cancer Biochem. Biophys.* 7: 175–186 [1984]; Katre, N. V. et al., *Proc. Natl. Acad. Sci.,* 84: 1487–1491 [1987]; Goodson, R. et al. *Bio Technology,* 8: 343–346: [1990]). Conjugation to PEG also has been reported to have reduced immunogenicity and toxicity (Abuchowski, A. et al., *J. Biol. Chem.,* 252: 3578–3581 [1977]).

HRG also is entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Osol, A., Ed., (1980).

HRG is also useful in generating antibodies, as standards in assays for HRG (e.g., by labeling HRG for use as a standard in a radioimmunoassay, enzyme-linked immunoassay, or radioreceptor assay), in affinity purification techniques, and in competitive-type receptor binding assays when labeled with radioiodine, enzymes, fluorophores, spin labels, and the like.

Those skilled in the art will be capable of screening variants in order to select the optimal variant for the purpose intended. For example, a change in the immunological character of HRG, such as a change in affinity for a given antigen or for the HER2 receptor, is measured by a competitive-type immunoassay using a standard or control such as a native HRG (in particular native HRG-GFD). Other potential modifications of protein or polypeptide properties such as redox or thermal stability, hydrophobicity, susceptibility to proteolytic degradation, stability in recombinant cell culture or in plasma, or the tendency to aggregate with carriers or into multimers are assayed by methods well known in the art.

1. Therepeutic use of Heregulin Ligands

While the role of the $p185^{HER2}$ and its ligands is unknown in normal cell growth and differentiation, it is an object of the present invention to develop therapeutic uses for the $p185^{HER2}$ ligands of the present invention in promoting normal growth and development and in inhibiting abnormal growth, specifically in malignant or neoplastic tissues.

2. Therapeutic Compositions and Administration of HRG

Therapeutic formulations of HRG or HRG antibody are prepared for storage by mixing the HRG protein having the desired degree of purity with optional physiologically acceptable carriers, excipients, or stabilizers (*Remington's Pharmaceutical Sciences,* supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides (to prevent methoxide formation); proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

HRG or HRG antibody to be used for in vivo administration must be sterile. This is readily accomplished by filtration through sterile filtration membranes, prior to or following lyophilization and reconstitution. HRG or antibody to an HRG ordinarily will be stored in lyophilized form or in solution.

Therapeutic HRG, or HRG specific antibody compositions generally are placed into a container having a sterile access port, for example, an intravenous solution bag or vial having a stopper pierceable by a hypodermic injection needle.

HRG, its antibody or HRG variant when used as an antagonist may be optionally combined with or administered in concert with other agents known for use in the treatment of malignacies. When HRG is used as an agonist to stimulate the HER2 receptor, for example in tissue cultures, it may be combined with or administered in concert with other compositions that stimulate growth such as PDGF, FGF, EGF, growth hormone or other protein growth factors.

The route of HRG or HRG antibody administration Is in accord with known methods, e.g., injection or infusion by intravenous, intraperitoneal, intracerebral, intramuscular, intraocular, intraarterial, or intralesional routes, or by sustained release systems as noted below. HRG is administered continuously by Infusion or by bolus injection. HRG antibody is administered in the same fashion, or by administration into the blood stream or lymph.

Suitable examples of sustained-release preparations Include semipermeable matrices of solid hydrophobic polymers containing the protein, which matrices are in the form of shaped articles, e.g. films, or microcapsules. Examples of sustained-release matrices include polyesters, hydrogels [e.g., poly(2-hydroxyethyl-methacrylate) as described by Langer et al., *J. Biomed. Mater. Res.,* 15: 167–277 (1981) and Langer, *Chem. Tech.,* 12: 98–105 (1982) or poly (vinylalcohol)], polylactides (U.S. Pat. No. 3,773,919, EP 58,481), copolymers of L-glutamic acid and gamma ethyl-L-glutamate (Sidman et al., *Biopolymers,* 22: 547–556 [1983]), non-degradable ethylene-vinyl acetate (Langer at al., supra), degradable lactic acid-glycolic acid copolymers such as the Lupron Depot™ (injectable microspheres composed of lactic acid-glycolic acid copolymer and leuprolide acetate), and poly-D-(–)-3-hydroxybutyric acid (EP 133, 988). While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity.

Rational strategies can be devised for protein stabilization depending on the mechanism involved. For example, If the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release HRG or antibody compositions also include liposomally entrapped HRG or antibody. Liposomes containing HRG or antibody are prepared by methods known per se: DE 3,218,121; Epstein et al., *Proc. Natl. Acad. Sci. USA,* 82: 3688–3692 (1985); Hwang et al., *Proc. Natl. Acad. Sci. USA,* 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamelar type in which the lipid content is greater than about 30 mol. % cholesterol, the selected proportion being adjusted for the optimal HRG therapy. Liposomes with enhanced circulation time are disclosed in U.S. Pat. No. 5,013,556.

Another use of the present invention comprises Incorporating HRG polypeptide or antibody Into formed articles. Such articles can be used in modulating cellular growth and development. In addition, cell growth and division and tumor invasion may be modulated with these articles.

An effective amount of HRG or antibody to be employed therapeutically will depend, for example, upon the therapeutic objectives, the route of administration, and the condition of the patient. Accordingly, It will be necessary for the therapist to titer the dosage and modify the route of administration as required to obtain the optimal therapeutic effect. A typical daily dosage might range from about 1 $\mu$g/kg to up to 100 mg/kg or more, depending on the factors mentioned above. Typically, the clinician will administer HRG or antibody until a dosage is reached that achieves the desired effect. The progress of this therapy is easily monitored by conventional assays.

3. Heregulin Antibody Preparation and Therapeutic Use

The antibodies of this invention are obtained by routine screening. Polyclonal antibodies to HRG generally are raised in animals by multiple subcutaneous (sc) or intraperitoneal (ip) injections of HRG and an adjuvant. It may be useful to conjugate HRG or an HRG fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

The route and schedule of immunizing an animal or removing and culturing antibody-producing cells are generally in keeping with established and conventional techniques for antibody stimulation and production. While mice are frequently immunized, it is contemplated that any mammalian subject including human subjects or antibody-producing cells obtained therefrom can be immunized to generate antibody producing cells.

Subjects are typically immunized against HRG or its immunogenic conjugates or derivatives by combining 1 mg or 1 $\mu$g of HRG immunogen (for rabbits or mice, respectively) with 3 volumes of Freund's complete adjuvant and injecting the solution intradermally at multiple sites.

One month later the subjects are boosted with ⅕ to ⅒ the original amount of immunogen in Freund's complete adjuvant (or other suitable adjuvant) by subcutaneous injection at multiple sites. 7 to 14 days later animals are bled and the serum is assayed for anti-HRG antibody titer. Subjects are boosted until the titer plateaus. Preferably, the subject is boosted with a conjugate of the same HRG, but conjugated to a different protein and/or through a different cross-linking agent. Conjugates also can be made in recombinant cell culture as protein fusions. Also, aggregating agents such as alum are used to enhance the immune response.

After immunization, monoclonal antibodies are prepared by recovering immune lymphoid cells--typically spleen cells or lymphocytes from lymph node tissue--from immunized animals and immortalizing the cells in conventional fashion, e.g., by fusion with myeloma cells or by Epstein-Barr (EB)-virus transformation and screening for clones expressing the desired antibody. The hybridoma technique described originally by Kohler and Milstein, *Eur. J. Immunol.* 6: 511 (1976) has been widely applied to produce hybrid cell lines that secrete high levels of monoclonal antibodies against many specific antigens.

It is possible to fuse cells of one species with another. However, it is preferable that the source of the immunized antibody producing cells and the myeloma be from the same species.

Hybridoma cell lines producing antiHRG are identified by screening the culture supernatants for antibody which binds to HRG. This is routinely accomplished by conventional immunoassays using soluble HRG preparations or by FACS using cell-bound HRG and labelled candidate antibody.

The hybrid cell lines can be maintained in culture in vitro in cell culture media. The cell lines of this invention can be selected and/or maintained in a composition comprising the continuous cell line in hypoxanthine-aminopterin thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody. The secreted antibody is recovered from tissue culture supernatant by conventional methods such as precipitation, Ion exchange chromatography, affinity chromatography, or the like. The antibodies described herein are also recovered from hybridoma cell cultures by conventional methods for purification of IgG or IgM as the case may be that heretofore have been used to purify these immunoglobulins from pooled plasma, e.g., ethanol or polyethylene glycol precipitation procedures. The purified antibodies are sterile filtered, and optionally are conjugated to a detectable marker such as an enzyme or spin label for use in diagnostic assays of HRG in test samples.

While mouse monoclonal antibodies routinely are used, the invention is not so limited; in fact, human antibodies may be used and may prove to be preferable. Such antibodies can be obtained by using human hybridomas (Cote et al., *Monoclonal Antibodies and Cancer Therapy*, Alan R. Liss, p. 77 (1985)). Chimeric antibodies, Cabilly et al., U.S. Patent (Morrison et al., *Proc. Natl. Acad. Sci.*, 81: 6851 (1984); Neuberger et al., *Nature* 312: 604 (1984); Takeda et al., *Nature* 314: 452 (1985)) containing a murine anti-HRG variable region and a human constant region of appropriate biological activity (such as ability to activate human complement and mediate ADCC) are within the scope of this invention, as are humanized anti-HRG antibodiesproduced by conventional CRD-grafting methods.

Techniques for creating recombinant DNA versions of the antigen-binding regions of antibody molecules (known as Fab or variable regions fragments) which bypass the generation of monoclonal antibodies are encompassed within the practice of this invention. One extracts antibody-specific messenger RNA molecules from Immune system cells taken from an immunized subject, transcribes these Into complementary DNA (cDNA), and clones the cDNA into a bacterial expression system and selects for the desired binding characteristic. The Scripps/Stratagene method uses a bacteriophage lambda vector system containing a leader sequence that causes the expressed Fab protein to migrate to the periplasmic space (between the bacterial cell membrane and the cell wall) or to be secreted. One can rapidly generate and screen great numbers of functional Fab fragments to identify those which bind HRG with the desired characteristics.

Antibodies specific to HRG-α, HRG-β1, HRG-β2 and HRG-β3 may be produced and used in the manner described above. HRG-α, HRG-β1, HRG-β2 and HRG-β3 specific antibodies of this invention preferably do not cross-react with other members of the EGF family (FIG. 6) or with each other.

Antibodies capable of specifically binding to the HRG-NTD, HRG-GFD or HRG-CTP are of particular interest. Also of interest are antibodies capable of specifically binding to the proteolytic processing sites between the GFD and transmembrane domains. These antibodies are identified by methods that are conventional per se. For example, a bank of candidate antibodies capable of binding to HRG-ECD or proHRG are obtained by the above methods using immunization with full proHRG. These can then be subdivided by their ability to bind to the various HRG domains using conventional mapping techniques. Less preferably, antibodies specific for a predetermined domain are initially raised by immunizing the subject with a polypeptide comprising substantially only the domain in question, e.g. HRG-GFD free of NTD or CTP polypeptides. These antibodies will not require mapping unless binding to a particular epitope is desired.

Antibodies that are capable of binding to proteolytic processing sites are of particular interest. They are produced either by immunizing with an HRG fragment that includes the CTP processing site, with intact HRG, or with HRG-NTD-GFD and then screening for the ability to block or inhibit proteolytic processing of HRG into the NTD-GFD fragment by recombinant host cells or isolated cell lines that are otherwise capable of processing HRG to the fragment. These antibodies are useful for suppressing the release of NTD-GFD and therefore are promising for use in preventing the release of NTD-GFD and stimulation of the HER-2 receptor. They also are useful in controlling cell growth and replication. Anti-GFD antibodies are useful for the same reasons, but may not be as efficient biologically as antibodies directed against a processing site.

Antibodies are selected that are capable of binding only to one of the members of the HRG family, e.g. HRG-alpha or any one of the HRG-beta isoforms. Since each of the HRG family members has a distinct GFD-transmembrane domain cleavage site, antibodies directed specifically against these unique sequences will enable the highly specific inhibition of each of the GFDs or processing sites, and thereby refine the desired biological response. For example, breast carcinoma cells which are HER-2 dependent may in fact be activated only by a single GFD isotype or, if not, the activating GFD may originate only from a particular processing sequence, either on the HER-2 bearing cell itself or on a GFD-generating cell. The identification of the target activating GFD or processing site is a straight-forward matter of analyzing HER-2 dependent carcinomas, e.g., by analyzing the tissues for the presence of a particular GFD family member associated with the receptor, or by analyzing the tissues for expression of an HRG family member (which then would serve as the therapeutic target). These selective antibodies are produced in the same fashion as described above, either by immunization with the target sequence or domain, or by selecting from a bank of antibodies having broader specificity.

As described above, the antibodies should have high specificity and affinity for the target sequence. For example, the antibodies directed against GFD sequences should have greater affinity for the GFD than GFD has for the HER-2 receptor. Such antibodies are selected by routine screening methods.

4. Non-Therapeutic Uses of Heregulin and Its Antibodies

The nucleic acid encoding HRG may be used as a diagnostic for tissue specific typing. For example, such procedures as in situ hybridization, and Northern and Southern blotting, and PCR analysis may be used to determine whether DNA and/or RNA encoding HRG are present in the cell type(s) being evaluated. In particular, the nucleic acid may be useful as a specific probe for certain types of tumor cells such as, for example, mammary gland, gastric and colon adenocarcinomas, salivary gland and other tissues containing the $p185^{HER2}$.

Isolated HRG may be used in quantitative diagnostic assays as a standard or control against which samples containing unknown quantities of HRG may be compared.

Isolated HRG may be used as a growth factor for invitro cell culture, and invivo to promote the growth of cells containing $p185^{HER2}$ or other analogous receptors.

HRG antibodies are useful in diagnostic assays for HRG expression in specific cells or tissues. The antibodies are labeled in the same fashion as HRG described above and/or are immobilized on an insoluble matrix.

HRG antibodies also are useful for the affinity purification of HRG from recombinant cell culture or natural sources. HRG antibodies that do not detectably cross-react with other HRG can be used to purify HRG free from other known ligands or contaminating protein.

Suitable diagnostic assays for HRG and its antibodies are well known per se. Such assays include competitive and sandwich assays, and steric inhibition assays. Competitive and sandwich methods employ a phase-separation step as an integral part of the method while steric inhibition assays are conducted in a single reaction mixture. Fundamentally, the same procedures are used for the assay of HRG and for substances that bind HRG, although certain methods will be favored depending upon the molecular weight of the substance being assayed. Therefore, the substance to be tested is referred to herein as an analyte, irrespective of its status otherwise as an antigen or antibody, and proteins that bind to the analyte are denominated binding partners, whether they be antibodies, cell surface receptors, or antigens.

Analytical methods for HRG or its antibodies all use one or more of the following reagents: labeled analyte analogue, immobilized analyte analogue, labeled binding partner, immobilized binding partner and steric conjugates. The labeled reagents also are known as "tracers."

The label used (and this is also useful to label HRG encoding nucleic acid for use as a probe) is any detectable functionality that does not interfere with the binding of analyte and its binding partner. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. Nos. 3,940,475 (fluorimetry) and 3,645,090 (enzymes); Hunter et al., *Nature*, 144: 945 (1962); David et al., *Biochemistry*, 13: 1014–1021 (1974); Pain et al., *J. Immunol. Methods*, 40: 219–230 (1981); and Nygren, *J. Histochem. and Cytochem.*, 30: 407–412 (1982). Preferred labels herein are enzymes such as horseradish peroxidase and alkaline phosphatase. The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology*, ed. J. J. Langone and H.

Van Vunakis, Vol. 73 (Academic Press, New York, N.Y., 1981), pp. 147–166. Such bonding methods are suitable for use with HRG or its antibodies, all of which are proteinaceous.

Immobilization of reagents is required for certain assay methods. Immobilization entails separating the binding partner from any analyte that remains free in solution. This conventionally is accomplished by either insolubilizing the binding partner or analyte analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the partner or analogue afterward, e.g., by immunoprecipitation.

Other assay methods, known as competitive or sandwich assays, are well established and widely used in the commercial diagnostics industry. Competitive assays rely on the ability of a tracer analogue to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, HRG or its immunologically active fragments are conjugated with a bifunctional organic bridge to an enzyme such as peroxidase. Conjugates are selected for use with anti-HRG so that binding of the anti-HRG antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of HRG or HRG antibodies. In sequential sandwich assays an immobilized binding partner is used to adsorb test sample analyte, the test sample is removed as by washing, the bound analyte is used to adsorb labeled binding partner, and bound material is then separated from residual tracer. The amount of bound tracer is directly proportional to test sample analyte. In "simultaneous" sandwich assays the test sample is not separated before adding the labeled binding partner. A sequential sandwich assay using an anti-HRG monoclonal antibody as one antibody and a polyclonal anti-HRG antibody as the other is useful in testing samples for HRG activity.

The foregoing are merely exemplary diagnostic assays for HRG and antibodies. Other methods now or hereafter developed for the determination of these analytes are included within the scope hereof, including the bioassays described above.

HRG polypeptides may be used for affinity purification of receptors such as the $p185^{HER2}$ and other similar receptors that have a binding affinity for HRG, and more specifically HRG-α, HRG-β1, HRG-β2 and HRG-β3. HRG-α, HRG-β1, HRG-β2 and HRG-β3 may be used to form fusion polypeptides wherein HRG portion is useful for affinity binding to nucleic acids and to heparin.

HRG polypeptides may be used as ligands for competitive screening of potential agonists or antagonists for binding to $p_{185}^{HER2}$. HRG variants are useful as standards or controls in assays for HRG provided that they are recognized by the analytical system employed, e.g. an anti-HRG antibody. Antibody capable of binding to denatured HRG or a fragment thereof, is employed in assays in which HRG is denatured prior to assay, and in this assay the denatured HRG or fragment is used as a standard or control. Preferably, HRG-α, HRG-β1, HRG-β2 and HRG-β3 are detectably labelled and a competition assay for bound $p_{185}^{HER2}$ is conducted using standard assay procedures.

The methods and procedures described herein with HRG-α may be applied similarly to HRG-β1, HRG-β2 and HRG-β3 and to other novel HRG ligands and to their variants. All references cited in this specification are expressly incorporated by reference. The following examples are offered by way of illustration and not by way of limitation.

EXAMPLES

Example 1

Preparation of Breast Cancer Cell Supernatants

Heregulin-α was isolated from the supernatant of the human breast carcinoma MDA-MB-231. HRG was released into and isolated from the cell culture medium.

a. Cell Culture

MDA-MB-231, human breast carcinoma cells, obtainable from the American Type Culture Collection (ATCC HTB 26), were initially scaled-up from 25 cm² tissue culture flasks to 890 cm² plastic roller bottles (Corning, Corning, N.Y.) by serial passaging and the seed train was maintained at the roller bottle scale. To passage the cells and maintain the seed train, flasks and roller bottles were first rinsed with phosphate buffered saline (PBS) and then Incubated with trypsin/EDTA (Sigma, St. Louis, Mo.) for 1–3 minutes at 37° C. The detached cells were then pipetted several times in fresh culture medium containing fetal bovine serum (FBS), (Gibco, Grand Island, N.Y.) to break up cell clumps and to inactivate the trypsin. The cells were finally split at a ratio of 1:10 Into fresh medium, transferred into new flasks or bottles, incubated at 37° C., and allowed to grow until nearly confluent. The growth medium in which the cells were maintained was a combined DME/Ham's-F-12 medium formulation modified with respect to the concentrations of some amino acids, vitamins, sugars, and salts, and supplemented with 5% FBS. The same basal medium is used for the serum-free ligand production and is supplemented with 0.5% Primatone RL (Sheffield, Norwich, N.Y.).

b. Large Scale Production

Large scale MDA-MB-231 cell growth was obtained by using Percell Biolytica microcarriers (Hyclone Laboratories, Logan, Utah) made of weighted cross-linked gelatin. The microcarriers were first hydrated, autoclaved, and rinsed according to the manufacturer's recommendations. Cells from 10 roller bottles were trypsinized and added into an inoculation spinner vessel which contained three liters of growth medium and 10–20 g of hydrated microcarriers. The cells were stirred gently for about one hour and transferred into a ten-liter instrumented fermenter containing seven liters of growth medium. The culture was agitated at 65–75 rpm to maintain the microcarriers in suspension. The fermenter was controlled at 37° C. and the pH was maintained at 7.0–7.2 by the addition of sodium carbonate and $CO_2$. Air and oxygen gases were sparged to maintain the culture at about 40% of air saturation. The cell population was monitored microscopically with a fluorescent vital stain (fluorescein diacetate) and compared to trypan blue staining to assess the relative cell viability and the degree of microcarrier invasion by the cells. Changes in cell-microcarrier aggregate size were monitored by microscopic photography.

Once the microcarriers appeared 90–100% confluent, the culture was washed with serum-free medium to remove the serum. This was accomplished by stopping the agitation and other controls to allow the carriers to settle to the bottom of the vessel. Approximately nine liters of the culture supernatant were pumped out of the vessel and replaced with an equal volume of serum-free medium (the same basal medium described as above supplemented either with or without Primatone RL). The microcarriers were briefly resuspended and the process was repeated until a 1000 fold removal of FBS was achieved. The cells were then incubated in the serum-free medium for 3–5 days. The glucose concentration in the culture was monitored daily and supplemented with additions of glucose as needed to maintain the concentration In the fermenter at or above 1 g/L. At the time of harvest, the microcarriers were settled as described above and the supernatant was aseptically removed and stored at 2°–8° C. for purification. Fresh serum-free medium was replaced into the fermenter, the microcarriers were resuspended, and the culture was Incubated and harvested as before. This procedure could be repeated four times.

Example 2

Purification of Growth Factor Activity

Conditioned media (10–20 liters) from MDA-MB-231 cells was clarified by centrifugation at 10,000 rpm in a Sorvall Centrifuge, filtered through a 0.22 micron filter and then concentrated 10–50 (approx. 25) fold with a Minitan Tangential Flow Unit (Millipore Corp.) with a 10 kDa cutoff polysulfone membrane at room temperature. Alternatively, media was concentrated with a 2.5 L Amicon Stirred Cell at 4° C. with a YM3 membrane. After concentration, the media was again centrifuged at 10,000 rpm and the supernatant frozen in 35–50 ml aliquots at −80° C.

Heparin Sepharose was purchased from Pharmacia (Piscataway, N.J.) and was prepared according to the directions of the manufacturer. Five milliliters of the resin was packed into a column and was extensively washed (100 column volumes) and equilibrated with phosphate buffered saline (PBS). The concentrated conditioned media was thawed, filtered through a 0.22 micron filter to remove particulate material and loaded onto the heparin-Sepharose column at a flow rate of 1 ml/min. The normal load consisted of 30–50 mls of 40-fold concentrated media. After loading, the column was washed with PBS until the absorbance at 280 nm returned to baseline before elution of protein was begun. The column was eluted at 1 ml/min with successive salt steps of 0.3M, 0.6M, 0.9M and (optionally) 2.0M NaCl prepared in PBS. Each step was continued until the absorbance returned to baseline, usually 6–10 column volumes. Fractions of 1 milliliter volume were collected. All of the fractions corresponding to each wash or salt step were pooled and stored for subsequent assay in the MDA-MB-453 cell assay.

Figure 1:
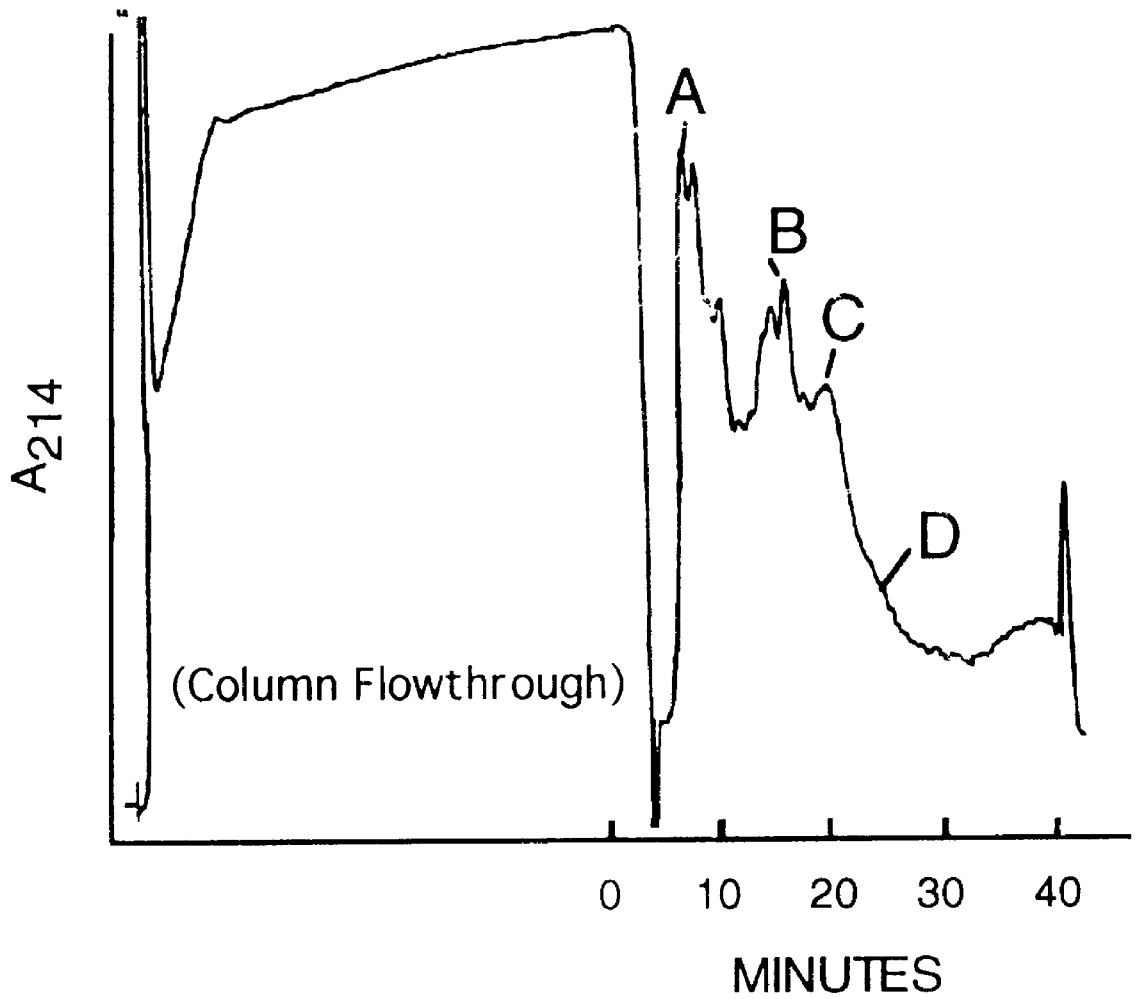
FIG. 1 Purification of Heregulin on PolyAspartic Acid column.

The majority of the tyrosine phosphorylation stimulatory activity was found in the 0.6M NaCl pool which was used for the next step of purification. Active fractions from the heparin-Sepharose chromatography were thawed, diluted three fold with deionized (MilliQ) water to reduce the salt concentration and loaded onto a polyaspartic acid column (PolyCAT A, 4.6×100 mm, PolyLC, Columbia, Md.) equilibrated in 17 mM Na phosphate, pH 6.8. All buffers for this purification step contained 30% ethanol to improve the resolution of protein on this column. After loading, the column was washed with equilibration buffer and was eluted with a linear salt gradient from 0.3M to 0.6M NaCl in 17 mM Na phosphate, pH 6.8, buffer. The column was loaded and developed at 1 ml/min and 1 ml fractions were collected during the gradient elution. Fractions were stored at 4° C. Multiple heparin-Sepharose and PolyCat columns were processed in order to obtain sufficient material for the next purification step. A typical absorbance profile from a Poly-Cat A column is shown in FIG. 1. Aliquots of 10–25 μL were taken from each fraction for assay and SDS gel analysis.

Tyrosine phosphorylation stimulatory activity was found throughout the eluted fractions of the PolyCAT A column with a majority of the activity found in the fractions corresponding to peak C of the chromatogram (salt concentration of approximately 0.45M NaCl). These fractions were pooled and adjusted to 0.1% trifluoracetic acid (TFA) by addition of 0.1 volume of 1% TFA. Two volumes of deionized water were added to dilute the ethanol and salt from the previous step and the sample was subjected to further purification on high pressure liquid chromatography (HPLC) utilizing a C4 reversed phase column (SynChropak RP-4, 4.6×100 mm) equilibrated in a buffer consisting of 0.1% TFA in water with 15% acetonitrile. The HPLC procedure was carried out at room temperature with a flow rate of 1 ml/min. After loading of the sample, the column was re-equilibrated in 0.1% TFA/15% acetonitrile. A gradient of acetonitrile was established such that over a 10 minute period of time the acetonitrile concentration increased from 15 to 25% (1%/min). Subsequently, the column was developed with a gradient from 25 to 40% acetonitrile over 60 min time (0.25/min). Fractions of 1 ml were collected, capped to prevent evaporation, and stored at 4° C. Aliquots of 10 to 50 μL were taken, reduced to dryness under vacuum (SpeedVac), and reconstituted with assay buffer (PBS with 0.1% bovine serum albumin) for the tyrosine phosphorylation assay. Additionally, aliquots of 10 to 50 μL were taken and dried as above for analysis by SDS gel electrophoresis. A typical HPLC profile Is shown in FIG. 2.

A major peak of activity was found in fraction 17 (FIG. 2B). By SDS gel analysis, fraction 17 was found to contain a single major protein species which comigrated with the 45,000 dalton molecular weight standard (FIGS. 2C, 3). In other preparations, the presence of the 45,000 dalton protein comigrated with the stimulation of tyrosine phosphorylation activity in the MDA-MB-453 cell assay. The chromatographic properties of the 45,000 dalton protein were atypical; in contrast to many other proteins in the preparation, the 45,000 dalton protein did not elute from the reversed phase column within 2 or 3 fractions. Instead, it was eluted over 5–10 fractions. This is possibly due to extensive post-translational modifications.

a. Protein Sequence Determination

Fractions containing the 45,000 dalton protein were dried under vacuum for amino acid sequencing. Samples were redissolved in 70% formic acid and loaded into an Applied Biosystems, Inc. Model 470A vapor phase sequencer for N-terminal sequencing. No discernable N-terminal sequence was obtained, suggesting that the N-terminal residue was blocked. Similar results were obtained when the protein was first run on an SDS gel, transblotted to ProBlott membrane and the 45,000 dalton band excised after localization by rapid staining with Coomassie Brilliant Blue.

Internal amino acid sequence was obtained by subjecting fractions containing the 45,000 dalton protein to partial digestion using either cyanogen bromide, to cleave at methionine residues, Lysine-C to cleave at the C-terminal side of lysine residues, or Asp-N to cleave at the N-terminal side of aspartic acid residues. Samples after digestion were sequenced directly or the peptides were first resolved by HPLC chromatography on a Synchrom C4 column (4000A, 2×100 mm) equilibrated in 0.1% TFA and eluted with a 1-propanol gradient in 0.1% TFA. Peaks from the chromatographic run were dried under vacuum before sequencing.

Upon sequencing of the peptide in the peak designated number 15 (lysine C-15), several amino acids were found on each cycle of the run. After careful analysis, it was clear that the fraction contained the same basic peptide with several different N-termini, giving rise to the multiple amino acids in each cycle. After deconvolution, the following sequence was determined (SEQ ID NO. 3):

[A] A E K E K T F [C] V N G G E X F M V K D L X N P
1      5       10       15       20

(Residues in brackets were uncertain while an X represents a cycle In which it was not possible to identify the amino acid.)

The initial yield was 8.5 pmoles. This sequence comprising 24 amino acids did not correspond to any previously known protein. Residue 1 was later found from the cDNA sequence to be Cys and residue 9 was found to be correct. The unknown amino acids at positions 15 and 22 were found to be Cys and Cys, respectively.

Sequencing on samples after cyanogen bromide and Asp-N digestions, but without separation by HPLC, were performed to corroborate the CDNA sequence. The sequences obtained are given in Table I and confirm the sequence for the 45,000 protein deduced from the cDNA sequence. The N-terminal of the protein appears to be blocked with an unknown blocking group. On one occasion, direct sequencing of the 45,000 dalton band from a PVDF blot revealed this sequence with a very small initial yield (0.2 pmole)(SEQ ID NO: 4):

X E X K E (G) (R) G K (G) K (G) K K K E X G X G (K)

(Residues which could not be determined are represented by "X", while tentative residues are in parentheses). This corresponds to a sequence starting at the serine at position 46 near the present N-terminal of HRG cDNA sequence; this suggests that the N terminus of the 45,000 protein is at or before this point in the sequence.

Example 3

Cloning and Sequencing of Human Heregulin

The cDNA cloning of the p185$^{HER2}$ ligand was accomplished as follows. A portion of the lysine C-15 peptide amino acid sequence was decoded in order to design a probe for cDNA's encoding the 45 kD HRG-α ligand. The following 39 residue long eight fold degenerate deoxyoligonucleotide corresponding to the amino acid sequence(SEQ ID NO: 5) NH2- . . . AEKEKTFXVNGGE was chemically synthesized (SEQ ID NO: 6):

3' GCTGAGAAGGAGAAGACCTTCTGT/CGTGAAT/CGGA/
CGGCGAG 5'.

The unknown amino acid residue designated by X in the amino acid sequence was assigned as cysteine for design of the probe. This probe was radioactively phosphorylated and employed to screen by low stringency hybridization an oligo dT primed cDNA library constructed from human MDA-MB-231 cell mRNA in λgt10 (Huyng et al., 1984, In DNA Cloning, Vol 1: A Practical Approach (D. Glover, ed) pp. 49–78. IRL Press, Oxford). Two positive clones designated λgt10her16 and λgt10her13 were identified. DNA sequence analysis revealed that these two clones were identical.

The 2010 basepair cDNA nucleotide sequence of λgt10her16 (FIG. 4) contains a single long open reading frame of 669 amino acids beginning with alanine at nucleotide positions 3–5 and ending with glutamine at nucleotide positions 2007–2009. No stop codon was found in the translated sequence; however, later analysis of heregulin β-type clones indicates that methionine encoded at nucleotide positions 135–137 was the initiating methionine. Nucleotide sequence homology with the probe is found between and including bases 681–719. Homology between those amino acids encoded by the probe and those flanking the probe with the amino acid sequence determined for the lysine C-15 fragment verify that the isolated clone encodes at least the lysine C-fragment of the 45 kD protein.

Hydropathy analysis shows the existence of a strongly hydrophobic amino acid region including residues 287–309 (FIG. 4) indicating that this protein contains a transmembrane or internal signal sequence domain and thus is anchored to the membrane of the cell.

The 669 amino acid sequence encoded by the 2010bp cDNA sequence contains potential sites for asparagine-linked glycosylation (Winzler,R. In Hormonal Proteins and Peptides, (Li, C. H. ed ) pp 1–15 Academic Press, New York (1973)) at positions asparagine 164, 170, 208, 437 and 609. A potential O-glycosylation site (Marshall,R. D. (1974) Biochem. Soc. Symp. 40: 17–26) is presented in the region including a cluster of serine and threonine residues at amino acid positions 209–218. Three sites of potential glycosaminoglycan addition (Goldstein, L. A., et al. (1989) Cell 56: 1063–1072) are positioned at the serine-glycine dipeptides occurring at amino acids 42–43, 64–65 and 151–152. Glycosylation probably accounts for the discrepancy between the calculated NW of about 26 KD for the NTD-GFD (extracellular) region of HRG and the observed NW of about 45 KD for purified HRG.

This amino acid sequence shares a number of features with the epidermal growth factor (EGF) family of transmembrane bound growth factors (Carpenter,G., and Cohen, S. (1979) Ann. Rev. Biochem.48: 193–216; Massenque, J.(1990) J. Biol. Chem. 265: 21393–21396) including 1) the existence of a proform of each growth factor from which the mature form is proteolytically released (Gray,A., Dull, T. J., and Ullrich, A. (1983) Nature 303, 722–725; Bell, G. I. et al., (1986) Nuc. Acid Res., 14: 8427–8446; Derynck, R. et al. (1984) Cell: 287–297); 2) the conservation of six cysteine residues characteristically positioned over a span of approximately 40 amino acids (the EGF-like structural motif) (Savage,R. C., et al. (1973) J. Biol. Chem. 248: 7669–7672); HRG-α cysteines 226, 234, 240, 254, 256 and 265 ); and, 3) the existence of a transmembrane domain occurring proximally on the carboxy-terminal side of the EGF homologous region (FIG. 4 and 6).

Alignment of the amino acid sequences in the region of the EGF motif and flanking transmembrane domain of several human EGF related proteins (FIG. 6) shows that between the first and sixth cysteine of the EGF motif HRG is most similar (50%) to the heparin binding EGF-like growth factor (HB-EGF) (Higashiyama, S. et al. (1991) Science 251: 936–939). In this same region HRG is ~35% homologous to amphiregulin (AR) (Plowman, G. D. et al., (1990) Mol. Cell. Biol. 10: 1969–1981), ~32% homologous to transforming growth factor α(TGF α) (8), 27% homologous with EGF (Bell, G. I. et al., (1986) Nuc. Acid Res., 14: 8427–8446); and 39% homologous to the schwanoma-derived growth factor (Kimura, H., et al., Nature, 348: 257–260, 1990). Disulfide linkages between cysteine residues in the EGF motif have been determined for EGF (Savage, R. C. et al. (1973) J. Biol. Chem. 248: 7669–7672). These disulfides define the secondary structure of this region and demarcate three loops. By numbering the cysteines beginning with 1 on the amino-terminal end, loop 1 is delineated by cysteines 1 and 3; loop 2 by cysteines 2 and 4; and loop 3 by cysteines 5 and 6. Although the exact disulfide configuration in the region for the other members of the family has not been determined, the strict conservation of the six cysteines, as well as several other residues i.e., glycine 238 and 262 and arginine at position 264, indicate that they too most likely have the same arrangement. HRG-α and EGF both have 13 amino acids in loop 1. HB-EGF, amphregulin (AR) and TGF α have 12 amino acids in loop 1. Each member has 10 residues in loop 2 except HRG-α which has 13. All five members have 8 residues in the third loop.

EGF, AR, HB-EGF and TGF-α are all newly synthesized as membrane anchored proteins by virtue of their transmembrane domains. The proproteins are subsequently processed to yield mature active molecules. In the case of TGF-α there is evidence that the membrane associated proforms of the molecules are also biologically active (Brachmann, R.,et al. (1989) Cell 56: 691–700), a trait that may also be the case for HRG-α. EGF is synthesized as a 1168 amino acid transmembrane bound proEGF that is cleaved on the amino-terminal end between arginine 970 and asparagine 971 and at the carboxy-terminal end between arginine 1023 and histidine 1024 (Carpenter,G., and Cohen,S. (1979) Ann. Rev. Biochem.48: 193–216) to yield the 53 amino acid mature EGF molecule containing the three loop, 3 disulfide bond signature structure. The 252 amino acid proAR is cleaved between aspartic acid 100 and serine 101 and between lysine 184 and serine 185 to yield an 84 amino acid form of mature AR and a 78 amino acid form is generated by $NH_2$-terminal cleavage between glutamine 106 and valine 107 (Plowman, G. D. et al., (1990) Mol. Cell. Biol. 10: 1969–1981). HB-EGF is processed from its 208 amino acid primary translation product to its proposed 84 amino acid form by cleavage between arginine 73 and valine 74 and a second site approximately 84 amino acids away in the carboxy-terminal direction (Higashiyama, S., et al., and Klagsburn, M. (1991) Science 251: 936–939). The 160 amino acid proform of TGF α is processed to a mature 50 amino acid protein by cleavages between alanine 39 and valine 40 on one side and downstream cleavage between alanine 89 and valine 90 (Derynck et al., (1984) Cell: 38: 287–297). For each of the above described molecules COOH-terminal processing occurs in the area bounded by the sixth cysteine of the EGF motif and the beginning of the transmembrane domain.

The residues between the first and sixth cysteines of HRGs are most similar (45%) to heparin-binding EGF-like growth factor (HB-EGF). In this same region they are 35% identical to amphiregulin (AR), 32% identical to TGF-α, and 27% identical with EGF. Outside of the EGF motif there is little similarity between HRGs and other members of the EGF family. EGF, AR, HB-EGF and TGF-α are all derived from membrane anchored proproteins which are processed on both sides of the EGF structural unit, yielding 50–84 amino acid mature proteins (16–19). Like other EGF family members, the HRGs appear to be derived from a membrane-bound proform but require only a single cleavage, C-terminal to the cysteine cluster, to produce mature protein.

HRG may exert its biological function by binding to its receptor and triggering the transduction of a growth modulating signal. This It may accomplish as a soluble molecule or perhaps as its membrane anchored form such as is sometimes the case with TGF α (Brachmann, R., et al., (1989) Cell 56: 691–700). Conversely, or in addition to stimulating signal transduction, HRG may be internalized by a target cell where it may then Interact with the controlling regions of other regulatory genes and thus directly deliver its message to the nucleus of the cell. The possibility that HRG mediates some of its effects by a mechanism such as this is suggested by the fact that a potential nuclear location signal (Roberts, Biochem-Biophys Acta (1989) 1008: 263–280) exists in the region around the three lysine residues at positions 58–60 (FIG. 4).

The isolation of full-length cDNA of HRG-α is accomplished by employing the DNA sequence of FIG. 4 to select additional cDNA sequences from the CDNA library constructed from human MDA-MB-231. Full-length cDNA clones encoding HRG-α are obtained by identifying cDNAs encoding HRG-α longer in both the 3' and 5' directions and then splicing together a composite of the different cDNAs. Additional CDNA libraries are constructed as required for this purpose. Following are three types of cDNA libraries that may be constructed: 1) Oligo-dT primed where predominately stretches of polyadenosine residues are primed, 2) random primed using short synthetic deoxyoligonucleotides non-specific for any particular region of the mRNA, and 3) specifically primed using short synthetic deoxyoligonucleotides specific for a desired region of the mRNA. Methods for the isolation of such cDNA libraries were previously described.

Example 4

Detection of HRG-α mRNA Expression by Northern Analyses

Northern blot analysis of MDA-MB-231 and SK-BR-3 cell mRNA under high stringency conditions shows at least five hybridizing bands In MDA-MB-231 mRNA where a 6.4 Kb band predominates: other weaker bands are at 9.4, 6.9, 2.8 and 1.8 Kb (FIG. 5). No hybridizing band is seen in SK-BR-3 mRNA (this cell line overepresses $p185^{HER2}$). The existence of these multiple messages in MDA-MB-231 cells indicates either alternative splicing of the gene, various processing of the genes' primary transcript or the existance of a transcript of another homologous message. One of these messages may encode a soluble non-transmembrane bound form of HRG-α. Such messages (FIG. 5) may be used to produce cDNA encoding soluble non-transmembrane bound forms of HRG-α.

Example 5

Cell Growth Stimulation by Heregulin-α

Several different breast cancer cell lines expressing the EGF receptor or the $p185^{HER2}$ receptor were tested for their sensitivity to growth Inhibition or stimulation by ligand preparations. The cell lines tested were: SK-BR-3 (ATCC HTB 30), a cell line which overexpresses $p185^{HER2}$; MDA-MB-468 (ATCC HTB 132), a line which overexpresses the EGF receptor; and MCF-7 cells (ATCC HTB 22) which have a moderate level of $p185^{HER2}$ expression. These cells were maintained in culture and passaged according to established cell culture techniques. The cells were grown in a 1:1 mixture of DMEM and F-12 media with 10% fetal bovine serum. For the assay, the stock cultures were treated with trypsin to detach the cells from the culture dish, and dispensed at a level of about 20000 cells/well in a ninety-six well microtiter plate. During the course of the growth assay they were maintained in media with 1% fetal bovine serum. The test samples were sterilized by filtration through 0.22 micron filters and they were added to quadruplicate wells and the cells incubated for 3–5 days at 37° C. At the end of the growth period, the media was aspirated from each well and the cells treated with crystal violet (Lewis, G. et al., Cancer Research, 347: 5382–5385 [1987]). The amount of crystal violet absorbance which is proportional to the number of cells in each well was measured on a Flow Plate Reader. Values from replicate wells for each test sample were averaged. Untreated wells on each dish served as controls. Results were expressed as percent of growth relative to the control cells.

The purified HRG-α ligand was tested for activity in the cell growth assay and the results are presented in FIG. 7. At a concentration of approximately 1 nM ligand, both of the cell lines expressing the p185$^{HER2}$ receptor (SK-BR-3 and MCF-7) showed stimulation of growth relative to the controls while the cell type (MDA-MB-468) expressing only the EGF receptor did not show an appreciable response. These results were consistent to those obtained from the autophosphorylation experiments with the various cell lines. These results established that HRG-A ligand is specific for the p185$^{HER2}$ receptor and does not show appreciable interaction with the EGF receptor at these concentrations.

HRG does not compete with antibodies directed against the extra-cellular domain of p185$^{HER2}$, but anti-p185$^{HER2}$. Mabs 2C4 and 7F3 (which are antiproliferative in their own right) do antagonize HRG.

Example 6

Cloning and Sequencing of Heregulin-β1

The isolation of HRG-β1 cDNA was accomplished by employing a hybridizing fragment of the DNA sequence encoding HRG-α to select additional cDNA sequences from the CDNA library constructed from human MDA-MB-231 cells. Clone λher11.1 dbl (heregulin-β1) was identified in a λgt$_{10}$ oligo-dT primed cDNA library derived from MDA MB231 polyA$^+$ mRNA. Radioactively labelled synthetic DNA probes corresponding to the 5' and 3' ends of λher16 (HRG-α) were employed in a hybridization reaction under high stringency conditions to isolate the λher11.1 dbl clone. The DNA nucleotide sequence of the λher11.1 dbl clone is shown in FIG. 8 (SEQ ID NO: 9) HRG-β1 amino acid sequence is homologous to HRG-α from its amino-terminal end at position Asp 15 of HRG-α through the 3'end of HRG-α except at the positions described below. In addition, HRG-β1 encoding DNA extends 189 base pairs longer than λher16 in the 3' direction and supplies a stop codon after Val 675. At nucleotide position 247 of λher11.1 dbl there is a G substituted for A thereby resulting in the substitution of Gln(Q) in place of Arg(R) in HRG-β1 as shown in the second line of FIG. 9 (SEQ ID NO: 8 and SEQ ID NO: 9).

In the area of the EGF motif there are additional differences between HRG-α and HRG-β1. These differences are illustrated below in an expanded view of the homology between HRG-α and HRG-β1 in the region of the EGF motif or the GFD (growth factor domain). The specific sequence shown corresponds to HRG-α amino acids 221–286 shown in FIG. 9. Asterisks indicate identical residues in the comparison below (SEQ ID NO: 10 and SEQ ID NO: 11).

```
HEREGULIN-α   S H L V K C A E K E K T F C V N G G E C
HEREGULIN-β1  * * * * * * * * * * * * * * * * * * * *

HEREGULIN-α   F M V K D L S N P S R Y L C K C Q P G F
HEREGULIN-β1  * * * * * * * * * * * * * * * P N E *

HEREGULIN-α   T G A R C T E N V P M K V Q N Q E K - -
HEREGULIN-β1  * * D * * Q N Y * M A S F Y K H L G I E

HEREGULIN-α   - - - A E E L Y Q K R  (-Transmembrane)
HEREGULIN-β1  F M E * * * * * * * *  (-Transmembrane)
```

Example 7

Expression of Heregulins In *E. Coli*

HRG-α and HRG-β1 have been expressed in *E. coli* using the DNA sequences of FIGS. 4 and 8 encoding heregulin under the control of the alkaline phosphatase promotor and the STII leader sequence. In the initial characterization of heregulin activity, the precise natural amino and carboxy termini of the heregulin molecule were not precisely defined. However, after comparsion of heregulin to EGF and TGF-α sequences, we expected that shortened forms of heregulin starting around Ser 221 and ending around Glu 277 of FIG. 4 may have biological activity. Analogous regions of all heregulins may be identified and expressed. One shortened form was constructed to have an N-terminal Asp residue followed by the residues 221 to 277 of HRG-α. Due to an accidental frame shift mutation following Glu 277, HRG-α sequence was extended by 13 amino acids on the carboxy terminal end. Thus, the carboxy-terminal end was Glu 277 of HRG-α followed by the thirteen amino acid sequence RPNARLPPGVFYC (SEQ ID NO: 20).

Expression of this construct was induced by growth of the cells in phosphate depleted medium for about 20 hours. Recombinant protein was purified by harvesting cell paste and resuspending in 10 mM Tris (pH8), homogenizing, incubating at 4° C. for 40 minutes and followed by centrifuging at 15K rpm (Sorvall). The supernatant was concentrated on a 30K ultrafiltration membrane (Amicon) and the filtrate was applied to a MonoQ column equilibrtated in 10 mM Tris pH8. The flow-through fractions from the MonoQ column were adjusted to 0.05% TFA (trifluoroacetic acid) and subjected to C4 reversed phase HPLC. Elution was with a gradient of 10–25% acetonitrile in 0.1 % TFA/H$_2$O. The solvent was removed by lyophilization and purified protein was resuspended in 0.1% bovine serum albumin in phosphate buffered saline. FIG. 10 depicts HER2 receptor autophophorylation data with MCF-7 cells In response to the purified *E. coli*-derived protein. This material demonstrated full biological activity with an EC$_{50}$ of 0.8 nM. The purified material was also tested in the cell growth assays (Example 5) and was found to be a potent stimulator of cell growth.

The recombinant expression vector for synthesis of HRG-β1 was constructed in a manner similar to HRG-α. The expression vector contained DNA encoding HRG-β1 amino acids from Ser$_{207}$ through Leu$_{273}$ (FIG. 8). This DNA encoding HRG-β1 was recombinantly spliced into the expression vector downstream from the alkaline phosphatase promoter and STII leader sequence. An additional serine residue was spliced on the carboxy terminus as a result of the recombinant construction process. The expression vector encoding HRG-β1 was used to transform *E. coil* and expressed in phosphate depleted medium. Induced *E. coil* were pelleted, resuspended in 10 mM Tris (pH7.5) and sonicated. Cell debris was pelleted by centrifugation and the supernatant was filtered through a sterile filter before assay. The expression of HRG-β1 was confirmed by the detection of protein having the ability to stimulate autophosphorylation of the HER2 receptor in MCF-7 cells.

A similar expression vector was constructed as described for HRG-β1 (above) with a C terminal tyrosine residue instead of the serine residue. This vector was transformed into *E. coli* and expressed as before. Purification of this recombinant protein was achieved as described for recombinant HRG-α. Mass spectrometric analysis revealed that the purified protein consisted of forms which were shorter than expected. Amino acid sequencing showed that the protein had the desired N-terminal residue (Ser) but it was found by mass spectrometry to be truncated at the C terminus The majority (>80%) of the protein consisted of a form 51 amino acids long with a C terminal methionine (MET 271) (SEQ ID NO: 9). A small amount of a shorter form (49 residues) truncated at VAL 269 was also detected. However, both the shortened forms showed full biological activity in the HER2 receptor autophosphorylation assay.

Example 8
ISOLATION OF HEREGULIN β2 and β3 VARIANTS

Heregulin-β2 and -β3 variants were isolated in order to obtain cDNA clones that extend further in the 5' direction. A specifically primed cDNA library was constructed in λgt10 by employing the chemically synthesized antisense primer 3' CCTTCCCGTTCTTCTTCCTCGCTCC (SEQ ID NO: 21). This primer is located between nucleotides 167–190 in the sequence of λher16 (FIG. 4). The isolation of clone λ5'her13 (not to be confused with λher13) was achieved by hybridizing a synthetic DNA probe corresponding to the 5' end of λher16 under high stringency conditions with the specifically primed cDNA library. The nucleotide sequence of λ5'her13 is shown in FIG. 11 (SEQ ID NO: 22). The 496 base pair nucleotide sequence of λ5'her13 is homologous to the sequence of λher16 between nucleotides 309–496 of λ5'her13 and 3–190 of λher16. λ5'her13 extends by 102 amino acids the open reading frame of λher16.

The isolation of variant heregulin-β forms was accomplished by probing a newly prepared oligodT primed λgt10 MDA-MB-231 mRNA-derived cDNA library with synthetic probes corresponding to the 5' end of λ5'her13 and the cysteine rich EGF-like region of λher16. Three variants of heregulin-β were identified, isolated and sequenced. The amino acid homologies between all heregulins is shown in FIG. 15 (SEQ ID NOS: 26–30).

HRG polypeptides λher76 (heregulin-β2) (SEQ ID NO: 23), λher78 (heregulin-β3) (SEQ ID NO: 24) and λher84 (heregulin β2-like) (SEQ ID NO: 25) are considered variants of λher11.1 dbl (heregulin-β1) because although the deduced amino acid sequence is identical between cysteine 1 and cysteine 6 of the EGF-like motif their sequences diverge before the predicted transmembrane domain which probably begins with amino acid 248 in λher11.1 dbl. The nucleotide sequences and deduced amino acid sequences of λher76, λher78 and λher84 are shown in FIGS. 12, 13 and 14.

The variants each contain a TGA stop codon 148 bases 5' of the first methionine codon in their sequences. Therefore the ATG codon at nucleotide position 135–137 of λher16 and the corresponding ATG in the other heregulin clones may be defined as the initiating methionine (amino acid 1). Clones λher11.1 dbl, λher76, λher84 and λher78 all encode glutamine at amino acid 38 (FIG. 15) whereas clone her16 encodes arginine (FIG. 4, position 82).

The deduced amino acid sequence of λher76 (heregulin-β1) reveals a full-length clone encoding 637 amino acids. It shares an identical deduced amino acid sequence as βher11.1 dbl except that residues corresponding to amino acids 232–239 of λher11.1 dbl have been deleted. The deduced amino acid sequence of λher84 shows that it posesses the same amino acid sequence as λher76 from the initiating methionine (amino acid 1, FIG. 15) through the EGF-like area and transmembrane domain. However, λher84 comes to an early stop codon at arginine 421 (λher84 numbering). Thereafter the 3' untranslated sequence diverges. The deduced amino acid sequence of λher78 (heregulin-β$^3$) is homologous with heregulins-β$^1$ and -β2 through amino acid 230 where the sequence diverges for eleven amino acids then terminates. Thus heregulin-β$^3$ has no transmembrane region. The 3' untranslated sequence is not homologous to the other clones.

Example 9
EXPRESSION OF HEREGULIN β FORMS

In order to express heregulin-β forms in mammalian cells, full-length cDNA nucleotide sequences from λher76 (heregulin-β2) or λher84 were subcloned into the mammalian expression vector pRK5.1. This vector is a derivative of pRK5 that contains a cytomegalovirus promoter followed by a 5' intron, a cloning polylinker and an SV40 early polyadenylation signal. COS7, monkey or human kidney 293 cells were transfected and conditioned medium was assayed in the MCF-7 cell p185/her2 autophosphorylation assay. A positive response confirmed the expression of the cDNA's from λher76 (heregulin-β2) and λher84 (heregulin-β3).

Supernatants from a large scale transient expression experiment were concentrated on a YM10 membrane (Amicon) and applied to a heparin Sepharose column as described in Example 1. Activity (tyrosine phosphorylation assay) was detected in the 0.6M NaCl elution pool and was further purifed on a polyaspartic acid column, as previously described By SDS gel analysis and activity assays, the active fractions of this column were highly purified and contained a single band of protein with an apparent molecular weight of 45,000 daltons. Thus, the expressed protein has chromatographic and structural properties which are very similar to those of the native form of heregulin originally isolated from the MDA 231 cells. Small scale transient expression experiments with constructs made from λher84 cDNA also revealed comparable levels of activity in the cell supernatants from this variant form. The expression of the transmembrane-minus variant, heregulin-β3, is currently under investigation.

Example 10 proHRG-α and proHRG-β$_1$ cDNAs were spliced into Epstein Barr virus derived expression vectors containing a cytomegalovirus promoter. rHRGs were purified (essentially as described in Example 2) from the serum free conditioned medium of stably transfected CEN4 cells [human kidney 293 cells (ATCC No. 1573) expressing the Epstein Barr virus EBNA-1 transactivator; see U.S. Ser. No. 07/769,622 incorporated herein]. In other experiments full length proHRG-α, -β$_1$ and -β$_2$ transient expression constructs provided p185$^{HER2}$ phosphorylation activity in the conditioned medium of transfected COS7 monkey kidney cells. However, similar constructs of full length proHRG-β$_3$ failed to yield activity suggesting that the hydrophobic domain missing in proHRG-β$_3$ but present in the other proHRGs is necessary for secretion of mature protein. Truncated versions of proHRG-a (63 amino acids, serin 177 to tyrosine 239) and proHRG-β$_1$ (68 amino acids, serine 177 to tyrosine 241) each encoding the GFD structural unit and immediate flanking regions were also expressed in E. coli; homologous truncated versions of HRG-β$_3$ are expected to be expressed as active molecules. These truncated proteins were purified from the periplasmic space and culture broth of E. coli. transformed with expression vectors designed to secrete recombinant proteins (C. N. Change, M. Rey, B. Bochenr, H. Heyneker, G. Gray, Gene, 55: 189 [1987]). These proteins also stimulated tyrosine phosphorylation of p185$^{HER2}$ but not p107$^{HER1}$, indicating that the biological activity of HRG resides in the EGF-like domain of the protein and that carbohydrate moieties are not essential for activity in this assay. The NTD does not inhibit or suppress this activity.

Example 11

Various human tissues were examined for the presence of HRG mRNA. Transcripts were found in breast, ovary, testis, prostate, heart, skeletal muscle, lung, liver, kidney, salivary gland, small intestine, and spleen but not in stomach, pancreas, uterus or placenta. While most of these tissues display the same three classes of transcripts as the MDA-MB-231 cells (6.6 kb, 2.5 kb and 1.8 kb), only the 6.6 kb message was observed for in heart and skeletal muscle. In brain a single transcript of 2.2 kb is observed and in testis the 6.6 kb transcript appears along with others of 2.2 kb, 1.9 kb and 1.5 kb. The tissue specific expression pattern observed for HRG differs from that of p185$^{HER2}$; for example, adult liver, spleen, and brain contain HRG but not p185$^{HER2}$ transcripts whereas stomach, pancreas, uterus and placenta contain p185$^{HER2}$ transcripts but lack HRG mRNA.

We claim:

1. An isolated polynucleotide which encodes a polypeptide comprising the growth factor domain of heregulin-β2 within SEQ ID NO: 28.

2. The polynucleotide of claim 1 which encodes a polypeptide comprising the N-terminal domain-growth factor domain of heregulin-β2 within SEQ ID NO: 28.

3. The polynucleotide of claim 1 which encodes a polypeptide comprising proheregulin-β2 of SEQ ID NO: 28.

4. The polynucleotide of claim 1 which encodes heregulin-β2 growth factor domain fragment.

5. A recombinant expression vector comprising the polynucleotide of claim 1.

6. A host cell comprising the vector of claim 5.

7. A method of producing a polypeptide comprising culturing the host cell of claim 6 to express the polypeptide and recovering the polypeptide from the host cell.

8. The method of claim 7 wherein the polypeptide comprises proheregulin-β2.

9. The method of claim 7 wherein the polypeptide comprises heregulin-β2 N-terminal domain-growth factor domain.

10. The method of claim 7 wherein the polypeptide is heregulin-β2 growth factor domain fragment.

11. An isolated polynucleotide which encodes a polypeptide comprising the growth factor domain of heregulin-β3 within SEQ ID NO: 30.

12. The polynucleotide of claim 11 which encodes a polypeptide comprising heregulin-β3 of SEQ ID NO: 30.

13. The polynucleotide of claim 11 which encodes heregulin-β3 growth factor domain fragment.

14. A recombinant expression vector comprising the polynucleotide of claim 11.

15. A host cell comprising the vector of claim 14.

16. A method of producing a polypeptide comprising culturing the host cell of claim 15 to express the polypeptide and recovering the polypeptide from the host cell.

17. The method of claim 16 wherein the polypeptide comprises heregulin-β3 of SEQ ID NO: 30.

18. The method of claim 16 wherein the polypeptide is heregulin-β3 growth factor domain fragment.

19. An isolated polynucleotide which encodes a polypeptide comprising the growth factor domain of heregulin-β1 within SEQ ID NO: 9.

20. The polynucleotide of claim 19 which encodes a polypeptide comprising the N-terminal domain-growth factor domain of heregulin-β1 within SEQ ID NO: 9.

21. The polynucleotide of claim 19 which encodes a polypeptide comprising proheregulin-β1 of SEQ ID NO: 27.

22. The polynucleotide of claim 19 which encodes heregulin-β1 growth factor domain fragment.

23. A recombinant expression vector comprising the polynucleotide of claim 19.

24. The expression vector of claim 23 wherein the polynucleotide encodes heregulin-β1 growth factor domain fragment.

25. A host cell comprising the vector of claim 23.

26. A method of producing a polypeptide comprising culturing the host cell of claim 25 to express the polypeptide and recovering the polypeptide from the host cell.

27. The method of claim 26 wherein the polypeptide comprises proheregulin-β1 of SEQ ID NO: 27.

28. The method of claim 26 wherein the polypeptide comprises heregulin-β1 N-terminal domain-growth factor domain.

29. The method of claim 26 wherein the polypeptide is heregulin-β1 growth factor domain fragment.

* * * * *